United States Patent
Fairhead et al.

(10) Patent No.: US 11,236,306 B2
(45) Date of Patent: Feb. 1, 2022

(54) MULTIPLE HOST RANGE BACTERIOPHAGE WITH DIFFERENT TAIL FIBRES

(71) Applicant: PHICO THERAPEUTICS LTD, Cambridge (GB)

(72) Inventors: Heather Fairhead, Cambridge (GB); Adam Wilkinson, Royston (GB); Emmanuele Severi, Cambridge (GB); Neil Anderson, Bishop's Stortford (GB); Katy Pitts, Royston (GB); Anne Barnard, Cambridge (GB)

(73) Assignee: PHICO THERAPEUTICS LTD, Cambridge (GB)

( * ) Notice: Subject to any disclaimer, the term of this patent is extended or adjusted under 35 U.S.C. 154(b) by 0 days.

(21) Appl. No.: 15/517,656

(22) PCT Filed: Oct. 8, 2015

(86) PCT No.: PCT/EP2015/073293
§ 371 (c)(1),
(2) Date: Apr. 7, 2017

(87) PCT Pub. No.: WO2016/055584
PCT Pub. Date: Apr. 14, 2016

(65) Prior Publication Data
US 2017/0306298 A1 Oct. 26, 2017

(30) Foreign Application Priority Data
Oct. 8, 2014 (GB) ..................................... 1417808

(51) Int. Cl.
*C12N 7/00* (2006.01)
*A61K 35/74* (2015.01)
*A61K 35/76* (2015.01)

(52) U.S. Cl.
CPC ............... *C12N 7/00* (2013.01); *A61K 35/74* (2013.01); *A61K 35/76* (2013.01); *C12N 2795/00011* (2013.01); *C12N 2795/00032* (2013.01); *C12N 2795/00043* (2013.01); *C12N 2795/00045* (2013.01)

(58) Field of Classification Search
None
See application file for complete search history.

(56) References Cited

U.S. PATENT DOCUMENTS

2003/0216338 A1* 11/2003 Merril ..................... A61K 35/76
514/44 R

FOREIGN PATENT DOCUMENTS

| WO | 2002/007742 | 1/2002 | | |
|---|---|---|---|---|
| WO | 2002/040678 | 5/2002 | | |
| WO | 2003/076583 | 9/2003 | | |
| WO | 2004/113375 | 12/2004 | | |
| WO | WO-2004113375 A2 | * 12/2004 | ............ | A61K 38/16 |
| WO | 2009/019293 | 2/2009 | | |
| WO | 2016055584 A9 | 4/2016 | | |

OTHER PUBLICATIONS

Barndard. et al. "SASP: rapid bactericidal activity against USA strains of meticillin-resistant *Staphylococcus aureus*." Clinical Microbiology and Infection. Jan. 1, 2008 Wiley-Blackwell Publishing Ltd. United Kingdom Switzerland, vol. 14,Nr:s7,pp. S131-S132, 2008.

Cass, et al. "F-1548—SASPject: Microbiological Characterisation of a Novel Therapeutic Targeting MDR Pseudomonas aeruginosa." 54th Interscience Conference on Antimicrobial Agents and Chemotherapy (ICAAC). Sep. 5-9, 2014, Washington. DC, Sep. 5, 2014: Sep. 5, 2014-Sep. 9, 2014; p. F-1548, 1 page.

Cass, et al. "F-1550—SASPject: A novel Antibacterial Technology Targeting MDR Pseudomonas aeruginosa Demonstrating a Low Propensity for Resistance Development." 54th Interscience Conference on Antimicrobial Agents and Chemotherapy (ICAAC). Sep. 5-9, 2014, Washington, DC. Abstract, 1 page.

Cass, et al. "F-1550 SASPject: A novel Antibacterial Technology Targeting MDR Pseudomonas aeruginosa Demonstrating a Low Propensity for Resistance Development." 54th Interscience Conference on Antimicrobial Agents and Chemotherapy (ICAAC): Sep. 5-9, 2014; Washington, DC Figures, 1 page.

Ceyssens PJ. et al. "Comparative analysis of the widespread and conserved PB1-like viruses infecting Pseudomonas aeruginosa," Environ Microbiol. Nov. 2009:11(11):2874-83.

Le S, et al. "Mapping the tail fiber as the receptor binding protein responsible for differential host specificity of Pseudomonas aeruginosa bacteriophages PaP1 and JG004," PLoS One Jul. 9, 2013:8(7):e68562.

Mikawa YG, et al. "Surface display of proteins on bacteriophage lambda heads." J Mol Biol. Jan. 1, 1996:262(1):21-30. http://ac.els-cdn.com/S0022283696904957/1-s2.0-S0022283696904957-main.pdf?_tid=8e72afe6-b3be-11e5-8358-00000aacb360&acdnat=1452006852_f1ad476461d30e2718c5d95225d194c2.

Mikawa YG, et al. "Surface display of proteins on bacteriophage lambda heads." J Mol Biol. Sep. 13, 1996:262(1):21-30.

Mushtaq, et al. "A novel antibacterial protein which shows rapid bactericidal activity against MRSA in the presence of other antibiotics." 19th European Congress of Clinical Microbiology and Infectious Diseases Helsinki. Finland. May 16-19, 2009. May 16, 2009: May 16, 2009-May 19, 2009. p. P-1081.

Pitts, et al. "F-1551—SASPject: Efficacy of SASPject against Pseudomonas aeruginosa ATCC 27853 in a Mouse Lung Model," 54th Interscience Conference on Antimicrobial Agents and Chemotherapy (ICAAC) Sep. 5-9, 2014, Washington. DC, Abstract, 1 page.

Pitts, et al. "F-1551—SASPject: Efficacy of SASPject against Pseudomonas aeruginosa ATCC 27853 in a Mouse Lung Model," 54th Interscience Conference on Antimicrobial Agents and Chemotherapy (ICAAC). Sep. 5-9, 2014; Washington. DC, Figures, 1 page.

Thomason L. et al. "Recombineering: genetic engineering in bacteria using homologous recombination." Curr Protoc Mol Biol Apr. 2007:Chapter 1:Unit 1.16.

(Continued)

*Primary Examiner* — Nicole Kinsey White
(74) *Attorney, Agent, or Firm* — Robin L. Teskin; Baker, Donelson, Bearman, Caldwell & Berkowitz PC

(57) ABSTRACT

Modified bacteriophage and compositions containing the modified bacteriophage are described. Exemplary compositions are useful for human treatment and may treat various conditions, including bacterial infections.

15 Claims, 44 Drawing Sheets

Specification includes a Sequence Listing.

(56) References Cited

OTHER PUBLICATIONS

Veesler D, et al "A common evolutionary origin for tailed-bacteriophage functional modules and bacterial machineries." Microbiol Mol Biol Rev. Sep. 2011:75(3):423-33. first page of table of contents.

Yoichi M, et al. "Alteration of tail fiber protein gp38 enables T2 phage to infect *Escherichia coli* O157 H7." J Biotechnol. Jan. 12, 2005:115(1):101-7.

* cited by examiner

Figure 10C

Phage ΦPTPX44 is Φ33 with Φ33(N)PTP92(C) tail fibre at native position; Φ33 tail fibre (ΔlacZα) at ectopic position 1

pSMX411
Recombination

Phage ΦPTPX47 is Φ33 with Φ33(N)PTP92(C) tail fibre at native position; Φ33 tail fibre at ectopic position 1; Φ33(N)PTP47(C) tail fibre lacZα at ectopic position 2

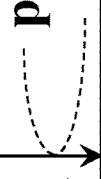

pSMX412
Recombination

Phage ΦPTPX48 is Φ33 with Φ33(N)PTP92(C) tail fibre at native position; Φ33 tail fibre at ectopic position 1; Φ33(N)PTP47(C) tail fibre (ΔlacZα) at ectopic position 2

pSMX417
Recombination

Phage ΦPTPX52 is Φ33 with Φ33(N)PTP92(C) tail fibre at native position; Φ33 tail fibre at ectopic position 1; Φ33(N)PTP47(C) tail fibre at ectopic position 2; (Δendolysin) rpsB-SASP-C lacZα

Figure 12C

Phage ΦPTPX49 is Φ33 with Φ33(N)PTP92(C) tail fibre at native position; Φ33 tail fibre at ectopic position 1; (Δendolysin) rpsB-SASP-C lacZα pSMX416

Recombination 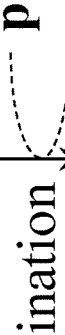

Phage ΦPTP213 is Φ33 with Φ33(N)PTP92(C) tail fibre at native position; Φ33 tail fibre at ectopic position 1; (Δendolysin) rpsB-SASP-C Phage ΦPTPX50 is Φ33 with Φ33(N)PTP47(C) tail fibre at native position; Φ33(N)PTP92(C) tail fibre at ectopic position 1; (Δendolysin) rpsB-SASP-C lacZα pSMX416

Recombination 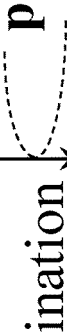

Phage ΦPTPX53 is Φ33 with Φ33(N)PTP47(C) tail fibre at native position; Φ33(N)PTP92(C) tail fibre at ectopic position 1; (Δendolysin) rpsB-SASP-C

Figure 14A.

```
SPM-1    MITPELIPSPFAAQGDKDPIPQTSSTGFANLRDGYTPDYEISLASNNPQAKAVERKIQNQ  60
F8       MITPELIPSPFAAQGDKDPIPQTSSTGFANLRDGYTPDYEISLASNNPQAKAVERKIQNQ  60
PB1      MITPELIPSPFAAQGDKDPIPQTSSTGFANLRDGYTPDYEISLASNNPQAKAVERKIQNQ  60
C36      MITPELIPSPFAAQGDKDPIPQTSSTGFANLRDGYTPDYEISLASNNPQAKAVERKIQNQ  60
LBL3     MITPELIPSPFAAQGDKDPIPQTSSTGFANLRDGYTPDYEISLASNNPQAKAVERKIQNQ  60
Phi33    MITPELIPSPFAAQGDKDPIPQTSSTGFANLRDGYTPDYEISLASNNPQAKAVERKIQNQ  60
LMA2     MITPELIPSPFAAQGDKDPIPQTSSTGFANLRDGYTPDYEISLASNNPQAKVVERKIQNQ  60
KPP12    MITPELIPSPFAAQGDKDPIPQTSSTGFANLRDGYTPDYEISLASNNPQAKAVERKIQNQ  60
JG024    MITPELIPSPFAAQGDKDPIPQTSSTGFANLRDGYTPDYEISLASNNPQAKAVERKIQNQ  60
PTP92    MITPELIPSPFAAQGDKDPIPQTSSTGFANLRDGYTPDYEISLASNNPQAKAVERKIQNQ  60
NH-4     MITPELIPSPFAAQGDKDPIPQTSSTGFANLRDGYTPDYEISLASNNPQAKAVERKIQNQ  60
14-1     MITPELIPSPFAAQGDKDPIPQTSSTGFANLRDGYTPDYEISLASNNPQAKAVERKIQNQ  60
PTP47    MITPELIPSPFAAQGDKDPIPQTSSTGFANLRDGYTPDYEISLASNNPQAKAVERKIQNQ  60
SN       MITPELIPSPFAAQGDKDPIPQTSSTGFANLRDGYTPDYEISLASNNPQAKAVERKIQNQ  60
         :***********************************************.*******

SPM-1    LFFIATQNAQAWQRQMAPPWFQGMPGGYEQNAEVVRVGNDGIMRRYRSMVNANASDPLSS  120
F8       LFFIATQNAQAWQRQMAPPWFQGMPGGYEQNAEVVRVGNDGIMRRYRSMVNANASDPLSS  120
PB1      LFFIATQNAQAWQRQMAPPWFQGMPGGYEQNAEVVRVGNDGIMRRYRSMVNANASDPLSS  120
C36      LFFIATQNAQAWQRQMAPPWFQGMPGGYEQNAEVVRVGNDGIMRRYRSMVNANASDPLSS  120
LBL3     LFFIATQNAQAWQRQMAPPWFQGMPGGYEQNAEVVRVGNDGIMRRYRSMVNANASDPLSS  120
Phi33    LFFIATQNAQAWQRQMAPPWFQGMPGGYEQNAEVVRVGNDGIMRRYRSMVNANAIDPLSS  120
LMA2     LFFIATQNAQAWQRQMAPPWFQGMPGGYEQNAEVVRVGNDGIMRRYRSMVNANASDPLSS  120
KPP12    LFFIATQNAQAWQRQMAPPWFQGMPGGYEQNAEVVRVGNDGIMRRYRSMVNANASDPLSS  120
JG024    LFFIATQNAQAWQRQMAPPWFQGMPGGYEQNAEVVRVGNDGIMRRYRSMVNANASDPLSS  120
PTP92    LFFIATQNAQAWQRQMAPPWFQGMPGGYEQNAEVVRVGNDGIMRRYRSMVNANASDPLSS  120
NH-4     LFFIATQNAQAWQRQMAPPWFQGMPGGYERNAEVVRVGNDGIMRRYRSMVNANASDPLSS  120
14-1     LFFIATQNAQAWQRQMAPPWFQGMPGGYEQNAEVVRVGNDGIMRRYRSMVNANASDPLSS  120
PTP47    LFFIATQNAQAWQRQMAPPWFQDMPGGYEQNAEVVRVGNDGIMRRYRSMVNANASDPLSS  120
SN       LFFIATQNAQAWQRQMAPPWFQGMPGGYEQNAEVVRVGNDGIMRRYRSMVNANASDPLSS  120
         ********************.******:***********************.*****

SPM-1    TTWEEQPAWSVMRSNIPMPAGGSGLSSGGEVITTGRNFNDLLNGTWEFFSDSVVVASQNA  180
F8       TTWEEQPAWSVMRSNIPMPAGGSGLSSGGEVITTGRNFNDLLNGTWEFFSDSVVVASQNA  180
PB1      TTWEEQPAWSVMRSNIPMPAGGPGLSSGGEVITTGRNFNDLLNGTWEFFSDSVVVASQNA  180
C36      TTWEEQPAWSVMRSSIPMPAGGPGLSSGGEVITTGRNFNDLLNGTWEFFSDSVVVASQNA  180
LBL3     TTWEEQPAWSVMRSNIPMPAGGPGLSSGGEVITTGRNFNDLLNGTWEFFSDSVVIASQNA  180
Phi33    TTWEEQPAWSVMRSNIPMPAGGPGLSSGGEVITTGRNFNDLLNGTWEFFSDSVVVASQNA  180
LMA2     TTWEEQPAWSAMRSNIPMPAGGPGLSSGGEVITTGRNFNDLLNGTWEFFSDSVVIASQNA  180
KPP12    TTWEEQPAWSAMRSNIPMPAGGPGLSSGGEVITTGRNFNDLLNGTWEFFSDSVVIASQNA  180
JG024    TTWEEQPAWSVMRTNIPMPAGGPGLSSGGEVITTGRNFNELLNGTWEFFSDAIVVASQNA  180
PTP92    TTWEEQPAWSVMRTNIPMPAGGPGLSSGGEVITTGRNFNELLNGTWEFFSDAIVVASQNA  180
NH-4     TTWEEQPAWSVMRTNIPMPAGGPGLSSGGEVITTGRNFNELLNGTWEFFSDAIVVASQNA  180
14-1     TTWEEQPAWSVMRSSIPMPAGGPGLSSGGEVITTGRNFNDLLNGTWEFFSDSVVIASQNA  180
PTP47    TTWEEQPAWSAMRSNIPMPAGGPGLSSGGEVITTGRNFNDLLNGTWEFFSDSVVIASQNA  180
SN       TTWEEQPAWSVMRSNIPMPAGGPGLSSGGEVITTGRNFNDLLNGTWEFFSDSVVVASQNA  180
         **********.**:.*******.************:********::* *****
```

Figure 14B.

```
SPM-1   PVYPASAGAAAGMLEAKSWVSGANTFCVQRYTDRVGNVAVRGLNAGAWTNWMYAVNVMAL 240
F8      PVYPASAGAAAGMLEAKSWVSGANTFCVQRYTDRVGNVAVRGLNAGAWTNWMYAVNVMAL 240
PB1     PVYPASAGAAAGMLEAKSWISGSNTFCVQRYTDRVGNVAVRGLNAGAWTNWMYAVNVMAL 240
C36     PVYPASAGAAAGMLEAKSWISGSNTFCVQRYTDRVGNVAVRGLNAGAWTNWMYAVNVMAL 240
LBL3    PVYPASAGAAAGMLEAKSWVSGANTFCVQRYTDRVGNVAVRGLNAGAWTNWMYAVNVMAL 240
Phi33   PVYPASAGAAAGMLEAKSWVSGANTFCVQRYTDRVGNVAVRGLNAGAWTNWMYAVNVMAL 240
LMA2    PVYPASAGAAAGMLEAKSWVSGANTFCVQRYTDRVGNVAVRGLNAGAWTNWMYAVNVMAL 240
KPP12   PVYPASAGAAAGMLEAKSWVSGANTFCVQRYTDRVGNVALRGLNAGAWTNWMYAVNVMAL 240
JG024   PVYPASAGAAAGMLEAKSWVSGSNTFCVQRYTDRVGNVAVRGLNAGAWTNWMYAVNVMAL 240
PTP92   PVYPASAGAAAGMLEAKSWVSGSNTFCVQRYTDRVGNVAVRGLNAGAWTNWMYAVNVMAL 240
NH-4    PVYPASAGAAAGMLEAKSWVSGSNTFCVQRYTDRVGNVAVRGLNAGAWTNWMYAVNVMAL 240
14-1    PVYPASAGAAAGMLEAKSWISRSNTFCVQRYTDRVGNVAVRGLNAGEWTNWMYAVNVMAL 240
PTP47   PVYPASAGAAAGMLEAKSWVSGANTFCVQRYTDRVGNVAVRGLNAGAWTNWMYAVNVMAL 240
SN      PVYPASAGAAAGMLEAKSWVSGANTFCVQRYTDRVGNVAVRGLNAGAWTNWMYAVNVMAL 240
        ******************:* :******************:****** ************

SPM-1   QQGRVTYGVAAGSANAYTLTLVPQLQGGLVDGMVLRVKFNAMNTGASTINVSGFGSKAIV 300
F8      QQGRVTYGVAAGSANAYTLTLVPQLQGGLVDGMVLRVKFNAMNTGASTINVSGFGSKAIV 300
PB1     QQGRVTYGVAAGSANAYTLTLVPQLQGGLVDGMILRVKFNTVNTGASTINVSGFAKAIV 300
C36     QQGRVTYGVAAGPANAYTLTLVPQLQGGLVDGMILRVKFNTVNTGASTINVSGFAKAIV 300
LBL3    QQGRVTYGVAAGSANAYTLTLVPQLQGGLVDGMILRVKFNTMNTGASTINVSGFAKAIV 300
Phi33   QQGRVTYGVAAGSANAYTLTLVPQLQGGLVDGMILRVKFNTMNTGASTINVSGLGAKAIV 300
LMA2    QQGRVTYGVAAGSANAYTLTLVPQLQGGLVDGMILRVKFNTMNTGATTINVSGLGAKAIV 300
KPP12   QQGRVTYGVAAGSANAYTLTLVPQLQGGLVDGMILRVKFNTMNTGASTINVSGLGAKAIV 300
JG024   QHGRVTYGTAAGPANAYTLTLVPQIQGGLVDGMILRVKFNTMNTGATTINVSGLGAKAIV 300
PTP92   QHGRVTYGTAAGPANAYTLTLVPQIQGGLVDGMILRVKFNTMNTGATTINVSGLGAKAIV 300
NH-4    QHGRVTYGTAAGPANAYTLTLVPQIQGGLVDGMILRVKFNTMNTGATTINVSGLGAKAIV 300
14-1    QQGRVTYGVAAGPANAYTLTLVPQLQGGLVDGMILRVKFNTVNTGASTINVSGLGAKAIV 300
PTP47   QQGRVTYGVAAGSANAYTLTLVPQLQGGLVDGMILRVKFNTMNTGATTINVSGLGAKAIV 300
SN      QQGRVTYGVAAGSANAYTLTLVPQLQGGLVDGMILRVKFNTMNTGASTINVSGLGAKAIV 300
        *:****** *** *********:*******:******:******::****:******:*:****

SPM-1   GAANFPLTGGELGQGLIAELVFDATGDRWRILAGAPRIQVGNADQDYQAPSWKQVKDYVA 360
F8      GAANFPLTGGELGQGLIAELVFDATGDRWRILAGAPRIQVGNADQDYQAPSWKQVKDYVA 360
PB1     GAANFPLTGGELGQGLIAELVFDATGDRWRILAGAPRIQVGNADQDYQAPSWKQVKDYVA 360
C36     GAANFPLTGGELGQGLIAELVFDATGDRWRILAGAPRIQVGNADQDYQAPSWKQVKDYVA 360
LBL3    GAANFPLTGGELGQGLIAELVFDATGDRWRILAGAPRIQVGNADQDYQAPSWKQVKDYVA 360
Phi33   GAANFPLTGGELGQGLIAELVFDAAGDRWRILAGAPRIQVGNADQDYQAPSWKQVKDYVA 360
LMA2    GAANFPLTGGELGQGLIAELVFDAAGDRWRILAGAPRIQVGNADQDYQAPSWKQVKDYVA 360
KPP12   GAANFPLTGGELGQGLIAELVFDAAGDRWRILAGAPRIQVGNADQDYQAPSWKQVKDYVA 360
JG024   GAANFPLTGGELGQGLIAELVFDAAGDRWRILAGAPRIQVGNADQDYQAPSWKQVKDYVE 360
PTP92   GAANFPLTGGELGQGLIAELVFDAAGDRWRILAGAPRIQVGNADQDYQAPSWKQVKDYVE 360
NH-4    GAANFPLTGGELGQGLIAELVFDAAGDRWRILAGAPRIQVGNADQDYQAPSWKQVKDYVA 360
14-1    GAANFPLTGGELGQGLIAELVFDAAGDRWRILAGAPRIQVGNADQDYQAPSWKQVKDYVA 360
PTP47   GAANFPLTGGELGQGLIAELVFDAAGDRWRILAGAPRIQVGNADQDYQAPSWKQVKDYVA 360
SN      GAANFPLTGGELGQGLIAELVFDAAGDRWRILAGAPRIQVGNADQDYQAPSWKQVKDYVA 360
        ***********************:**********************************:

SPM-1   SQKLTEVDWADVVNKPNVAIQDTTPWFANLELSDARPFIDFHFNNNRAKDFDYRFISEAD 420
F8      SQKLTEVDWADVVNKPNVAIQDTTPWFANLELSDARPFIDFHFNNNRAKDFDYRFISEAD 420
PB1     SQKLTEVDWADVVNKPNVAIQDTTPWFANLELSDARPFIDFHFNNNRAKDFDYRFISEAD 420
C36     SQKLTEVDWADVVNKPNVAIQDTTPWFANLELSDARPFIDFHFNNNRAKDFDYRFISEAD 420
LBL3    SQKLTEVDWADVVNKPNVAIQDTTPWFANLELSDARPFIDFHFNNNRAKDFDYRFISEAD 420
Phi33   SQKLTEVDWADVVNKPNVAIQDTTPWFANLELSDARPFIDFHFSNRAKDFDYRLISEAD 420
LMA2    SQKLTEVDWADVVNKPNVAIQDTTPWFANLELSDARPFIDFHFSNRAKDFDYRLISEAD 420
KPP12   SQKLTEVDWADVVNKPNVAIQDTTPWFANLELSDARPFIDFHFNNNRAKDFDYRFISEAD 420
JG024   SQKLTEVDWTDVVNKPNVAIQDTTPWFANLELSDARPFIDFHFSNRAKDFDYRLISEAD 420
PTP92   SQKLTEVDWTDVVNKPNVAIQDTTPWFANLELSDARPFIDFHFSNRAKDFDYRLISEAD 420
NH-4    SQKLTEVDWTDVVNKPNVAIQDTTPWFANLELSDARPFIDFHFSNRAKDFDYRLISEAD 420
14-1    SQKLTEVDWTDVVNKPNVAIQDTTPWFANLELSDARPFIDFHFSNRAKDFDYRLISEAD 420
PTP47   SQKLTEVDWADVVNKPNVAIQDTTPWFANLELSDARPFIDFHFSNRAKDFDYRLISEAD 420
SN      SQKLTEVDWADVVNKPNVAIQDTTPWFANLELSDARPFIDFHFSNPAKDFDYRLISEAD 420
        *********:*******************************:*********:*****
```

Figure 14C.

```
SPM-1   GSMAFYSRQGSAGPTQDILFSRSNVTFLQPRLDVAKNLAYIANSGPLWQNTTADQPGWKF 480
F8      GSMAFYSRQGSAGPTQDILFSRSNVTFLQPRLDVAKNLAYIANSGPLWQNTTADQPGWKF 480
PB1     GSMAFYSRQGSAGPTQDILFSRSNVTFLQPRLDVAKNLAYIANSGPLWQNTTADQPGWKF 480
C36     GSMAFYSRQGSAGPTQDILFSRSNVTFLQPRLDVAKNLAYIANSGPLWQNTTADQPGWKF 480
LBL3    GSMAFYSRQGSAGPTQDILFSRSNVTFLQPRLDVAKNLAYIANSGPLWQNTTADQPGWKF 480
Phi33   GSLAFYSRQGSAGPTQDILFNRNSVTFFQPRLDVAKNLAYIANSGPLWQNTTADQPGWKF 480
LMA2    GSLAFYSRQGSAGPTQDILFNRNSVTFFQPRLDVAKNLAYIANSGPLWQNTTADQPGWKF 480
KPP12   GSMAFYSRQGSAGPTQDILFSRSNVTFLQPRLDVAKNLAYIANSGSLWQNTTADQPGWKF 480
JG024   GSLAFYSRQGSAGPTQDILFNRNSVTFFQPRLDVAKNLAYIANSGPLWQNTTADQPGWKF 480
PTP92   GSLAFYSRQGSAGPTQDILFNRNSVTFFQPRLDVAKNLAYIANSGPLWQNTTADQPGWKF 480
NH-4    GSLAFYSRQGSAGPTQDILFNRNSVTFFQPRLDVAKNLAYIANSGPLWQNTTADQPGWKF 480
14-1    GSLAFYSRQGSAGPTQDILFNRNSVTFFQPRLDVAKNLAYIANSGPIWQNTTADQPGWKF 480
PTP47   GSLAFYSRQGSAGPTQDILFNRNSVTFFQPRLDVAKNLAYIANSGPLWQNTTADQPGWKF 480
SN      GSLAFYSRQGSAGPTQDILFNRNSVTFFQPRLDVAKNLAYIANSGSLWQNTTADQPGWKF 480
        **:****************.*.,***:*****************.:**************

SPM-1   TFAQGVDANNNAVIAVNTTNPDGSYRSQIMRWDWASTNVIFNNRPLFAGQYVPWDSGNFD 540
F8      TFAQGVDANNNAVIAVNTTNPDGSYRSQIMRWDWASTNVIFNNRPLFAGQYVPWDSGNFD 540
PB1     TFAQGVDANNNAVIAVNTTNPDGSYRSQVMRWDWASTNVIFNNRPLFAGQYVPWDSGNFD 540
C36     TFAQGVDANNNAVIAVNTTNPDGSYRSQIMRWDWASTNVIFNNRPLFAGQYVPWDSGNFD 540
LBL3    TFAQGVDANNNAVIAVNTTNPDGSYRSQIMRWDWASTNVIFNNRPLFAGQYVPWDSGNFD 540
Phi33   TFAQGVDANNNAVIAVNTTNPDGSYRSQIMRWDWASTNVIFNNRPLFAGQYVPWDSGNFD 540
LMA2    TFAQGVDANNNAVIAVNTTNPDGSYRSQVMRWDWASTNVIFNNRPLFAGQYTPWDSGNFD 540
KPP12   TFAQGVDANNNAVIAVNTTNPDGSYRSQIMRWDWASTNVIFNNRPLFAGQYTPWDSGNFD 540
JG024   TFAQGVDANNNAVIAVNTTNPDGSYRSQVMRWDWASTNVIFNNRPLFAGQYTPWDSGNFD 540
PTP92   TFAQGVDANNNAVIAVNTTNPDGSYRSQVMRWDWASTNVIFNNRPLFAGQYTPWDSGNFD 540
NH-4    TFAQGVDANNNAVIAVNTTNPDGSYRSQVMRWDWASTNVIFNNRPLFAGQYTPWDSGNFD 540
14-1    TFAQGVDANNNAVIAVNTTNPDGSYRSQVMRWDWASTNVIFNDRPLFAGQYTPWDSGNFD 540
PTP47   TFAQGVDANNNAVIAVNTTNPDGSYRSQVMRWDWASTNVIFNNRPLFAGQYTPWDSGNFD 540
SN      TFAQGVDANNNAVIAVNTTNPDGSYRSQVMRWDWASTNVIFNNRPLFAGQYTPWDSGNFD 540
        **************************:*************** ******* *******.

SPM-1   PATKLTVGTTNNISGPTGIRNTTSNTGNMNTWGSSSTTASYGNAALQIFGRGGGEPAAIY 600
F8      PATKLTVGTTNNISGPTGIRNTTSNTGNMNTWGSSSTTASYGNAALQIFGRGGGEPAAIY 600
PB1     PATKLTVGTTNNISGPTGIRNTTSNTGNMNTWGSSSTTASYGNAALQIFGRGGGEPAAIY 600
C36     PATKLTVGTTNNISGPTGIRNTTSNTGNMNTWGSSSTTASYGNAAVQIFGRGDGEPAAIY 600
LBL3    PATKLTVGTTNNISRPTGIRNTTSNTGNMNTWGSSSTTASYGNAALQIFGRGGGEPAAIY 600
Phi33   PSTKLTVNATNQIAGPTGIRNTNGNTGNMNTWGSGSTTASYGNAALQIFGKGGGEPAALY 600
LMA2    PSTKLTVNATNQIAGPTGIRNTNGNTGNMNTWGSGSTTASYGNAAIQIFGKGGGEPAAIY 600
KPP12   PSTKLTVNATNQIAGPTGIRNTNGNTGNMNTWGSSSTTASYGNAALQIFGKGGGEPAALY 600
JG024   PSTKLTVSATNQISGPTGIRNTNGNTGNMNTWGSGSTTASYGNAAIQIFGKGGGEPAAIY 600
PTP92   PSTKLTVSATNQISGPTGIRNTNGNTGNMNTWGSGSTTASYGNAAIQIFGKGGGEPAAIY 600
NH-4    PSTKLTVSATNQIAGPTGIRNTNGNTGNMNTWGSGSTTASYGNAAIQIFGKGGGEPAAIY 600
14-1    PSTKLTVSATNQIAGPTGIRNTNGNTGNMNTWGSGSTTASYGNAAIQIFGKGGGEPAAIY 600
PTP47   PSTKLTVSATNQIAGPTGIRNTNGNTGNMNTWGSGSTTASYGNAAIRIFGKGGGEPAAIY 600
SN      PSTKLTVRATNQIAGPTGIQNTNGNTGNMNTWGSGSTTASYGNAAIQIFGKGGGEPAAIY 600
        *:***** :**:*: ****:**.*********.**********.::***:*.*****:*

SPM-1   FDNSQTGWYLGMDKDGQLKRAGWSLGNNSYVVTDESNIRNHVNGMSGAPVWGGQWFWGEW 660
F8      FDNSQTGWYLGMDKDGQLKRAGWSLGNNSYVVTDESNIRNHVNGMSGAPVWGGQWFWGEW 660
PB1     FDNSQTGWYLGMDKDGQLKRAGWSLGNNSYVVTDESNIRNHVNGMSGAPVWGGQWFWGEW 660
C36     FDNSQTGWYLGMDKDGQLKRAGWSLGNNSYVVTDESNIRFHVNSMAGTPVWGGNEFWGPW 660
LBL3    FDNSQTGWYLGMDKDGQLKRAGWSLGNNSYVVTDESNIRFHVNSMAGTPVWGGNEFWGPW 660
Phi33   FDNSQTGWYLGMDKDGQLKRAGWSLGNNAYVITDESNIRFHVNSMAGTPVWGGNEFWGPW 660
LMA2    FDNSQTGWYLGMDKDGQLKRAGWSLGNNSYVITDELNIRNHIGMAARPVWGGNEFWGPW 660
KPP12   FDNSQTGWYLGMDKDGQLKRAGWSLGNNAYVITDESNIRFHVNSMAGTPVWGGNEFWGSW 660
JG024   FDNSQTGWYLGMDKDGQLKRAGWSLGNNSYVITDESNIRTHINTMAARPIWGNVEFWGPW 660
PTP92   FDNSQTGWYLGMDKDGQLKRAGWSLGNNSYVITDESNIRTHINTMAARPIWGNVEFWGPW 660
NH-4    FDNSQTGWYLGMDKDGQLKRAGWSLGNNSYVITDESNIRTHINTMAARPIWGNVEFWGPW 660
14-1    FDNSQTGWYLGMDKDGRLKRAGWSLGNNSYVITDESNIRTHINTMAARPIWGNVEFWGPW 660
PTP47   FDNSQTGWYLGMDKDGQLKRAGWSLGNNSYVITDESNIRTHINTMAARPIWGNVEFWGPW 660
SN      FDNSQTGWYLGMDKDGQLKRAGWSLGNNSYVITDESNIRTHINTMAARPIWGGVEFWGPW 660
        ****************:************:*****.*** *** *:*  *:**.  *** *
```

Figure 14D.

```
SPM-1   NFNPNTKLTIKAGTQETSSTAIFSGTLPFAPIASLSDYSQAPLTIYN--SPTGPSAKPAV 718
F8      NFNPNTKLTIKAGTQETSSTAIFSGTLPFAPIASLSDYSQAPLTIYN--SPTGPSAKPAV 718
PB1     NFNPNTKLTIKAGTQETSSTAIFSGTLPFAPIASLSDYSQAPLTIYN--SPTGPSAKPAV 718
C36     NFNPNTKLTIKAGTQETSSTAIFSGTMPFAPIASLSDYSQAPLTIYN--SPTGPSAKPAV 718
LBL3    NFNPNTKLTIKAGTQETSSTAIFSGTMPFAPIASLSDYSQAPLTVYN--SPTGPSAKPAV 718
Phi33   NFNPNTKLTIKAGTQETSSTAIFSGTMPFAPIASLSDYSQAPLTVYN--APTGPSAKPAV 718
LMA2    NFNPNTKLTIKAGTQETSSTAIYSGTMPFAPIASLSDYSQAPLTIYN--APTGPSAKPAV 718
KPP12   NFNPNTKLTIKAGTQETSSTAIFSETMPFAPIASLSDYSQAPLTIYN--APTGPSAKPAV 718
JG024   NFDPNLKLTLNAFNDSSYTRMTNSGAKDVG-IASMTSYADAAMSFFNYEASNPTGPRAAV 719
PTP92   NFDPNLKLTLNAFNDSSYTRMTNSGAKDVG-IASMTSYADAAMSFFNYEASNPTGPRAAV 719
NH-4    NFNPNTKLTLGSFNDSQHTRMVNSAAKDVG-IASMTSYADAAMSFFNYEASTPTGNRAAV 719
14-1    NFDPNLKLTLNAFNDSSYTRMTNSGAKDVG-IASMTSYADAAMSFFNYEASNPTGPRAAV 719
PTP47   NFPNTKLTLGSFNDGQHTRMVNSAAKDVG-IASMTSYADAAMSFFNYEASTPTGNRAAV 719
SN      NFNPNTKLTLGSFNDSQHTRMVNSAAKDVG-IASMTSYADAAMSFFNYEASTPTGNRAAV 719
        **:** ***: . ,:   :      *  :   ,. ***:,.*:;*.::..*  :..  .. :.**

SPM-1   IAFIRPGNWGAFFGIDTDNKLKWGGGSLGNNSREIADSSNIMNLWASNPTAPSWNGQTVW 778
F8      IAFIRPGNWGAFFGIDTDNKLKWGGGSLGNNSREIADSSNIMNLWASNPTAPSWNGQTVW 778
PB1     IAFIRPGNWGAFFGIDTDNKLKWGGGSLGNNSREIADSSNIMNLWASNPTAPSWNGQTVW 778
C36     IAFIRPGNWGAFFGIDTDNKLKWGGGSLGNSSREIADSSNIMNLWAANPTAPSWNGQTVW 778
LBL3    IAFIRPGNWGAFFGIDTDNKLKWGGGSLGNSSREIADSSNIMNLWAANPTAPTWNGQTIW 778
Phi33   IAFIRPGNWGAFFGIDTDNKLKWGGGSLGNSSREIADSSNIMNLWAANPTAPSWNGQTIW 778
LMA2    IAFIRPGNWGAFFGLDTDNKLKWGGGSLGNSSMEIADSSNIMNLWAANPTAPTWNGQTVW 778
KPP12   IAFIRPGNWGAFFGLDTDNKLKWGGGSLGNSSREIADSRNIMNLWAANPTAPTWNGQTVW 778
JG024   ISFVRNGSRGVLFGLDSDNKLKWGGYSLGAVAFEIADSNNLMSLWSSHAAAPNWNGQTIW 779
PTP92   ISFVRNGSRGVLFGLDSDNKLKWGGYSLGAVAFEIADSNNLMSLWSSHAAAPNWNGQTIW 779
NH-4    ISFVRNGARGVLFGLDTDNKLKWGGYSLGAVAFEIADSNNLMSLWSSHAAAPNWNGQTIW 779
14-1    ISFVRNGSRGVLFGLDSDNKLKWGGYSLGAVAFEIADSNNLMSLWSSHAAAPNWNGQTIW 779
PTP47   ISFVRNGARGVLFGLDTDNKLKWGGYSLGAVAFEIADSNNLMSLWSSHAAAPNWNGQTIW 779
SN      ISFVRNGARGVLFGLDTDNKLKWGGYSLGAVAFEIADSNNLMSLWSSHAAAPNWNGQTIW 779
        *:*:* *  *:.:**:*:.*******  ***  ; ***** *:*.**::..:**.*****:*

SPM-1   RSGNFDPATKVDLNAANATNGSMIFNRISGTGSGIASSGRVGAINLQNGAHSGQAAAVTF 838
F8      RSGNFDPATKVDLNAANATNGSMIFNRISGTGSGIASSGRVGAINLQNGAHSGQAAAVTF 838
PB1     RSGNFDPATKVDLNAANATNGNMIFNRISGTGSGIASSGRVGAINLQNGAHSGQAAAVTF 838
C36     RSGNFDPATKVDLNAANATNGNMVFNRISGTGSGIASSGRVGAINLQNGAHSGQAAAVTF 838
LBL3    RSGNFDPATKVDLNAANATNGNMIFNRIAGTGSGIASSDRVGAISLQNGATAGAAAAVTF 838
Phi33   RSGNFDPATKVDLNAANATNGNMIFNRIAGTGSGIASSGRVGAINLQNGEHSGQAAAVTF 838
LMA2    RSGNFDPATKVDLNAPNATNGNMIFNRIAGTGSGIASSGRVGAISLQNGATAGAAAAVTF 838
KPP12   RSGNFDPATKVDLNAPNATNGNMIFNRIAGTGSGIASSGRVGAISLQNGATAGAAAAVTF 838
JG024   RSGNFNPDTKATLAARNTTSSPTIFS---YGASGIASTGQVGALVVENNSVTNTAAAITF 836
PTP92   RSGNFNPDTKATLAARNTTSSPTIFS---YGASGIASTGQVGALVVENNSVTNTAAAITF 836
NH-4    RSGNFNPDTKATLAARNTTSSPTIFS---YGASGIASTGQVGALVVENNSVTNTAAAITF 836
14-1    RSGNFNPDTKATLAARNTTSSPTIFS---YGASGIASTGQVGALVVENNSVTNTAAAITF 836
PTP47   RSGNFNPDTKATLAARNTTSSPTIFS---YGASGIASTGQVGALVVENNSVTNTAAAITF 836
SN      RSGNFNPDTKATLAARNTTSSPTIFS---YGASGIASTGQVGALVVENNSVTNTAAAITF 836
        *****:* **. * * *;*.. ;*.    .*****:,****: ::*.  :.  **:**

SPM-1   ERGGSIFVNFGLDTDNVLKVGGGNLGANAYPVIHAGNYNNYINQALVQVGLGGVGSYGIF 898
F8      ERGGSIFVNFGLDTDNVLKVGGGNLGANAYPVIHAGNYNNYINQALVQVGLGGVGSYGIF 898
PB1     ERGGSIFVNFGLDTDNVLKVGGGNLGANAYPVIHAGNYNNYINQALVQVGLGGVGSYGIF 898
C36     ERGGSIFVNFGLDTDNVLKVGGGNLGANAYPVIHAGNYNNYINQALVQVGLGGVGSYGIF 898
LBL3    ERGGGFFVNFGLDTDNVLKVGGGNLGANAYPVIHAGNYNNYINQALVQVGLGGVGSYGIF 898
Phi33   ERGGSIFVNFGLDTDNVLKVGGGNLGANAYPVIHAGNYNNYINQALVQVGLEGVGSYGIF 898
LMA2    ERGGGFFVNFGLDTDNVLKVGGGNLGANAYPVIHAGNYNSYINQALVQVGLGGVGSYAAL 898
KPP12   ERGG-FFVNFGLDTDNVLKVGGGNLGANAYPVIHAGNYNSYINQALVQVGLGGVGSYAAL 897
JG024   HSPQKYQVNFGLDADNVVKIGGGTMGGVAYPIIHSGNYNNYINQALVQVGLGGVGSYAIL 896
PTP92   HSPQKYQVNFGLDADNVVKIGGGTMGGVAYPIIHSGNYNNYINQALVQVGLGGVGSYAIL 896
NH-4    HSPQKYQVNFGLDADNVVKIGGGTMGGVAYPIIHSGNYNNYINQALVQVGLGGVGSYAIL 896
14-1    HSPQKYQVNFGLDADNVVKIGGGTMGGVAYPIIHSGNYNNYINQALVQVGLGGVGSYGIF 896
PTP47   HSPQKYHVNFGLDADNVVKIGGGTMGGVAYPIIHSGNYNNYINQALVQVGLEGVGSYGIF 896
SN      HSPQKYQVNFGLDADNVVKIGGGTMGGVAYPIIHSGNYNNYINQALVQVGLGGVGSYGIF 896
        .     *****:****:****:*:*. :***:***.****.**********   ****. :
```

Figure 14E.

```
SPM-1   AVLDNAAPIATVQPGVVVDGSILIYSSCAANYNSGQKPAGTWRCMGYVVNRDANTADSAT  958
F8      AVLDNAAPIATVQPGVVVDGSILIYSSCAANYNSGQKPAGTWRCMGYVVNRDANTADSAT  958
PB1     AVLDNAAPIATVQPGVVVDGSILIYSSCAANYNSGQKPAGTWRCMGYVVNRDANTPDSAT  958
C36     AVLDNAAPIATVQPGVVVDGSILIYSSCSANYNSGQRPAGTWRCMGYVVNRDANTPDSAT  958
LBL3    AVLDYAAPTATVQPGVIVDGSILIYSSCSAHYNSGQRPAGTWRCMGYVLNRDARDPDSAT  958
Phi33   AVLDNAAPTATVQPGVVVDGSILIYSSCAANYNSGKRPAGTWRCMGYVVNRDANTPDSAT  958
LMA2    AVYDTSAPASSVGPGTILDGSVLFYSSFNANFRSGTKPTGTWRCMGYILNRDGTNPDSAT  958
KPP12   AVYDTSAPASSVGPGTILDGSVLFYSSFDANFRSGTKPTGTWRCMGYVLNRDGTNPDSAA  957
JG024   AVLDTSAPAASIAPGTIMDSSKLFYSSCDSTYRSSASPTGTWRCMGYVYNRDSTNGDSAS  956
PTP92   AVLDTSAPAASIAPGTIMDSSKLFYSSCDSTYRSSASPTGTWRCMGYVYNRDSTNGDSAS  956
NH-4    AVLDTSAPAASIAPGTIMDSSKLFYSSCDSTYRSSARPTGTWRCMGYVYNRDSTNGDSAS  956
14-1    AVLDNAAPIATVQPGVVVDGSILIYSSCAANYNSGQRPAGTWRCMGYVVNRDANTPDSAT  956
PTP47   AVLDYAAPTATVRPGVVVDGSILIYSSCAANYNSGQRPAGTWRCMGYVVNRDANTPDSAT  956
SN      AVLDNAAPTATVQPGVVVDGSILIYSSCAANYNSGQRPAGTWRCMGYVVNRDANTPDSAT  956
        ** * :** ::: **.::*.* *:***    :.*.  *:********: ***.  ***:

SPM-1   LFQRVT 964 (SEQ ID NO: 57)
F8      LFQRVT 964 (SEQ ID NO: 58)
PB1     LFQRVT 964 (SEQ ID NO: 59)
C36     LFQRVT 964 (SEQ ID NO: 60)
LBL3    LFQRVT 964 (SEQ ID NO: 61)
Phi33   LFQRVT 964 (SEQ ID NO: 62)
LMA2    LFQRVT 964 (SEQ ID NO: 63)
KPP12   LFQRVT 963 (SEQ ID NO: 64)
JG024   LFQRVT 962 (SEQ ID NO: 65)
PTP92   LFQRVT 962 (SEQ ID NO: 66)
NH-4    LFQRVT 962 (SEQ ID NO: 67)
14-1    LFQRVT 962 (SEQ ID NO: 68)
PTP47   LFQRVT 962 (SEQ ID NO: 69)
SN      LFQRVT 962 (SEQ ID NO: 70)
        ******
```

MULTIPLE HOST RANGE BACTERIOPHAGE WITH DIFFERENT TAIL FIBRES

RELATED APPLICATIONS

This application is a U.S. National Phase application of International Application No. PCT/EP2015/073293, filed Oct. 8, 2015, which claims priority to United Kingdom Application No. 1417808.1 GB, filed Oct. 8, 2014, each of which is incorporated herein by reference.

SEQUENCE LISTING DISCLOSURE

This application includes as part of its disclosure a biological sequence listing which is being concurrently submitted through EFS-Web. Said biological sequence listing is contained in a file named "1143297o003201.txt" which was created on Apr. 6, 2017, and has a size of 126,972 bytes, and is hereby incorporated by reference in its entirety.

BACKGROUND TO THE INVENTION

The World Health. Organisation's 2014 report on global surveillance of antimicrobial resistance reveals that antibiotic resistance is a global problem that is jeopardising the ability to treat common infections in the community and hospitals. Without urgent action, the world is heading towards a post-antibiotic era, in which common infections and minor injuries, which have been treatable for decades, can once again kill (WHO. 2014). Antibiotic resistance complicates patients' recovery from even minor operations and is increasingly causing treatment failures. In fact, there are now strains of some genera of bacteria circulating globally which are resistant to all available antibiotics. Such strains commonly fall within the scope of the so-called ESKAPE pathogens—*Enterococcus faecium, Staphylococcus aureus, Klebsiella pneumoniae, Acinetobacter baumannii, Pseudomonas aeruginosa* and *Enterobacter* species (Boucher et al., 2009). The term ESKAPE pathogens was coined by Boucher et al. to emphasize that these bacteria currently cause a majority of hospital infections in the US and Europe and can effectively "escape" the majority, if not all, available antibiotics with panantibiotic-resistant infections now occurring. The death rate for patients with serious infections caused by common bacteria treated in hospitals is approximately twice that of patients with infections caused by the same non-resistant bacteria, e.g. people with methicillin-resistant *Staphylococcus aureus* (MRSA) infections are estimated to be 64% more likely to die than people with a non-resistant form of the infection (WHO, 2014). Of the Gram positive bacteria, methicillin resistant *S. aureus* continues to be a major cause of morbidity and mortality in hospitals in the US and Europe. However, in more recent years, several highly resistant Gram negative pathogens, including *Acinetobacter* species, multidrug resistant (MDR) *P. aeruginosa*, and carbapenem-resistant *Klebsiella* species and *Escherichia coli*, have emerged as major pathogens causing serious, and sometimes untreatable, infections. Advances in medicine mean that increasingly complex procedures take place: and these advances are leading to a growing number of elderly patients and patients undergoing surgery, transplantation, and chemotherapy all of which will produce an even greater number of immunocompromised individuals at risk of these infections Walker et al., 2009. This phenomenon has led to a greater dependence on, and requirement for, effective antibiotics.

*P. aeruginosa* is one bacterium which is frequently multi-drug resistant (MDR) having intrinsic resistance due to low permeability of its outer membrane limiting drugs getting into the cell, and a multitude of efflux pumps to expel any drugs that successfully manage to enter the cell. *P. aeruginosa* is also acquiring additional resistance mechanisms, including resistance to the "antibiotics of last resort" for Gram negatives, the carbapenems. *P. aeruginosa* causes approximately 10% of all hospital acquired infections and is the second leading cause of hospital-acquired pneumonia, which accounts for 50% of all hospital-acquired infection prescribing. *P. aeruginosa* infections in hospitals commonly require intravenous (IV) treatment with current standard of care for *P. aeruginosa* infections dictating that patients are treated with at least two antibiotics. Unfortunately, resistance frequently develops in patients during therapy. With so few new classes of antibiotic developed and approved for market within the last 30-40 years, there is a critical need for novel, safe and effective antibacterial agents.

As an alternative to conventional antibiotics, one family of proteins which demonstrate broad spectrum antibacterial activity inside bacteria comprises the α/β-type small acid-soluble spore proteins (known henceforth as SASP). Inside bacteria, SASP bind to the bacterial DNA: visualisation of this process, using cryoelectron microscopy, has shown that SspC, the most studied SASP, coats the DNA and forms protruding domains and modifies the DNA structure (Francesconi et al., 1988; Frenkiel-Krispin et al., 2004) from B-like (pitch 3.4 nm) towards A-like (3.18 nm; A-like DNA has a pitch of 2.8 nm). The protruding SspC motifs interact with adjacent DNA-SspC filaments packing the filaments into a tight assembly of nucleo-protein helices. In 2008, Lee et al. reported the crystal structure at 2.1 Å resolution of an α/β-type SASP bound to a 10-bp DNA duplex. In the complex, the α/β-type SASP adopt a helix-turn-helix motif, interact with DNA through minor groove contacts, bind to approximately 6 bp of DNA as a dimer and the DNA is in an A-B type conformation. In this way DNA replication is halted and, where bound, SASP prevent DNA transcription. SASP bind to DNA in a non-sequence specific manner (Nicholson et al., 1990) so that mutations in the bacterial DNA do not affect the binding of SASP. Sequences of α/ß-type SASP may be found in appendix 1 of WO02/40678, including SASP-C from *Bacillus megaterium* which is the preferred α/ß-type SASP.

WO02/40678 describes the use as an antimicrobial agent of bacteriophage modified to incorporate a SASP gene. In order to provide effective production of the modified bacteriophage in a bacterial host, WO02/40678 aims to avoid expression of the SASP gene during proliferation of the production host. To this end, the SASP gene was put under the control of an inducible promoter. In one arrangement, the SASP gene was put under the control of a lysis gene promoter which is active only at the end of the bacteriophage life cycle by insertion into the lysis genes of a temperate bacteriophage. In doing so the phage remains viable as a prophage. In another arrangement, the SASP gene could be located elsewhere on the bacteriophage chromosome and placed under the control of a bacteriophage or bacterial promoter whereby the lytic cycle could be left to run its course. In this arrangement, the bacterial promoter would be non-constitutive and could be up-regulated by environmental cues. It was thought that proliferation of the bacterial production host would otherwise be prevented owing to the presence of the SASP gene product, particularly if the SASP gene was under the control of a constitutive promoter.

WO2009019293 describes that effective production of bacteriophage may be achieved where the bacteriophage has been modified to carry a gene encoding a SASP under the control of a promoter which is controlled independently of the bacteriophage, and which is constitutive with no exogenous or in trans regulation necessary or provided. An example is the fbaA promoter from *S. aureus* which is used to drive expression of the SASP-C gene from *Bacillus megaterium* and which, when present in multiple copies, for example following infection of target cells, drives toxic levels of SASP expression.

Bacteriophage vectors modified to contain a SASP gene have generally been named SASPject vectors. Once the SASP gene has been delivered to a target bacterium, SASP is produced inside those bacteria where it binds to bacterial DNA and changes the conformation of the DNA from B-like towards A-like. Production of sufficient SASP inside target bacterial cells causes a drop in viability of affected cells.

Bacteriophage have been used as medicines for the treatment of bacterial infections since the 1920s or 30s. Generally, bacteriophage are specific to their bacterial host. Some bacteriophage are temperate and others non-temperate. Temperate phage are able to infect the host cell and integrate into the host cell genome becoming a prophage which is generally harmless to the host cell in this state. Non-temperate or "lytic" phage are only able to replicate in a lytic lifestyle by making new bacteriophage progeny and ending in lysis of the host cell and release of mature phage particles. For useful medicines, the challenge is to provide bacteriophage compositions which can be used to treat infection from a variety of different bacteria in an effective way. It is commonly thought that this is achieved using the most potent bacteriophage compositions available: those with a broadened host range, possibly as a mixture or "cocktail" of bacteriophage, which are obligately lytic and retain viability through replication and release during treatment (Carlton, 1999; Kutateladze and Adamia, 2010). Cocktails of wild type phage have been used to ensure sufficient spectrum of activity against clinical strains of bacteria (Burrowes and Harper, 2012). Such cocktails can consist of up to 20 different and unrelated phage (Abedon 2008). As an alternative to the cocktail approach, *E. coli* bacteriophage K1-5 has been isolated. This is a naturally-occurring obligately lytic phage which carries more than one host range determinant allowing it to infect and replicate on both K1 and K5 strains of *E. coli* (Scholl et al, 2001). These phage are considered to be extra potent.

There remains a need to provide improved bacteriophage for use in treating bacterial infections in medicine as well as inhibiting or preventing bacterial cell growth in medical and non-medical situations.

SUMMARY OF THE INVENTION

In a first aspect, the present invention provides a modified bacteriophage capable of infecting a plurality of different target bacteria, which bacteriophage includes an α/β small acid-soluble spore protein (SASP) gene encoding a SASP which is toxic to the target bacteria; wherein the bacteriophage is non-lytic; wherein the bacteriophage expresses a plurality of different host range determinants (HRD); and wherein each HRD has a different bacterial host specificity. The bacterial host specificity of the HRD is advantageously within the same bacterial species.

It has surprisingly been found that a modified bacteriophage may be produced which is capable of infecting a variety of different target bacteria and which is effective for use in medicine even though the bacteriophage is non-lytic. The bacteriophage has an enhanced host range because it expresses a plurality of different HRD, wherein each HRD has a different bacterial host specificity. Such phage may be produced by genetic engineering, for example by selecting HRD from phage which infect the same bacterial species. Having created such an extra-potent phage, it can then be rendered non-lytic, and hence non-viable and yet still be suitable as a SASPject vector.

In one aspect, the term 'SASP' as used in the present specification refers to a protein with α/β-type SASP activity, that is, the ability to bind to DNA and modify its structure from its B-like form towards its A-like form, and not only covers the proteins listed in appendix 1 of WO02/40678, but also any homologues thereof, as well as any other protein also having α/β-type SASP activity. In an alternative aspect, the term 'SASP' as used in the specification refers to any protein listed in appendix 1 of WO02/40678, or any homologue having at least 70%, 75%, 80%, 85%, 90%, 92%, 94%, 95%, 96%, 98% or 99% sequence identity with any one of the proteins listed in appendix 1 of WO02/40678. In another alternative aspect, the term 'SASP' as used in the specification refers to any protein listed in appendix 1 of WO02/40678.

The modified bacteriophage may be non-lytic because it comprises an inactivated lysis gene. Insertion of sequence into the lysis gene or removal of the lysis gene would render this gene inactive. The lysis gene may conveniently be inactivated by insertion of the SASP gene. The SASP gene may be chosen from any one of the genes encoding the SASP disclosed in Appendix 1 of WO02/40678. In a preferred arrangement the SASP is SASP-C. The SASP-C may be from *Bacillus megaterium*.

It is preferred that the SASP gene is under the control of a constitutive promoter which is advantageously sufficiently strong to drive production of toxic levels of SASP when the modified bacteriophage is present in multiple copies in the target bacterium. Useful constitutive promoters include pdhA for pyruvate dehydrogenase E1 component alpha sub units, rpsB for the 30S ribosomal protein S2, pgi for glucose-6-phosphate isomerase and the fructose bisphosphate aldolase gene promoter fda. Preferred regulated promoters, active during infection, are lasB for elastase. These promoters are typically from *P. aeruginosa*. Promoters having a sequence showing at least 90% sequence identity to these promoter sequences may also be used.

The present invention is generally applicable to bacteriophage infecting a variety of different target bacteria. In one arrangement at least one of the target bacteria is *Pseudomonas*. Advantageously, the plurality of different target of bacteria is a plurality of different *Pseudomonas* bacteria. An important target is *Pseudomonas aeruginosa*.

It was not previously considered obvious that use of an obligate lytic phage would be suitable as a SASPject vector since a requirement of a SASPject vector is that it is specifically not lytic for optimal therapeutic use, giving an increased time window for SASP expression and enabling prevention of rapid lysis upon treatment in vivo, thus limiting the potential release of antibiotic resistance genes and toxic cell wall components which can lead to a dangerous inflammatory response.

The approach described in the present invention is advantageous as compared to the cocktail approach described previously. Mixtures of modified bacteriophage, such as SASPject vectors are identical in structure and genome sequence, other than carrying one or more extra HRD. One advantage is that control of the manufacturing process for the mix of SASPjects will be straightforward, which is an important aspect of a pharmaceutical preparation: the process will be materially the same for phage modified to carry one or more heterologous HRD as they share identical or near-identical biophysical properties. Another advantage is that the in vivo characteristics of the SASPject vectors are likely to be similar, e.g. pharmacokinetics/pharmacodynamics, as each vector is structurally the same or similar.

In the present invention it has been found that phage can be created which are extra-potent obligately-lytic bacteriophage carrying one or more extra HRD. Surprisingly, such phage can be used to make enhanced SASPject vectors by rendering these phage non-lytic and non-viable, by insertion or replacement of a lytic gene(s) with a gene for a SASP. Phage suitable for such modification may be isolated by screening for phage capable of infecting a chosen bacterial species. For instance, phage may be isolated which infect *Pseudomonas aeruginosa*, by screening for phage from environmental sources which are able to form plaques on representative *P. aeruginosa* strains (Gill and Hyman, 2010). Isolated phage may have their whole genomes sequenced and annotated. HRD may be tail fibre proteins, which are commonly found to be proteins responsible for the initial recognition/binding to the host bacterium, for instance in phage T4, T5 and T7 (Rakhuba et al., 2010). Alternatively other HRD may be baseplate proteins. Phage genomes may be searched for potential HRD sequences by assessing the homology of all proteins in the phage genome to known sequences, using BLAST searches.

According to the present invention it is preferred that each HRD has a broad host range. This may be defined as the ability to infect >50% of a diverse collection or clinical isolates, totaling at least 35, preferably at least 40, more preferably at least 44, and most preferably >50 in number. Such isolates should be from a range of geographical locations, including Europe, the Americas, and Asia, should carry a diverse range of antibiotic resistance phenotypes, including multi-drug resistant (MDR) strains, and should be from a diverse range of infection sites, such as strains cultured from blood, lung and skin infections. Such isolates can be obtained from public strain collections such as the American Type Culture Collection (ATCC) and the National Collection of Type Cultures (NCTC). HRD proteins have at least one region involved in structural incorporation into the phage and at least one region involved in host recognition. Generally, in the case of tail fibre proteins, each comprises a C-terminal receptor binding region for binding to the target bacteria and an N-terminal region linking the C-terminal receptor binding region to the body of the bacteriophage. In one arrangement, taking Phi33 and related phage as an example, the N-terminal region comprises amino acids 1 to 628 of the tail fibre protein and the C-terminal region comprises the amino acids 629 to 964 of the tail fibre protein.

The C-terminal region may have no more than 96% amino acid sequence identity with the C-terminal region of bacteriophage Phi33 and may be from any one of the bacteriophage Phi33, LBL3, SPM-1, F8, PB1, KPP12, LMA2, SN, 14-1, JG024, NH-4, PTP47, C36, PTP92 and PTP93. Lower amino acid sequence identities in the C-terminal region are preferred, Advantageously the sequence identity is less than 90%, more advantageously less than 80%, preferably less than 70%, more preferably less than 60%, still more preferably less than 50%, particularly preferably less than 40%, more particularly preferably less than 30%. The N-terminal region may have at least 90% and advantageously at least 95% amino acid sequence identity with the N-terminal region of bacteriophage Phi33 and may be from any one of bacteriophage Phi33, LBL3, SPM-1, F8, PB1, KPP12, LMA2, SN, 14-1, JG024, NH-4, PTP47, C36, PTP92 and PTP93. The N-terminal region and the C-terminal region may be from the same bacteriophage to provide a homologous tail fibre protein. Alternatively, the N-terminal region and the C-terminal region may be from different bacteriophage tail fibre proteins to provide a heterologous tail fibre protein. In one arrangement where the phage tail fibre protein is homologous, each tail fibre protein is from a bacteriophage selected from Phi33, LBL3, SPM-1, F8, PB1, KPP12, LMA2, SN, 14-1, JG024, NH-4, PTP47, C36, PTP92 and PTP93.

It is advantageous to identify phage tail fibre proteins which share sequence identity of greater than 90% in the N-terminal region. For example several phage—Phi33, PTP47, PTP92 and C36—with a broad host range for *P. aeruginosa* strains (all of these phage infect >60%, when analysed against 260 strains), have been isolated/identified and their genomes sequenced. Analysis of the genome sequences of Phi33, PTP47, PTP92 and C36 reveals that they contain genes encoding putative tail fibre proteins with a high level of sequence identity in the N-terminal region (>95% amino acid sequence identity), following a 2 sequence BLAST alignment, compared to the Phi33 tail fibre amino acids 1-628 (amino acid identity in parentheses): C36 (96%), PTP47 (98%), PTP92 (97%). BLAST searches have shown that these 4 phages are related to 10 other deposited phage genome sequences which, together, form the family of PB1-like phage: PB1, SPM1, F8, LBL3, KPP12, LMA2, SN, JG024, NH-4, 14-1 (Ceyssens et al., 2009). The homology of these putative tail fibre proteins was assessed. Following a 2 sequence BLAST alignment, compared to the Phi33 tail fibre protein (amino acid identity in parentheses): LBL3 (96%), SPM-1 (95%), F8 (95%), PB1 (95%), KPP12 (94%), LMA2 (94%), SN (87%), 14-1 (86%), JG024 (83%), NH-4 (83%), C36 (96%), PTP47 (86%), PTP92 (83%). An alignment of all 14 of the aforementioned phage is shown in FIGS. 14A-14E.

Analysis of the annotated tail fibre protein sequences from these 14 phages reveals that the N-terminal region of the proteins—equivalent to Phi33 tail fibre amino acids 1-628—show an even higher level of sequence identity at the amino acid level than the sequence identity of these proteins over their entire length, in the range of 96-100% for all 14 proteins. Following a 2 sequence BLAST alignment, compared to the N-terminal amino acids 1-628 of the Phi33 tail fibre protein (amino acid identity in parentheses): LBL3 (96%), SPM-1 (96%), F8 (96%), PB1 (96%), KPP12 (98%), LMA2 (99%), SN (99%), 14-1 (97%), JG024 (97%), NH-4 (97%), PTP47 (98%), C36 (96%), PTP92 (97%). However, the C-terminal region of the protein—equivalent to Phi33 tail fibre amino acids 629-964—is not as conserved as the N-terminal region in some of the proteins, the range of sequence identity being typically 57-96%. Following a 2 sequence BLAST alignment, compared to the C-terminal 629-964 amino acids of the Phi33 tail fibre protein (amino acid identity in parentheses): LBL3 (94%), SPM-1 (93%), F8 (93%), PB1 (94%), KPP12 (87%), LMA2 (85%), SN (65%), 14-1 (65%), JG024 (57%), NH-4 (57%), PTP47 (64%), C36 (96%), PTP92 (57%). Analysis of phage tail fibres from other, well characterised, phage has shown that they possess an N-terminal tail base plate binding region and a C-terminal receptor binding region (Veesler and Cambillau, 2011). In experimental analysis of their bacterial strain host range, using plaque assay or growth inhibition tests, the phage Phi33, PTP47, PTP92 and C36 have overlapping but non-identical host range (Table 1). Taken together with the established evidence for the role of the C-terminal region of phage tail fibres being involved in bacterial host receptor binding, and the sequence variation in the C-terminal region of these 4 phage, and their similar but non-identical host range, it is postulated that the C-terminal variation is associated with host range in the phage assessed.

It is further provided, according to this invention, that the genes for homologous tail fibre proteins can be taken from one phage and added to another, based upon their high level of sequence identity in the N-terminal region. The N-terminal region is thought to be involved in the binding of the tail fibre to the phage tail (Veesler and Cambillau, 2011), allowing the formation of viable phage with the host range associated with donor phage's tail fibre. Alternatively hybrid tail fibre genes may be made, carrying the conserved N-terminal tail attachment region of the tail fibre from a recipient phage, together with the variable C-terminal receptor-binding region from a heterologous donor phage tail fibre protein, using tail fibres genes such as those described herein. Such tail fibre hybrid genes could be used to replace some of the tail fibres of the phage. This provides an N-terminal region of the hybrid tail fibre (from the recipient phage) and allows the formation of viable phage with the host range associated with donor phage's tail fibre C-terminal receptor-binding region. Transplantation of engineered tail fibre hybrid genes into a recipient phage has been demonstrated in the present invention. Using standard molecular genetic techniques, Phi33 has been modified to carry heterologous tail fibre hybrids from the following phage: PTP92, PTP47, LBL3, SPM-1, F8, PB1, KPP12, LMA2, SN, 14-1, NH-4. All modified phage have been shown to be viable and able to plaque on P. aeruginosa. (The nomenclature of tail fibre hybrids is as follows: As an example, a hybrid gene such that the N-terminal tail attachment region of Phi33 is hybridised with the C-terminal receptor binding region of PTP47 is Phi33(N)PTP47(C).)

In one such modified phage, Phi33 was engineered such that its tail fibre gene carries the C-terminal receptor binding region of PTP92, creating PTP93 (Phi33(N)PTP92(C)). This was assessed in more detail, by testing the host range against 35 diverse P. aeruginosa clinical isolates. Comparing host range of the progenitor phage (Phi33), the tail fibre donor (PTP92) and the hybrid phage (PTP93), the host range of the PTP93 hybrid phage is equivalent to that of the tail fibre donor phage (PTP92) rather than Phi33, but it was surprisingly found that in some instances PTP93 possesses the host range of Phi33 on strains that PTP92 cannot infect, thus inheriting the host range of both phages (Table 2). Indeed, PTP93 possesses a broader host range (92%) than either Phi33 (74%) or PTP92 (66%) (Table 2). PTP93 is an example of an obligately lytic bacteriophage which can be considered as "extra-potent" as it possesses a characteristic above and beyond those exhibited in their unmodified state. Such extra potent phage are suitable for further modification to make SASPject vectors.

A preferred approach according to the present invention is to use one or more obligately lytic phage engineered to express 2 or more host range determinants (extra potent obligately lytic phage), each engineered to carry a SASP gene expressed from a constitutive promoter, each phage being genetically identical other than carrying different tail fibre genes, or tail fibre hybrid genes, and whereby a lytic gene(s) is inactivated. Such phage may be propagated in strains carrying the deleted lytic gene in trans. Preferred obligately lytic phages for modification and for provision of tail fibre genes to create phages carrying multiple tail fibre genes or tail fibre hybrid genes are phages carrying tail fibre genes which encode predicted proteins that possess ≥90% amino acid sequence identity in their N-terminal regions compared to N-terminal regions of the tail fibre of other isolated or identified phage. Preferred obligate lytic phage meeting this criterion are Phi33, PTP92, PTP47, LBL3, SPM-1, F8, PB1, KPP12, LMA2, SN, 14-1, NH-4, PTP93, JG024, PTP47 and C36. Such phage can be identified by a simple PCR assay, by subjecting plaques of isolated phage to PCR with primers specific to highly conserved regions in the N-terminal region of the tail genes. In such a way, suitable phage can be identified without whole genome sequencing. Phage PB1 can be obtained from a public strain collection. Phages need not be isolated or provided in order to generate tail fibre sequences as such sequences may be identified in DNA sequence databases, or other sources of DNA sequences, which may provide the information necessary in order to synthesise and clone, by standard methods, such sequences, or to create hybrid tail fibre sequences.

Particularly preferred phage for modification are PTP92, PTP93, Phi33, PTP47 and C36. Particularly preferred extra-potent obligate lytic phage are PTP93, modified to carry the tail fibre from Phi33 and/or the tail fibre hybrid Phi33(N)PTP47(C), and Phi33 modified to carry the hybrid tail fibre Phi33(N)PTP47(C). A particularly preferred extra-potent non-lytic SASPject derivative of PTP93 is: PTP93 carrying the Phi33 tail fibre gene and the Phi33(N)PTP47(C) tail fibre hybrid gene, carrying SASP-C from Bacillus megaterium under the control of the P. aeruginosa ribosomal subunit protein S2 (rpsB) gene promoter, in place of the endolysin gene.

A mixture of different modified bacteriophage as described above may also be provided. Mixtures of modified extra-potent non-lytic obligately lytic SASPject vectors may be used. A particularly preferred mixture of such SASPjects is: PTP93 carrying the Phi33 tail fibre gene, carrying SASP-C from Bacillus megaterium under the control of the P. aeruginosa ribosomal subunit protein S2 (rpsB) gene promoter in place of the endolysin gene, together with PTP93 carrying the Phi33(N)PTP47(C) tail fibre hybrid gene, carrying SASP-C from Bacillus megaterium under the control of the P. aeruginosa ribosomal subunit protein S2 (rpsB) gene promoter in place of the endolysin gene, together with Phi33 modified to carry the hybrid tail fibre Phi33(N)PTP47(C) carrying SASP-C from Bacillus megaterium under the control of the P. aeruginosa ribosomal subunit protein S2 (rpsB) gene promoter in place of the endolysin gene.

The host range of one such modified phage (PTP213) is shown in Table 3. PTP93 carrying the Phi33 tail fibre gene, carrying SASP-C from Bacillus megaterium under the control of the P. aeruginosa ribosomal subunit protein S2 (rpsB) gene promoter in place of the endolysin gene (PTP213) shows activity against a broader range of strains than either Phi33 or PTP92.

In another embodiment, an obligately lytic phage engineered to carry a SASP gene expressed from a constitutive promoter, in place of or inactivating a lytic gene, may be propagated in a host strain carrying the gene(s) for heterologous tail fibre protein(s) or hybrid tail fibre protein(s) in trans under the control of a suitable promoter, and the lytic gene in trans expressed from a suitable promoter. Suitable promoters for the tail fibre or tail fibre hybrid gene(s) may be a phage promoter, particularly the promoter which drives expression of the tail fibre gene in the engineered obligately lytic phage. Other suitable promoters are inducible promoters, such as lac, and trp, together with their cognate regulatory proteins. Suitable promoters for the lytic gene may be a phage promoter, particularly the promoter which usually drives expression of the lytic gene in the engineered obligately lytic phage. Other suitable promoters are inducible promoters, such as lac, and trp, together with their cognate regulatory proteins. The SASPject progeny obtained from such strains are extra-potent and non-lytic, carrying the tail fibre(s) or tail fibre hybrid(s) expressed from the strain in trans as well as their own. Alternatively the tail fibre gene from the obligately lytic phage may be deleted altogether, providing that a strain is used for propagation in which tail fibre gene(s) or tail fibre hybrid gene(s) are expressed in trans, and the lytic gene is expressed in trans, allowing for the formation of derivative SASPjects. In such an instance, the SASPject progeny from such a strain would carry multiple tail fibres, yet would lack in their genomes any tail fibre or tail fibre hybrid gene(s).

In a further aspect, the present invention provides a composition for inhibiting or preventing bacterial cell growth, which comprises a modified bacteriophage or mixtures thereof as defined herein and a carrier therefor. The modified bacteriophage may be provided in a mixture with at least one other modified bacteriophage which is capable of infecting target bacteria, which includes a SASP gene encoding a SASP which is toxic to the target bacteria and which is non-lytic. The at least one other modified bacteriophage may or may not express a plurality of different HRDs. Such compositions may have a wide range of uses and are therefore to be formulated according to the intended use. The composition may be formulated as a medicament, especially for human treatment and may treat various conditions, including bacterial infections. Among those infections treatable according to the present invention are localised tissue and organ infections, or multi-organ infections, including blood-stream infections, topical infections, oral infections including dental carries, respiratory infections, and eye infections. The carrier may be a pharmaceutically-acceptable recipient or diluent. The exact nature and quantities of the components of such compositions may be determined empirically and will depend in part upon the routes of administration of the composition.

Routes of administration to recipients include intravenous, intra-arterial, oral, buccal, sublingual, intranasal, by inhalation, topical (including ophthalmic), intra-muscular, subcutaneous and intra-articular. For convenience of use, dosages according to the invention will depend on the site and type of infection to be treated or prevented. Respiratory infections may be treated by inhalation administration and eye infections may be treated using eye drops. Oral hygiene products containing the modified bacteriophage are also provided; a mouthwash or toothpaste may be used which contains modified bacteriophage according to the invention formulated to eliminate bacteria associated with dental plaque formation.

A modified bacteriophage according to the invention may be used as a bacterial decontaminant, for example in the treatment of surface bacterial contamination as well as land remediation or water treatment. The bacteriophage may be used in the treatment of medical personnel and/or patients as a decontaminating agent, for example in a handwash. Treatment of work surfaces and equipment is also provided, especially that used in hospital procedures or in food preparation. One particular embodiment comprises a composition formulated for topical use for preventing, eliminating or reducing carriage of bacteria and contamination from one individual to another. This is important to limit the transmission of microbial infections, particularly in a hospital environment where bacteria resistant to conventional antibiotics are prevalent. For such a use the modified bacteriophage may be contained in Tris buffered saline or phosphate buffered saline may be formulated within a gel or cream. For multiple use a preservative may be added. Alternatively the product may be lyophilised and excipients, for example a sugar such as sucrose may be added.

DETAILED DESCRIPTION OF THE INVENTION

The invention will now be described in further detail, by way of example only, with reference to the accompanying figures and the following Examples.

FIGS. 10A-10C are a schematic diagram showing genetic modification of phage carrying three tail fibre genes, utilising a lacZα marker, and then to replace endolysin with rpsB-SASP-C, also utilising a lacZα marker;

FIGS. 12A-12C are a schematic diagram showing production of bacteriophage that carry multiple tail fibre genes or tail fibre hybrid genes, and in which the endolysin gene has been replaced with rpsB-SASP-C, according to the invention;

Figure 13A:
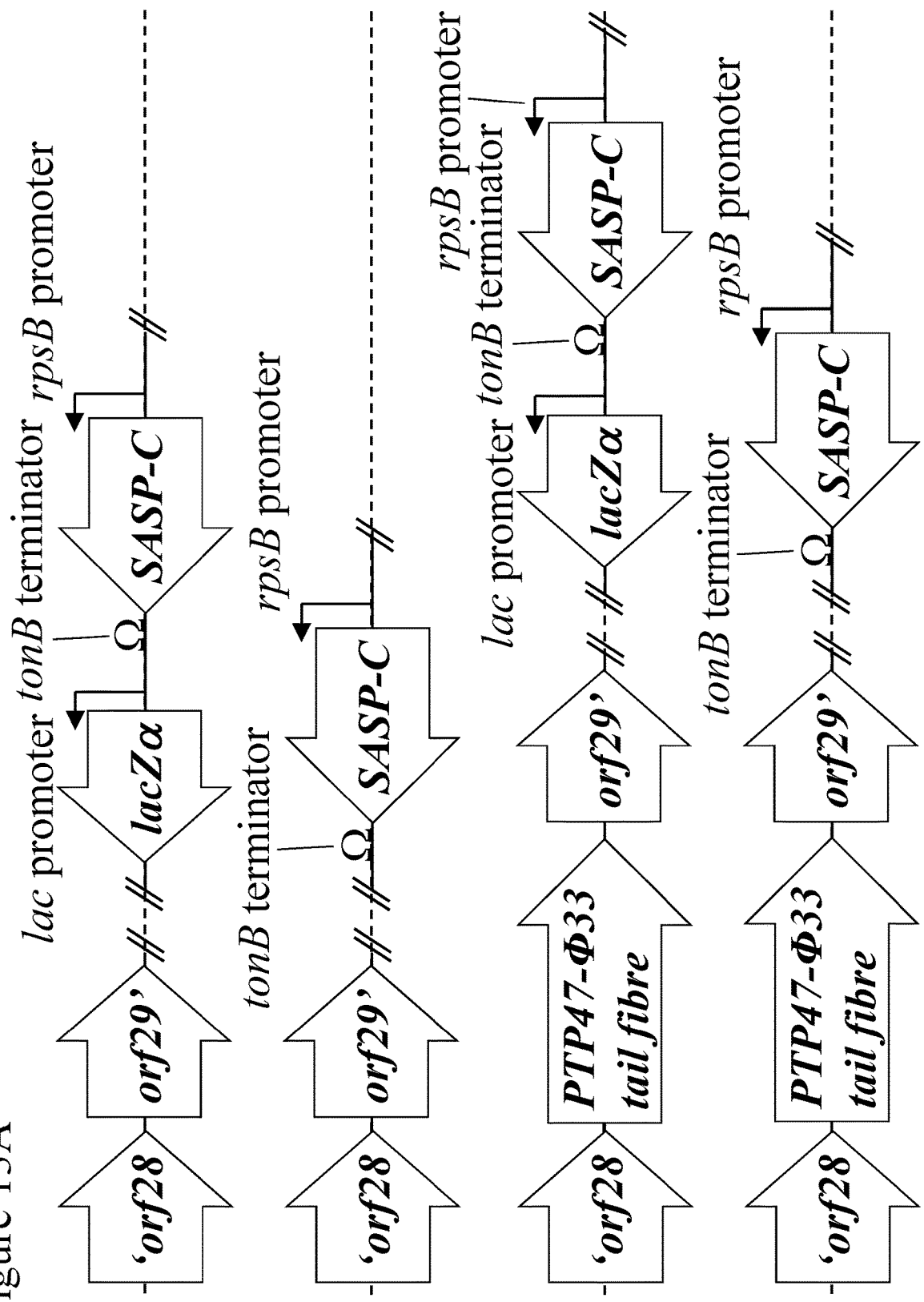
Figure 13B:
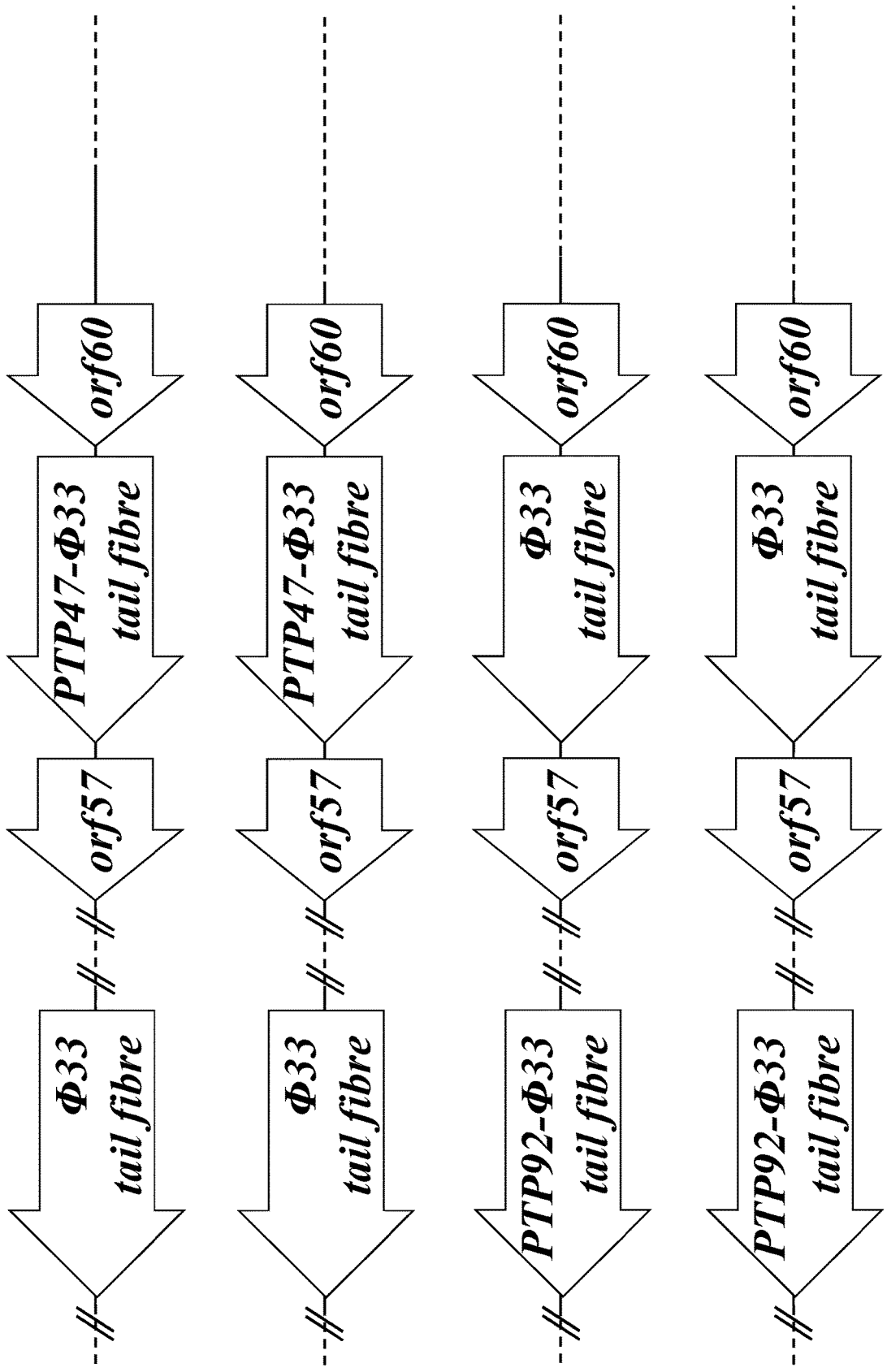
Figure 13C:
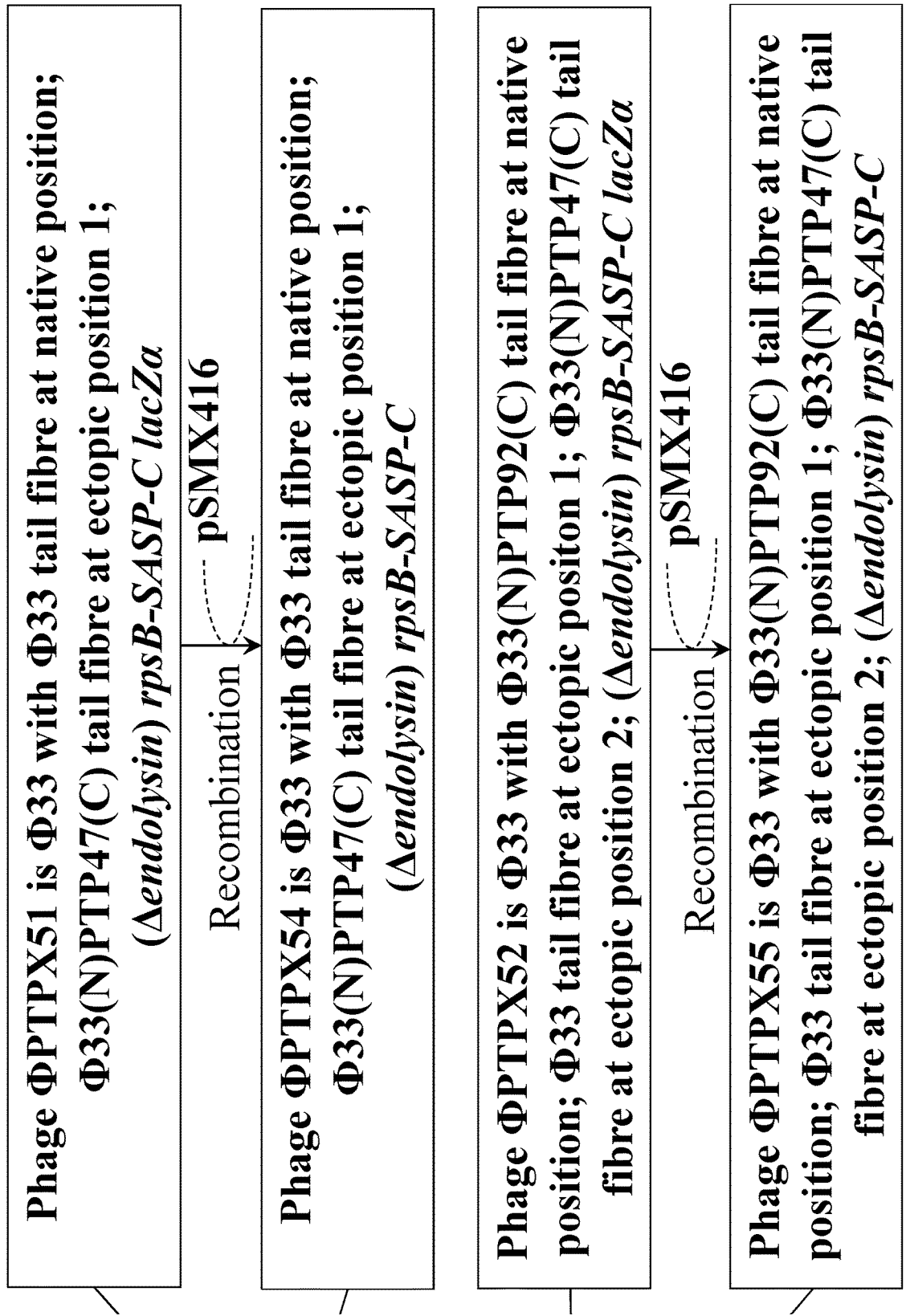

FIGS. 13A-13C are a schematic diagram showing production of further bacteriophage that carry multiple tail fibre genes or tail fibre hybrid genes, and in which the endolysin gene has been replaced with rpsB-SASP-C, according to the invention; and FIGS. 14A-14E are a multiple sequence alignment of tail fibre genes from related phages. Shown is a CLUSTAL 2.1 multiple sequence alignment of the tail fibre genes from Phage SPM-1, F8, PB1, C36, LBL3, Phi33, LMA2, KPP12, JG024, PTP92, NH-4, 14-1, PTP47, SN. Sequence divergent C-terminal region shaded in grey, sequence conserved N-terminal region unshaded.

GENERIC PRODUCT COVERING MULTIPLE TAIL FIBRES WITHIN AN INDIVIDUAL PHAGE, OR A MIX OF PHAGES EACH CONTAINING MULTIPLE TAIL FIBRES

Summary of the genetic modification of a lytic bacteriophage to render it non-lytic, and such that it carries more than one tail fibre gene, in addition to SASP-C under the control of a promoter that usually controls expression of the 30S ribosomal subunit protein S2 gene (rpsB).

Genes can be removed and added to the phage genome using homologous recombination. There are several ways in which phages carrying foreign genes and promoters can be constructed and the following is an example of such methods.

For the construction of Phi33 derivatives, it is shown how, using an E. coli/P. aeruginosa broad host range vector, as an example only, Phi33-based bacteriophage carrying alternative tail fibre genes may be made, via homologous recombination. It is also shown how Phi33 derivatives may be constructed, using an E. coli/P. aeruginosa broad host range vector, as an example only, in which an additional tail fibre gene is added to the bacteriophage genome via homologous recombination, such that the resulting bacteriophage carry two tail fibre genes. In a subsequent step, it is shown how, using an E. coli/P. aeruginosa broad host range vector, as an example only, a third tail fibre gene may be added to the bacteriophage genome via homologous recombination, such that the resulting bacteriophage carry three tail fibre genes.

As an example, for the construction of recombinant lytic bacteriophage, an E. coli lacZα marker may be included as a means of identifying recombinant bacteriophage. In order to use this marker, the bacteriophage host strains must first be modified to carry the E. coli lacZΔM15 allele at a suitable location in the bacterial genome, to complement the lacZα phenotypes of the desired recombinant bacteriophage. As an example, the construction of this P. aeruginosa strain may be achieved via homologous recombination using an E. coli vector that is unable to replicate in P. aeruginosa. The genomic location for insertion of the lacZΔM15 transgene should be chosen such that no essential genes are affected and no unwanted phenotypes are generated through polar effects on the expression of adjacent genes. As an example, one such location may be immediately downstream of the P. aeruginosa strain PAO1 phoA homologue.

The E. coli lacZΔM15 allele may be cloned into an E. coli vector that is unable to replicate in P. aeruginosa, between two regions of P. aeruginosa strain PAO1 genomic DNA that flank phoA. This plasmid may be introduced into P. aeruginosa and isolates having undergone a single homologous recombination to integrate the whole plasmid into the genome selected according to acquisition of tetracycline (50 µg/ml) resistance. Isolates which have undergone a second homologous recombination event may then be isolated on medium containing 10% sucrose (utilising the sacB counterselectable marker that is present on the plasmid backbone).

As an example by which Phi33 derivatives may be made that possess an alternative tail fibre gene, a tail fibre gene comprising the region encoding the N-terminal region of the Phi33 tail fibre, followed by the region encoding the C-terminal, receptor-binding region of the tail fibre from phage PTP92 (Phi33(N)PTP92(C)), may be constructed, and cloned next to a lacZα marker, in between two regions of homology that flank the native tail fibre gene of Phi33. This plasmid may be introduced into P. aeruginosa, and the resulting strain infected with Phi33. Following harvesting of progeny phage, double recombinants may be isolated by plaquing on a suitable P. aeruginosa (lacZΔM15⁺) host, using medium containing S-gal as a chromogenic indicator of β-galactosidase activity. The resulting phage will have had the native Phi33 tail fibre replaced by the gene encoding the Phi33(N)PTP92(C) tail fibre, plus a lacZα marker.

In a subsequent step, the lacZα marker may be removed from the Phi33(N)PTP92(C) tail fibre phage via another homologous recombination step. The region of homology downstream of the native Phi33 tail fibre may be cloned next to the gene encoding the C-terminal, receptor-binding region of PTP92. This plasmid may be introduced into a suitable P. aeruginosa strain, and the resulting strain infected with the Phi33 derivative carrying the gene encoding the Phi33(N) PTP92(C) tail fibre, plus lacZα. Following harvesting of progeny phage, double recombinants may be isolated by plaquing on a suitable P. aeruginosa (lacZΔM15⁺) host, using medium containing S-gal as a chromogenic indicator of β-galactosidase activity. The resulting Phi33 derivative (PTP93) will have had the native Phi33 tail fibre replaced by the gene encoding the Phi33(N)PTP92(C) tail fibre, and will no longer carry the lacZα marker.

As an example by which tail fibre genes may be added to a bacteriophage genome, the tail fibre gene from bacteriophage Phi33 may be cloned next to the E. coli lacZα marker, between two regions of Phi33 DNA that flank the 5' end of orf57 (ectopic position 1; this is the beginning of the predicted operon containing the native tail fibre gene), in a broad host range E. coli/P. aeruginosa vector. This plasmid may be introduced into P. aeruginosa, and the resulting strain infected with PTP93. Following harvesting of progeny phage, double recombinants may be isolated by plaquing on a suitable P. aeruginosa (lacZΔM15⁺) host, using medium containing S-gal as a chromogenic indicator of β-galactosidase activity. The resulting phage will contain two tail fibre genes: the gene encoding the Phi33(N)PTP92(C) tail fibre at the native position and the gene encoding the native Phi33 tail fibre (plus a lacZα marker) at an ectopic position (ectopic position 1).

In an alternative example, a gene encoding a tail fibre comprising the N-terminal region of the Phi33 tail fibre and the C-terminal receptor-binding region of the tail fibre from bacteriophage PTP47 (Phi33(N)PTP47(C)), may be constructed and cloned next to the E. coli lacZα marker, between two regions of Phi33 DNA that flank the 5' end of orf57 (ectopic position 1; this is the beginning of the predicted operon containing the native tail fibre gene), in a broad host range E. coli/P. aeruginosa vector. This plasmid may be introduced into P. aeruginosa, and the resulting strain infected with PTP93. Following harvesting of progeny phage, double recombinants may be isolated by plaquing on a suitable P. aeruginosa (lacZΔM15⁺) host, using medium containing S-gal as a chromogenic indicator of β-galactosidase activity. The resulting phage will contain two tail fibre genes: the gene encoding the Phi33(N)PTP92(C) tail fibre at the native position and the gene encoding the Phi33(N) PTP47(C) tail fibre (plus a lacZα marker) at an ectopic position (ectopic position 1).

In an alternative example, a gene encoding a tail fibre comprising the N-terminal region of the Phi33 tail fibre and the C-terminal receptor-binding region of the tail fibre from bacteriophage PTP47 (Phi33(N)PTP47(C)), may be constructed and cloned next to an E. coli lacZα marker, between two regions of Phi33 DNA that flank orf57 (ectopic position 1; this is the beginning of the predicted operon containing the native tail fibre gene), in a broad host range E. coli/P. aeruginosa vector. This plasmid may be introduced into P. aeruginosa, and the resulting strain infected with Phi33. Following harvesting of progeny phage, double recombinants may be isolated by plaquing on a suitable P. aeruginosa (lacZΔM15$^+$) host, using medium containing S-gal as a chromogenic indicator of β-galactosidase activity. The resulting phage will contain two tail fibre genes: the gene encoding the Phi33 native tail fibre at the native position and the gene encoding the Phi33(N)PTP47(C) tail fibre (plus a lacZα marker) at an ectopic position (ectopic position 1).

In subsequent steps, the lacZα marker may be removed from these Phi33 derivatives by another homologous recombination step. The lacZα marker may be deleted from the previously-described recombination plasmids that were used to introduce the gene encoding the Phi33 native tail fibre, or the Phi33(N)PTP47(C) tail fibre at ectopic position 1. These ΔlacZα plasmids may be introduced into suitable P. aeruginosa strains, and the resulting strains infected, as appropriate, with Phi33 derivatives carrying either the wild type Phi33 tail fibre gene plus the lacZα marker, or the gene encoding the Phi33(N)PTP47(C) tail fibre plus the lacZα marker, at ectopic position 1. Following harvesting of progeny phage, double recombinants may be isolated by plaquing on a suitable P. aeruginosa (lacZΔM15$^+$) host, using medium containing S-gal as a chromogenic indicator of β-galactosidase activity. The resulting Phi33 derivatives will contain two tail fibre genes (Phi33(N)PTP92(C) at the native position and Phi33 native tail fibre at ectopic position 1, OR Phi33(N)PTP92(C) at the native position and Phi33(N)PTP47(C) at ectopic position 1, OR Phi33 native tail fibre at the native position and Phi33(N)PTP47(C) at ectopic position 1), and will no longer carry the lacZα marker.

In a subsequent step, another homologous recombination may be used to add a third tail fibre gene to the bacteriophage genome. As an example, a gene encoding a tail fibre comprising the N-terminal region of the Phi33 tail fibre and the C-terminal receptor-binding region of the tail fibre from bacteriophage PTP47, under the control of the native tail fibre promoter (orf57 promoter), may be constructed and cloned next to a lacZα marker, between two regions of Phi33 DNA that flank an intergenic region between orf28 and orf29 (ectopic position 2), in a broad host range E. coli/P. aeruginosa vector. This plasmid may be introduced into P. aeruginosa, and the resulting strain infected with Phi33 carrying the gene encoding the Phi33(N)PTP92(C) tail fibre at the native position and the gene encoding the native Phi33 tail fibre at ectopic position 1 (ΔlacZα). Following harvesting of progeny phage, double recombinants may be isolated by plaquing on a suitable P. aeruginosa (lacZΔM15$^+$) host, using medium containing S-gal as a chromogenic indicator of β-galactosidase activity. The resulting phage will contain three tail fibre genes: the gene encoding the Phi33(N)PTP92 (C) tail fibre at the native position, the native Phi33 tail fibre gene at ectopic position 1, and the gene encoding the Phi33(N)PTP47(C) tail fibre (plus a lacZα marker) at ectopic position 2.

In a subsequent step, the lacZα marker may be removed from this Phi33 derivative carrying three tail fibre genes (the gene encoding the Phi33(N)PTP92(C) tail fibre at the native locus, the native Phi33 tail fibre gene at ectopic position 1, and the gene encoding the Phi33(N)PTP47(C) tail fibre, plus the lacZα marker, at ectopic position 2) by another homologous recombination step. The lacZα marker may be deleted from the previously-described recombination plasmid used to introduce the gene encoding the Phi33(N)PTP47(C) tail fibre at ectopic position 2. This ΔlacZα plasmid may be introduced into a suitable P. aeruginosa strain, and the resulting strain infected with the Phi33 derivative carrying the gene encoding the Phi33(N)PTP92(C) tail fibre at the native locus, the native Phi33 tail fibre gene at ectopic position 1, and the gene encoding the Phi33(N)PTP47(C) tail fibre, plus the lacZα marker, at ectopic position 2. Following harvesting of progeny phage, double recombinants may be isolated by plaquing on a suitable P. aeruginosa (lacZΔM15$^+$) host, using medium containing S-gal as a chromogenic indicator of β-galactosidase activity. The resulting phage will contain three tail fibre genes: the gene encoding the Phi33(N)PTP92(C) tail fibre at the native position, the native Phi33 tail fibre gene at ectopic position 1, and the gene encoding the Phi33(N)PTP47(C) tail fibre at ectopic position 2, and will no longer carry the lacZα marker.

In subsequent steps, a similar homologous recombination may be used to replace the endolysin gene of any of the Phi33 derivatives, or similar bacteriophage, with the gene for SASP-C, under the control of a P. aeruginosa rpsB promoter, while simultaneously adding the E. coli lacZα marker for the identification of recombinant phage. Since the bacteriophage to be modified is lytic (rather than temperate), another requirement for this latter step of bacteriophage construction is the construction of a derivative of a P. aeruginosa host strain that carries the Phi33 endolysin gene and the E. coli lacZΔM15 allele at a suitable location in the bacterial genome, to complement the Δendolysin and lacZα phenotypes of the desired recombinant bacteriophage. As an example, the construction of this P. aeruginosa strain may be achieved via homologous recombination using an E. coli vector that is unable to replicate in P. aeruginosa. The genomic location for insertion of the endolysin and lacZΔM15 transgenes should be chosen such that no essential genes are affected and no unwanted phenotypes are generated through polar effects on the expression of adjacent genes. As an example, one such location may be immediately downstream of the P. aeruginosa strain PAO1 phoA homologue.

The Phi33 endolysin gene and the E. coli lacZΔM15 allele may be cloned into an E. coli vector that is unable to replicate in P. aeruginosa, between two regions of P. aeruginosa strain PAO1 genomic DNA that flank phoA. This plasmid may be introduced into P. aeruginosa and isolates having undergone a single homologous recombination to integrate the whole plasmid into the genome selected according to acquisition of tetracycline (50 μg/ml) resistance. Isolates which have undergone a second homologous recombination event may then be isolated on medium containing 10% sucrose (utilising the sacB counter-selectable marker that is present on the plasmid backbone).

A region consisting of SASP-C controlled by the rpsB promoter, and the E. coli lacZα allele, may be cloned between two regions of Phi33 that flank the endolysin gene, in a broad host range E. coli/P. aeruginosa vector. This plasmid may be transferred to the previously constructed P. aeruginosa (endolysin$^+$ lacZΔM15$^+$) strain, and the resulting strain infected by any of the Phi33 derivatives that have already been genetically modified to carry more than one tail fibre gene, as exemplified above in the previous steps. Progeny phage may be harvested and double recombinants identified by plaquing on P. aeruginosa (endolysin$^+$ lacZΔM15$^+$), looking for acquisition of the lacZα reporter on medium containing a chromogenic substrate that detects the action of β-galactosidase.

In a subsequent step, the lacZα marker may be removed from the previously-constructed phage that carry rpsB-SASP-C and lacZα in place of the endolysin gene, by homologous recombination. A region consisting of rpsB-SASP-C may be cloned in between two regions of homology that flank the Phi33 endolysin gene, in a broad host range *E. coli/P. aeruginosa* vector. This plasmid may be transferred to the previously constructed *P. aeruginosa* (endolysin⁺ lacZΔM15⁺) strain, and the resulting strain infected by any of the Phi33 derivatives that have already been genetically modified to carry rpsB-SASP-C in place of the endolysin gene, as exemplified above in the previous steps. Progeny phage may be harvested and double recombinants identified by plaquing on *P. aeruginosa* (endolysin⁺ lacZΔM15⁺), looking for loss of the lacZα reporter on medium containing a chromogenic substrate that detects the action of β-galactosidase. The resulting phage will carry multiple tail fibre or tail fibre hybrid genes, and carry rpsB-SASP-C in place of endolysin, according to the invention.

Experimental Procedures

PCR reactions to generate DNA for cloning purposes may be carried out using Herculase II Fusion DNA polymerase (Agilent Technologies), depending upon the melting temperatures ($T_m$) of the primers, according to manufacturers instructions. PCR reactions for screening purposes may be carried out using Taq DNA polymerase (NEB), depending upon the $T_m$ of the primers, according to manufacturers instructions. Unless otherwise stated, general molecular biology techniques, such as restriction enzyme digestion, agarose gel electrophoresis, T4 DNA ligase-dependent ligations, competent cell preparation and transformation may be based upon methods described in Sambrook et al., (1989). Enzymes may be purchased from New England Biolabs or Thermo Scientific. DNA may be purified from enzyme reactions and prepared from cells using Qiagen DNA purification kits. Plasmids may be transferred from *E. coli* strains to *P. aeruginosa* strains by conjugation, mediated by the conjugation helper strain *E. coli* HB101 (pRK2013). A chromogenic substrate for β-galactosidase, S-gal, that upon digestion by β-galactosidase forms a black precipitate when chelated with ferric iron, may be purchased from Sigma (S9811).

Primers may be obtained from Sigma Life Science. Where primers include recognition sequences for restriction enzymes, additional 2-6 nucleotides may be added at the 5' end to ensure digestion of the PCR-amplified DNA.

All clonings, unless otherwise stated, may be achieved by ligating DNAs overnight with T4 DNA ligase and then transforming them into *E. coli* cloning strains, such as DH5α or TOP10, with isolation on selective medium, as described elsewhere (Sambrook et al., 1989).

An *E. coli/P. aeruginosa* broad host range vector, such as pSM1080, may be used to transfer genes between *E. coli* and *P. aeruginosa*. pSM1080 was previously produced by combining a broad host-range origin of replication to allow replication in *P. aeruginosa*, oriT from pRK2, the tetAR selectable marker for use in both *E. coli* and *P. aeruginosa*, from plasmid pRK415, and the high-copy-number, *E. coli* origin of replication, oriV, from plasmid pUC19.

An *E. coli* vector that is unable to replicate in *P. aeruginosa*, pSM1104, may be used to generate *P. aeruginosa* mutants by allelic exchange. pSM1104 was previously produced by combining oriT from pRK2, the tetAR selectable marker for use in both *E. coli* and *P. aeruginosa*, from plasmid pRK415, the high-copy-number, *E. coli* origin of replication, oriV, from plasmid pUC19, and the sacB gene from *Bacillus subtilis* strain 168, under the control of a strong promoter, for use as a counter-selectable marker.

Detection of Phi33-Like Phage (PB1-Like Phage Family) Conserved N-Terminal Tail Fibre Regions by PCR 1. Primers for the detection of Phi33-like phage-like tail fibre genes in experimental phage samples may be designed as follows:

The DNA sequences of the tail fibre genes from all sequenced Phi33-like phage (including Phi33, PB1, NH-4, 14-1, LMA2, KPP12, JG024, F8, SPM-1, LBL3, PTP47, C36, PTP92 and SN) may be aligned using Clustal Omega, which is available on the EBI website, and the approximately 2 kb-long highly conserved region mapping to the gene's 5' sequence may be thus identified (positions 31680-33557 in the PB1 genome sequence, Acc. EU716414). Sections of 100% identity among the 11 tail fibre gene sequences may be identified by visual inspection. Three pairs of PCR primers targeting selected absolutely conserved regions, and amplifying PCR products no longer than 1 kb may be chosen as follows: pair B4500 and B4501, defining a 194 bp-long region; pair B4502 and B4503, defining a 774 bp-long region; and pair B4504 and B4505, defining a 365 bp-long region.

Primer B4500 consists of sequence of PB1 phage genome (Acc. EU716414) ranging from position 31680 to 31697. Primer B4501 consists of sequence of PB1 phage genome (Acc. EU716414) ranging from position 31851 to 31872. Primer B4502 consists of sequence of PB1 phage genome (Acc. EU716414) ranging from position 31785 to 31804. Primer B4503 consists of sequence of PB1 phage genome (Acc. EU716414) ranging from position 32541 to 32558. Primer B4504 consists of sequence of PB1 phage genome (Acc. EU716414) ranging from position 32868 to 32888. Primer B4505 consists of sequence of PB1 phage genome (Acc. EU716414) ranging from position 33213 to 33232.

```
B4500
                                    (SEQ ID NO: 1)
    5'-GTGATCACACCCGAACTG-3'

B4501
                                    (SEQ ID NO: 2)
    5'-CGATGAAGAAGAGTTGGTTTTG-3'

B4502
                                    (SEQ ID NO: 3)
    5'-ACGCCGGACTACGAAATCAG-3'

B4503
                                    (SEQ ID NO: 4)
    5'-TCCGGAGACGTTGATGGT-3'

B4504
                                    (SEQ ID NO: 5)
    5'-CCTTTCATCGATTTCCACTTC-3'

B4505
                                    (SEQ ID NO: 6)
    5'-TTCGTGGACGCCCAGTCCCA-3'
```

2. Phi33-like tail fibre genes may be detected in experimental phage samples as follows:

Plaques of isolated phage of environmental origin may be picked from agar plates and added to water and incubated for 30 minutes, making plaque soak outs. The plaque soak outs may be diluted and a portion added to PCR reactions containing one or all of the above primer pairs, and PCR may be performed according to a standard protocol. PCR products may be visualised on a 1.5% agarose gel with ethidium bromide staining, and evaluated for their size. PCR products of the correct size for the primer pair used may be gel-extracted and submitted to an external facility for sequencing. Sequencing results may be compared with the available tail fibre gene sequences in order to confirm the identity of the PCR product.

Construction of a Plasmid to Introduce the *Escherichia coli* lacZΔM15 Allele into the Genome of *P. aeruginosa*, Downstream of phoA 1. Plasmid pSMX400 (FIGS. 1A-1C), comprising pSM1104 carrying DNA flanking the 3' end of the *P. aeruginosa* PAO1 phoA homologue, may be constructed as follows.

Figure 1A:
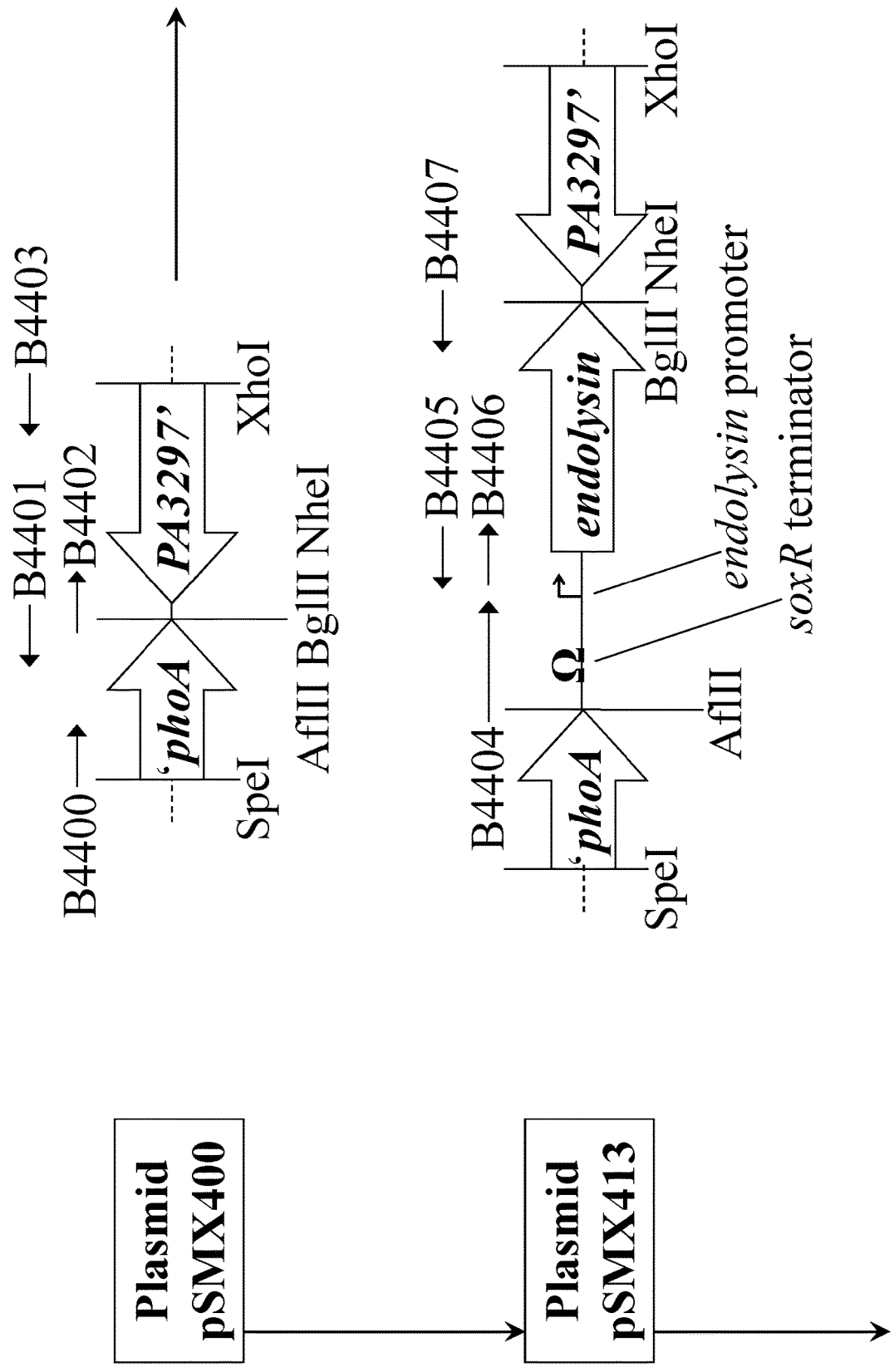
FIGS. 1A-1C are a schematic diagram showing construction of plasmids containing lacZΔM15 and the Phi33 endolysin gene for the creation of transgenic *P. aeruginosa* strains.
Figure 1B:
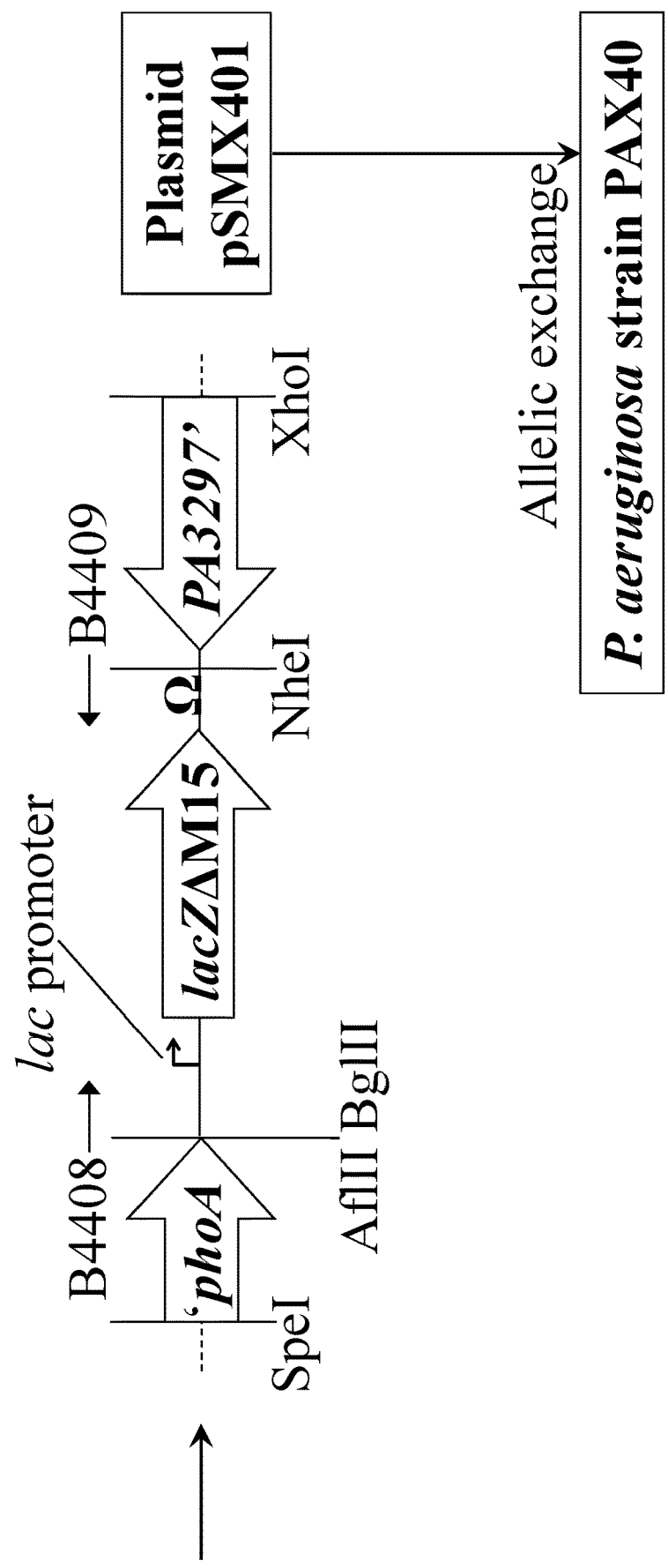
Figure 1C:
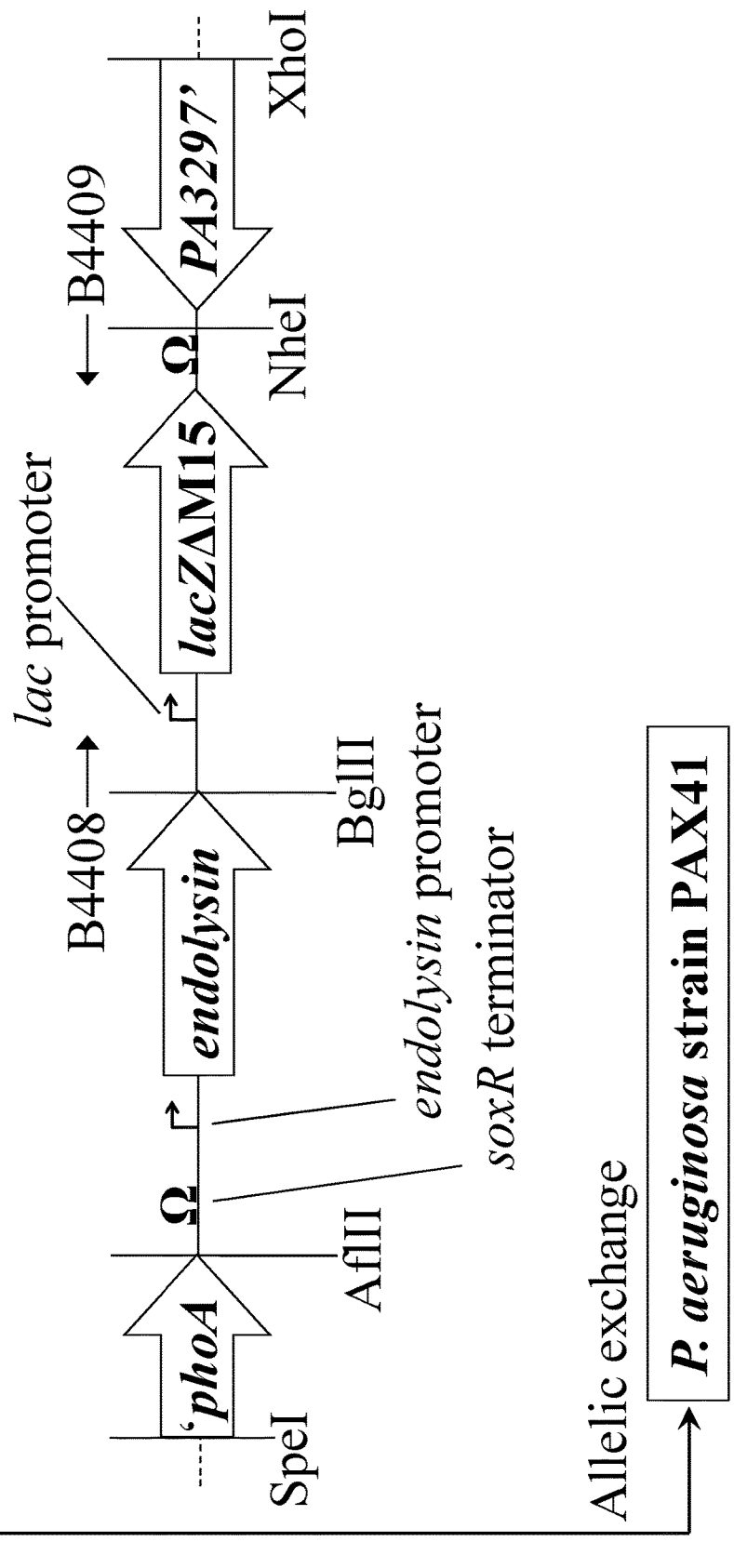

A region comprising the terminal approximately 1 kb of the phoA gene from *P. aeruginosa* may be amplified by PCR using primers B4400 and B4401 (FIGS. 1A-1C). The PCR product may then be cleaned and digested with SpeI and BglII. A second region comprising approximately 1 kb downstream of the phoA gene from *P. aeruginosa*, including the 3' end of the PA3297 open reading frame, may be amplified by PCR using primers B4402 and B4403 (FIGS. 1A-1C). This second PCR product may then be cleaned and digested with BglII and XhoI. The two digests may be cleaned again and ligated to pSM1104 that has been digested with SpeI and XhoI, in a 3-way ligation, to yield plasmid pSMX400 (FIGS. 1A-1C).

Primer B4400 consists of a 5' SpeI restriction site (underlined), followed by sequence located approximately 1 kb upstream of the stop codon of phoA from *P. aeruginosa* strain PA01 (FIGS. 1A-1C). Primer B4401 consists of 5' BglII and AflII restriction sites (underlined), followed by sequence complementary to the end of the phoA gene from *P. aeruginosa* strain PAO1 (the stop codon is in lower case; FIGS. 1A-1C). Primer B4402 consists of 5' BglII and NheI restriction sites (underlined), followed by sequence immediately downstream of the stop codon of the phoA gene from *P. aeruginosa* strain PAO1 (FIGS. 1A-1C). Primer B4403 consists of a 5' XhoI restriction site (underlined), followed by sequence within the PA3297 open reading frame, approximately 1 kb downstream of the phoA gene from *P. aeruginosa* strain PAO1 (FIGS. 1A-IC).

```
Primer B4400
                                    (SEQ ID NO: 7)
5'-GATAACTAGTCCTGGTCCACCGGGGTCAAG-3'

Primer B4401
                                    (SEQ ID NO: 8)
5'-GCTCAGATCTTCCTTAAGtcaGTCGCGCAGGTTCAG-3'

Primer B4402
                                    (SEQ ID NO: 9)
5'-AGGAAGATCTGAGCTAGCTCGGACCAGAACGAAAAAG-3'

Primer B4403
                                    (SEQ ID NO: 10)
5'-GATACTCGAGGCGGATGAACATTGAGGTG-3'
```

2. Plasmid pSMX401 (FIGS. 1A-1C), comprising pSMX400 carrying lacZΔM15 under the control of a lac promoter, may be constructed as follows.

The lacZΔM15 gene under the control of a lac promoter may be amplified by PCR from *Escherichia coli* strain DH10B using primers B4408 and B4409 (FIGS. 1A-1C). The resulting PCR product may then be digested with BglII and NheI, and ligated to pSMX400 that has also been digested with BglII and NheI, to yield plasmid pSMX401 (FIGS. 1A-1C).

Primer B4408 consists of a 5' BglII restriction site (underlined), followed by sequence of the lac promoter (FIGS. 1A-1C). Primer B4409 consists of a 5' NheI restriction site (underlined), followed by a bi-directional transcriptional terminator and sequence complementary to the 3' end of lacZΔM15 (underlined, in bold; FIGS. 1A-1C).

```
Primer B4408
                                    (SEQ ID NO: 11)
5'-GATAAGATCTGAGCGCAACGCAATTAATGTG-3'

Primer B4409
                                    (SEQ ID NO: 12)
5'-GATAGCTAGCAGTCAAAAGCCTCCGGTCGGAGGCTTTTGACTTTATT
TTTGACACCAGACCAAC-3'
```

Genetic Modification of *Pseudomonas aeruginosa* to Introduce the *Escherichia coli* lacZΔM15 Gene Immediately Downstream of the phoA Locus of the Bacterial Genome 1. Plasmid pSMX401 (FIGS. 1A-1C) may be transferred to *P. aeruginosa* by conjugation, selecting for primary recombinants by acquisition of resistance to tetracycline (50 μg/ml).

2. Double recombinants may then be selected via sacB-mediated counter-selection, by plating onto medium containing 10% sucrose.

3. Isolates growing on 10% sucrose may then be screened by PCR to confirm that lacZΔM15 has been introduced downstream of the *P. aeruginosa* phoA gene.

4. Following verification of an isolate (PAX40), this strain may then be used as a host for further modification of bacteriophage, where complementation of a lacZα reporter is required.

Construction of Plasmids for Recombination with Phi33, to Generate PTP93, Utilising a lacZα Screening Process 1. pSMX402 (FIGS. 2A-2B), comprising pSM1080 carrying the region immediately downstream of the Phi33 tail fibre gene, may be constructed as follows.

Figure 2A:
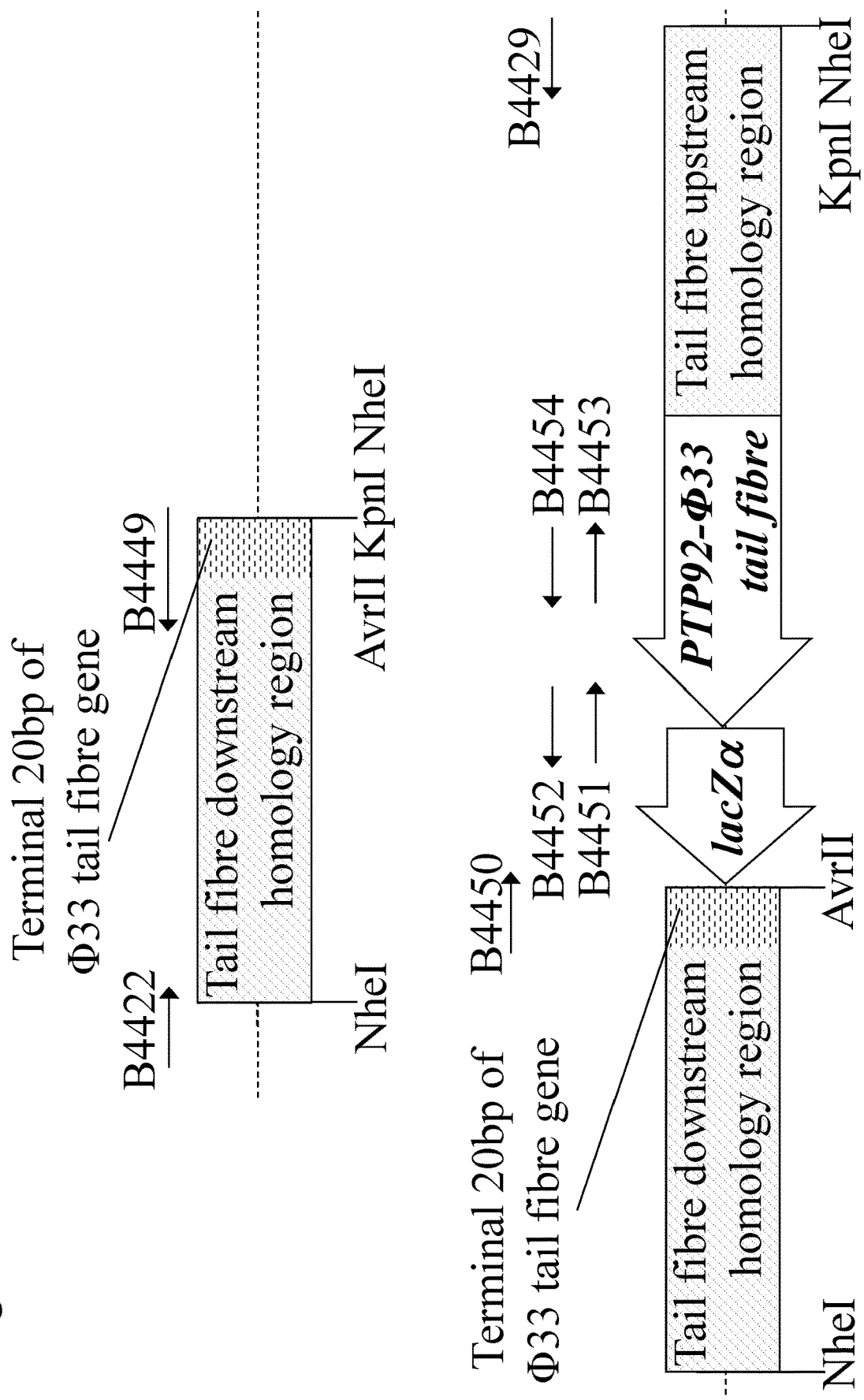
FIGS. 2A-2B are a schematic diagram showing construction of plasmids encoding hybrid tail fibre genes, including the lacZα marker.
Figure 2B:
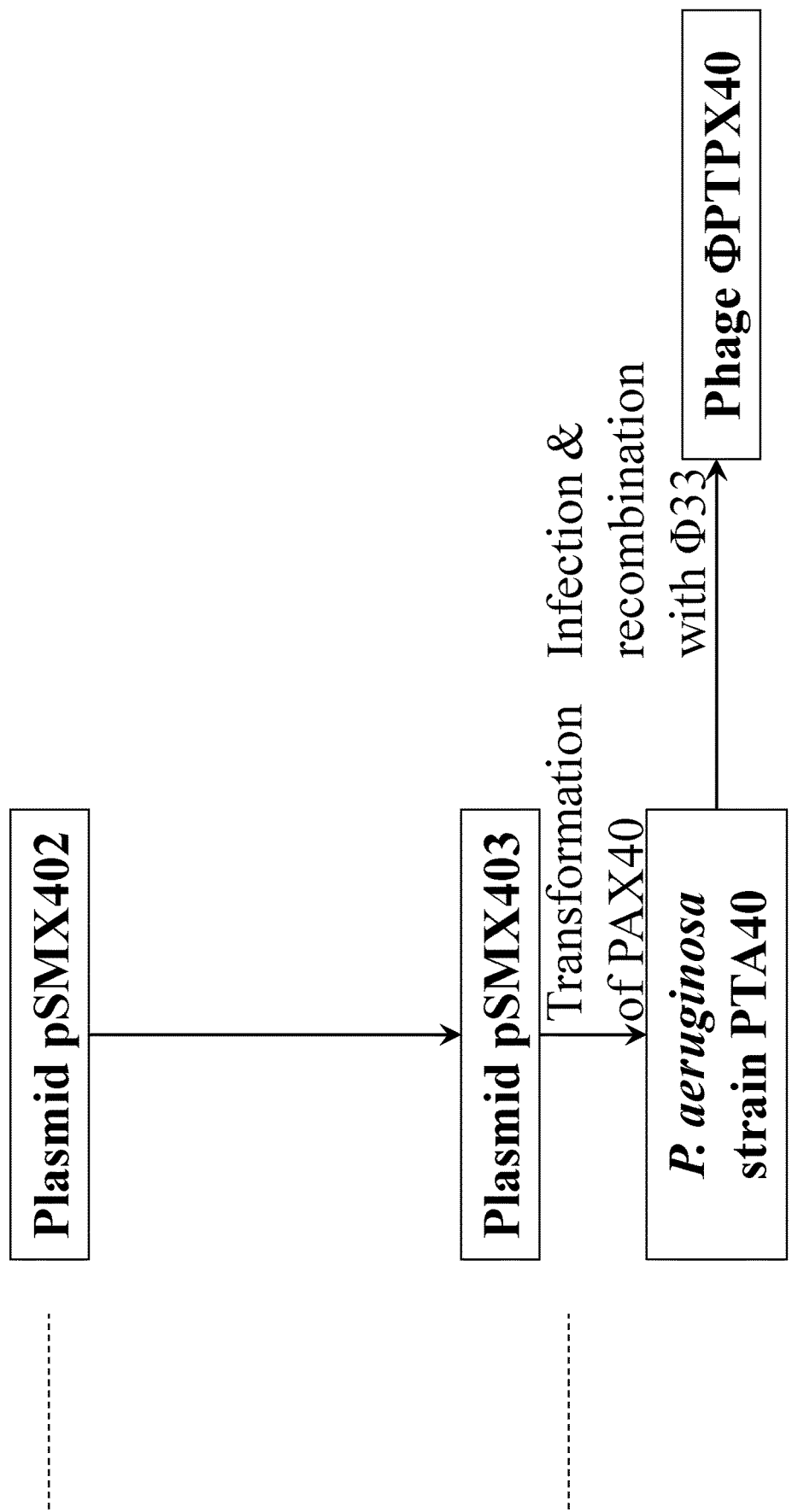

A 1 kb region of Phi33 sequence covering the terminal 20 bases of the Phi33 tail fibre, and the adjacent downstream region, may be amplified by PCR using primers B4422 and B4449 (FIGS. 2A-2B). The resulting PCR product may then be cleaned and digested with NheI, and ligated to pSM1080 that has also been digested with NheI and then treated with alkaline phosphatase prior to ligation, yielding plasmid pSMX402 (FIGS. 2A-2B).

Primer B4422 consists of a 5' NheI restriction site (underlined), followed by sequence from Phi33, approximately 1 kb downstream of the end of the Phi33 tail fibre gene (FIGS. 2A-2B). B4449 consists of 5' NheI-KpnI-AvrII restriction sites (underlined), followed by sequence complementary to the 3' end of the Phi33 tail fibre and sequence immediately downstream of the tail fibre open reading frame (FIGS. 2A-2B).

```
B4422
                                    (SEQ ID NO: 13)
5'-GATAGCTAGCATGGTTTTCACGACCATG-3'

B4449
                                    (SEQ ID NO: 14)
5'-GATAGCTAGCGAGGTACCGACCTAGGTTTTCCAGCGAGTGACGTAA
AATG-3'
```

2. pSMX403 (FIGS. 2A-2B), comprising pSMX402 carrying lacZα, a tail fibre gene consisting of a 3' section of PTP92 DNA that encodes the C-terminal receptor-binding region of the tail fibre and the 5' section of the Phi33 tail fibre gene sequence that encodes the N-terminal region, and sequence located immediately upstream of the Phi33 tail fibre gene, may be constructed as follows.

The lacZα open reading frame may be amplified by PCR from pUC19 using primers B4450 and B4452 (FIGS. 2A-2B). The region of the PTP92 tail fibre gene that encodes the C-terminal receptor-binding region, may be amplified by PCR from PTP92 using primers B4451 and B4454 (FIGS. 2A-2B). The lacZα open reading frame may then be joined to the section of PTP92 DNA that encodes the tail fibre C-terminal receptor-binding region, by SOEing PCR using the outer primers, B4450 and B4454. A region comprising sequence of Phi33 tail fibre gene that encodes the N-terminal region, and sequence located immediately upstream of the Phi33 tail fibre gene, may be amplified by PCR using primers B4453 and B4429 (FIGS. 2A-2B). This PCR product may then be joined to the PCR product comprising lacZα and the PTP92 tail fibre gene section, by SOEing PCR using the outer primers B4450 and B4429. The resulting PCR product may then be cleaned and digested with AvrII and KpnI, and ligated to pSMX402 that has also been digested with AvrII and KpnI, yielding plasmid pSMX403 (FIGS. 2A-2B).

Primer B4450 consists of a 5' AvrII restriction site, followed by sequence complementary to the 3' end of the lacZα open reading frame (FIGS. 2A-2B). Primer B4452 consists of a 5' section of sequence that overlaps the 3' end PTP92 tail fibre region that encodes the C-terminal receptor-binding region, followed by sequence of the 5' end of the lacZα open reading frame (FIGS. 2A-2B). Primer B4451 is the reverse complement of primer B4452 (FIGS. 2A-2B). Primer B4454 consists of 5' sequence from within the region of the Phi33 tail fibre gene that encodes the N-terminal region (underlined), followed sequence within the region of the PTP92 tail fibre gene that encodes the C-terminal receptor-binding region (FIGS. 2A-2B). Primer B4453 is the reverse complement of Primer B4454. Primer B4429 consists of a 5' KpnI restriction site (underlined), followed by sequence that is complementary to a region approximately 1 kb upstream of the tail fibre gene in Phi33 (FIGS. 2A-2B).

Primer B4450
(SEQ ID NO: 15)
5'-GATA<u>CCTAGG</u>TTAGCGCCATTCGCCATTC-3'

Primer B4452
(SEQ ID NO: 16)
5'-<u>CTATTCCAGCGGGTAACGTAAA</u>ATGACCATGATTACGGATTC-3'

Primer B4451
(SEQ ID NO: 17)
5'-GAATCCGTAATCATGGTCAT<u>TTTACGTTACCCGCTGGAATAG</u>-3'

Primer B4454
(SEQ ID NO: 18)
5'-<u>CAAGCGGGCCGGCTGGTCTCTC</u>GGCAATAACTCCTATGTGATC-3'

Primer B4453
(SEQ ID NO: 19)
5'-GATCACATAGGAGTTATTGCC<u>GAGAGACCAGCCGGCCCGCTTG</u>-3'

Primer B4429
(SEQ ID NO: 20)
5'-GATA<u>GGTACC</u>GCGACCGGTCTGTACTTC-3'

3. pSMX404 (FIG. 3), comprising pSM1080 carrying a region of the gene encoding the C-terminal receptor-binding region of the PTP92 tail fibre, and a region of Phi33 sequence located immediately downstream of the Phi33 tail fibre gene, may be constructed as follows.

Figure 3:
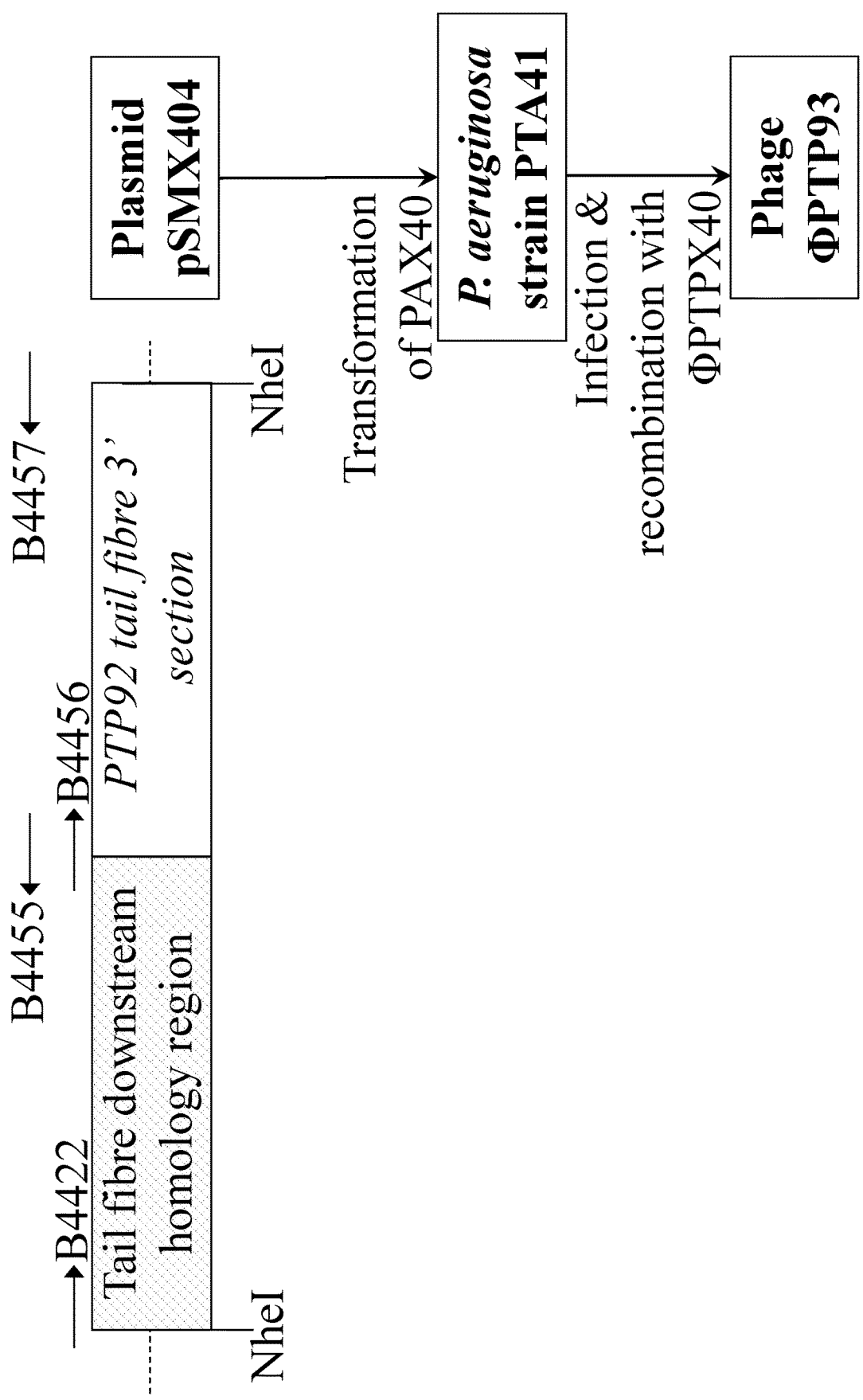
FIG. 3 is a schematic diagram showing construction of plasmids encoding hybrid tail fibre genes, which do not include the lacZα marker.

The region of Phi33 sequence located immediately downstream of the Phi33 tail fibre may be amplified by PCR using primers B4422 and B4455 (FIG. 3). The region of the gene encoding the C-terminal receptor-binding region of the PTP92 tail fibre may be amplified by PCR using primers B4456 and B4457 (FIG. 3). These two PCR products may then be joined by SOEing PCR, using the two outer primers B4422 and B4457. The resulting PCR product may then be cleaned, digested with NheI, cleaned again, and ligated to pSM1080 that has also been digested with NheI and then treated with alkaline phosphatase prior to ligation, to yield plasmid pSMX404 (FIG. 3).

Primer B4455 consists of a 5' section of the region of the gene encoding the C-terminal receptor-binding region of the PTP92 tail fibre gene (underlined), followed by sequence immediately downstream of the Phi33 tail fibre gene (FIG. 3). Primer B4456 is the reverse complement of primer B4455 (FIG. 3). Primer B4457 consists of a 5' NheI restriction site (underlined), followed by sequence of a region within the section of the tail fibre gene of PTP92, that encodes the C-terminal, receptor-binding region (FIG. 3).

Primer B4455
(SEQ ID NO: 21)
5'-<u>CTATTCCAGCGGGTAACGTAAA</u>ATGAAATGGACGCGGATCAG-3'

Primer B4456
(SEQ ID NO: 22)
5'-CTGATCCGCGTCCATTTCATT<u>TTTACGTTACCCGCTGGAATAG</u>-3'

Primers B4457
(SEQ ID NO: 23)
5'-GATA<u>GCTAGC</u>GGCAATAACTCCTATGTGATC-3'

Figure 4A:
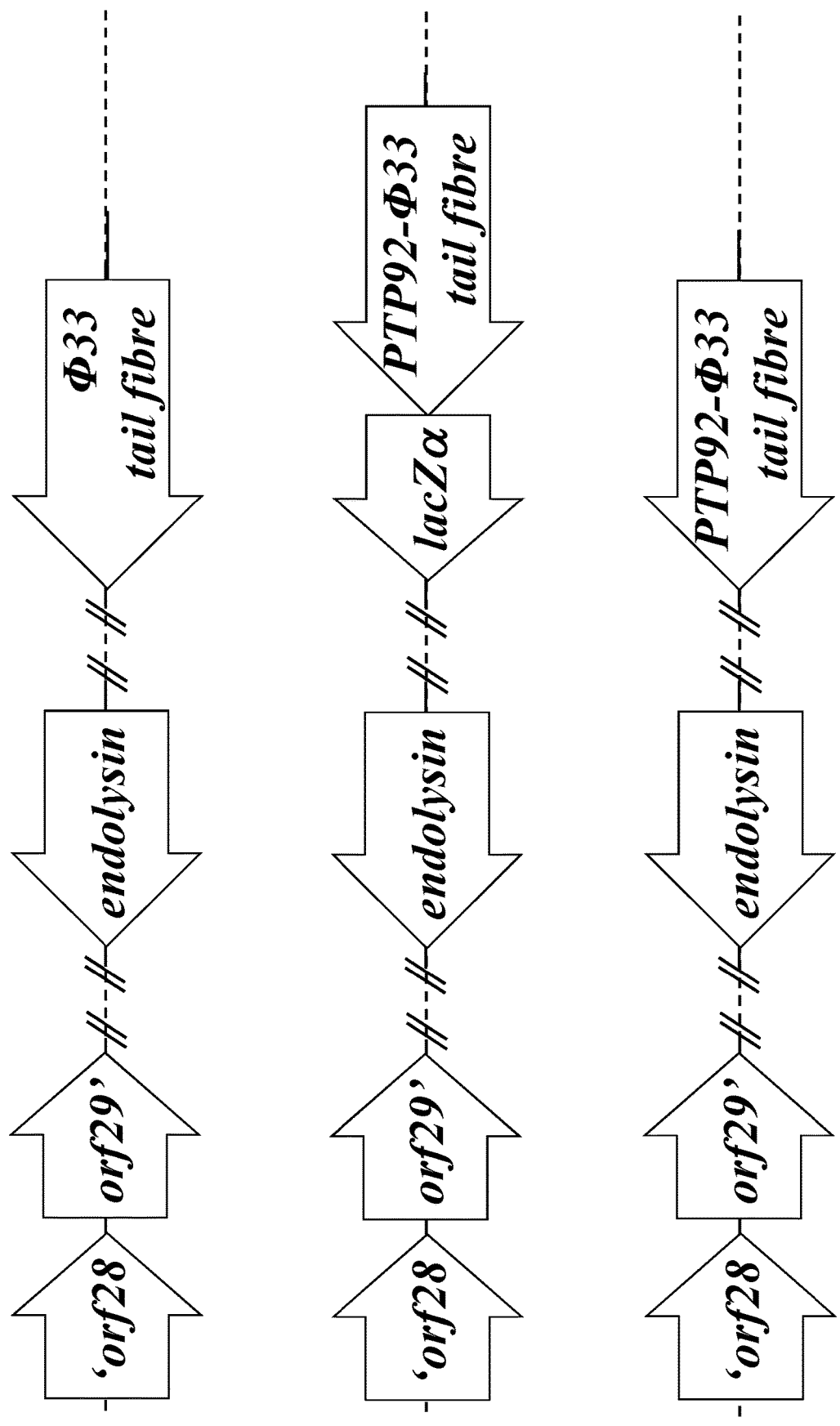
FIGS. 4A-4B are a schematic diagram showing construction of phage with hybrid tail fibre genes.
Figure 4B:
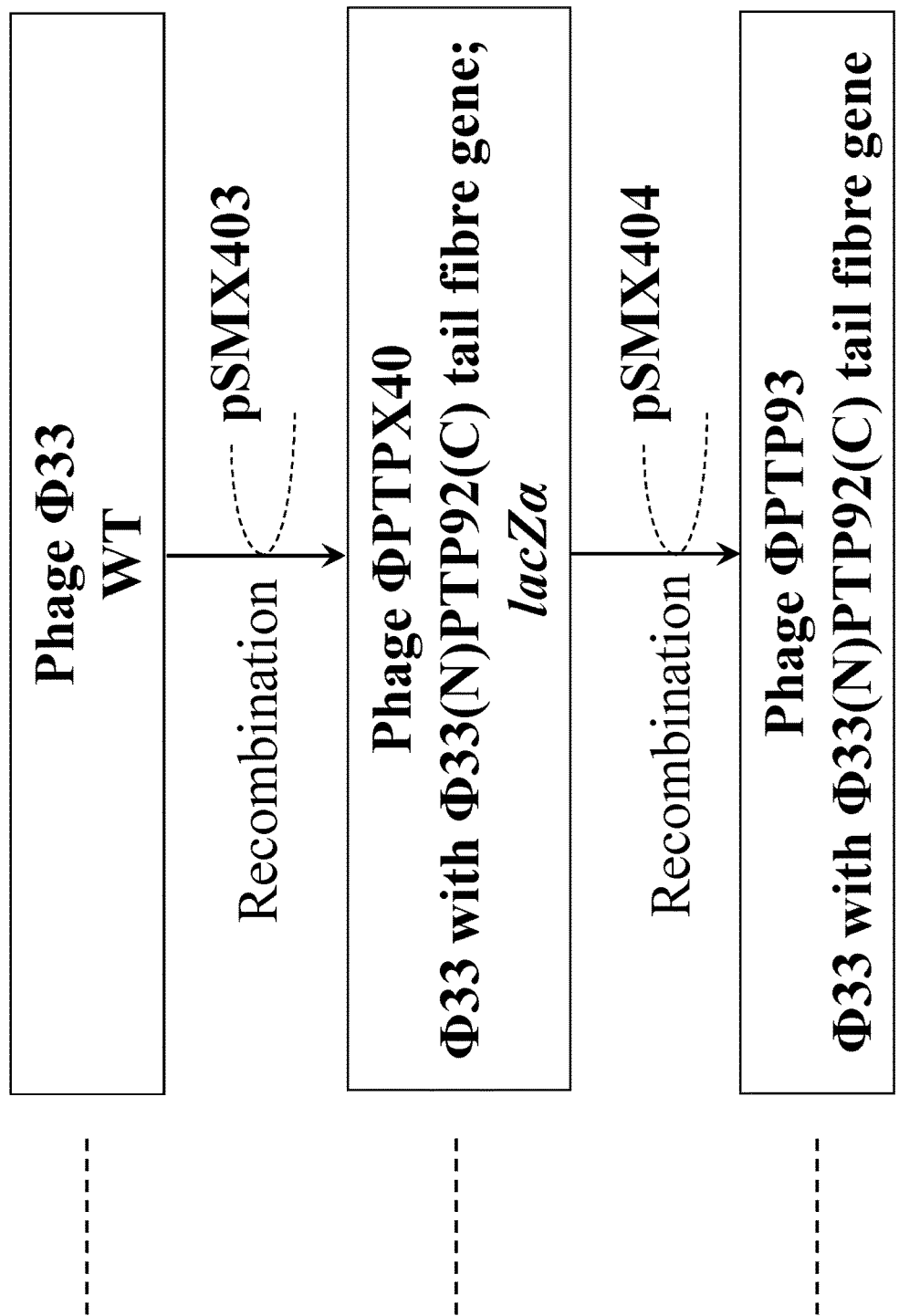
Figure 5A:
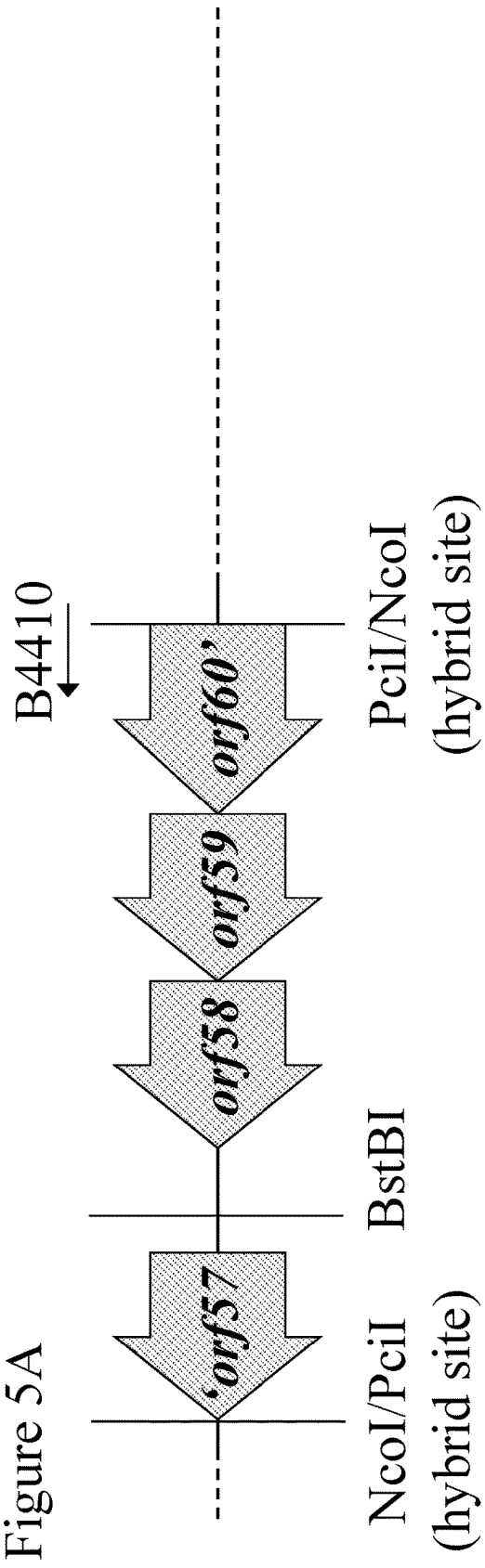
FIGS. 5A-5F are a schematic diagram showing construction of plasmids for the genetic modification of phage to introduce an additional tail fibre gene or tail fibre hybrid gene, utilising a lacZα marker.
Figure 5A:
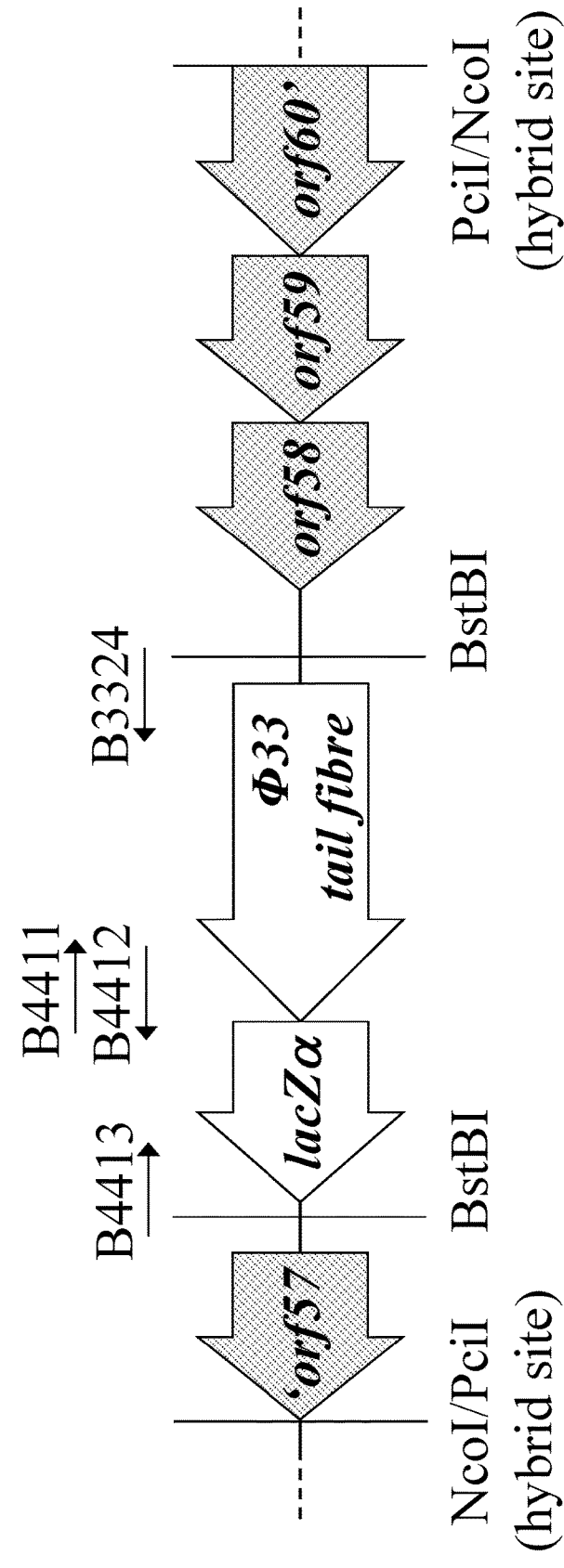
Figure 5B:
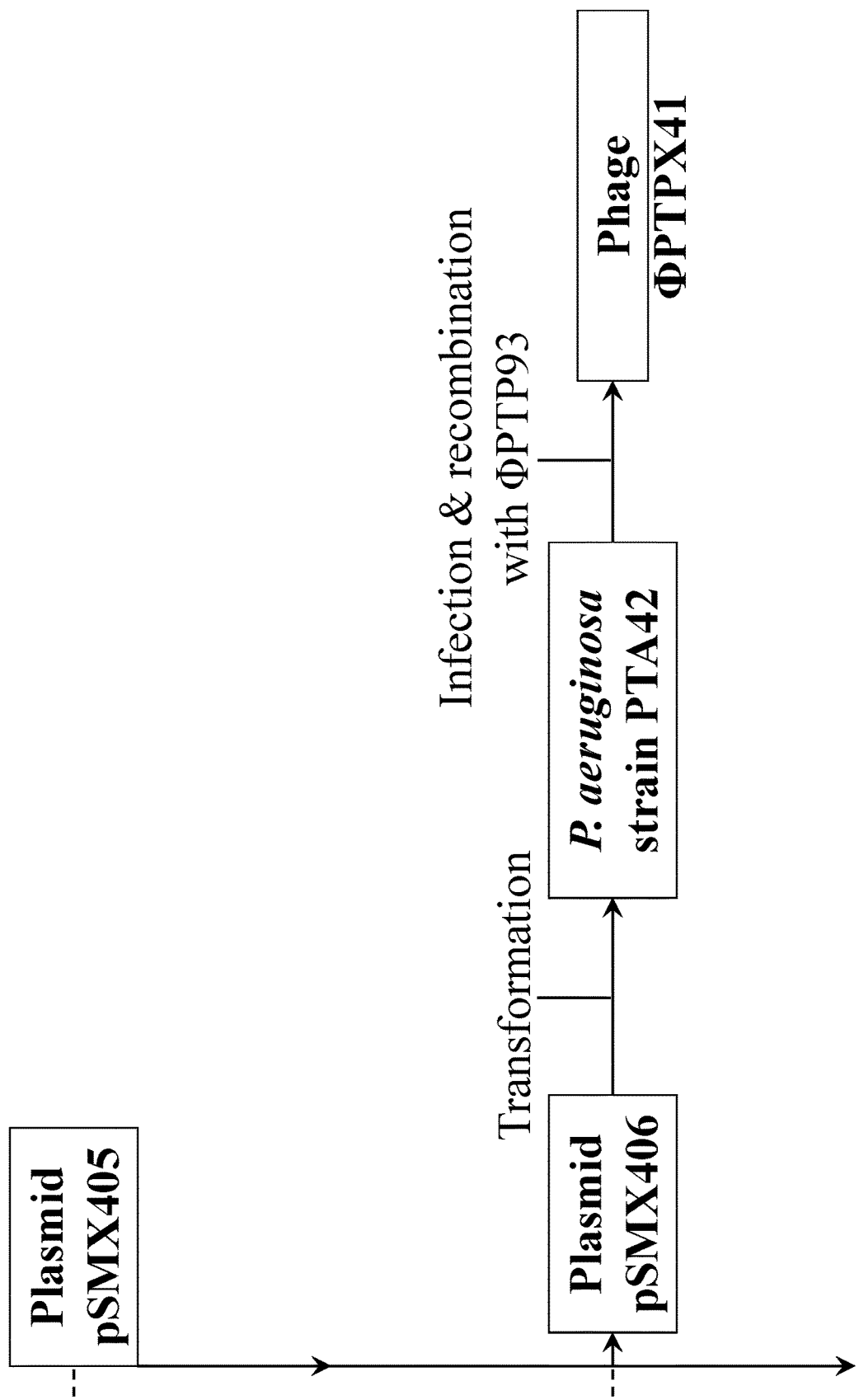
Figure 5C:
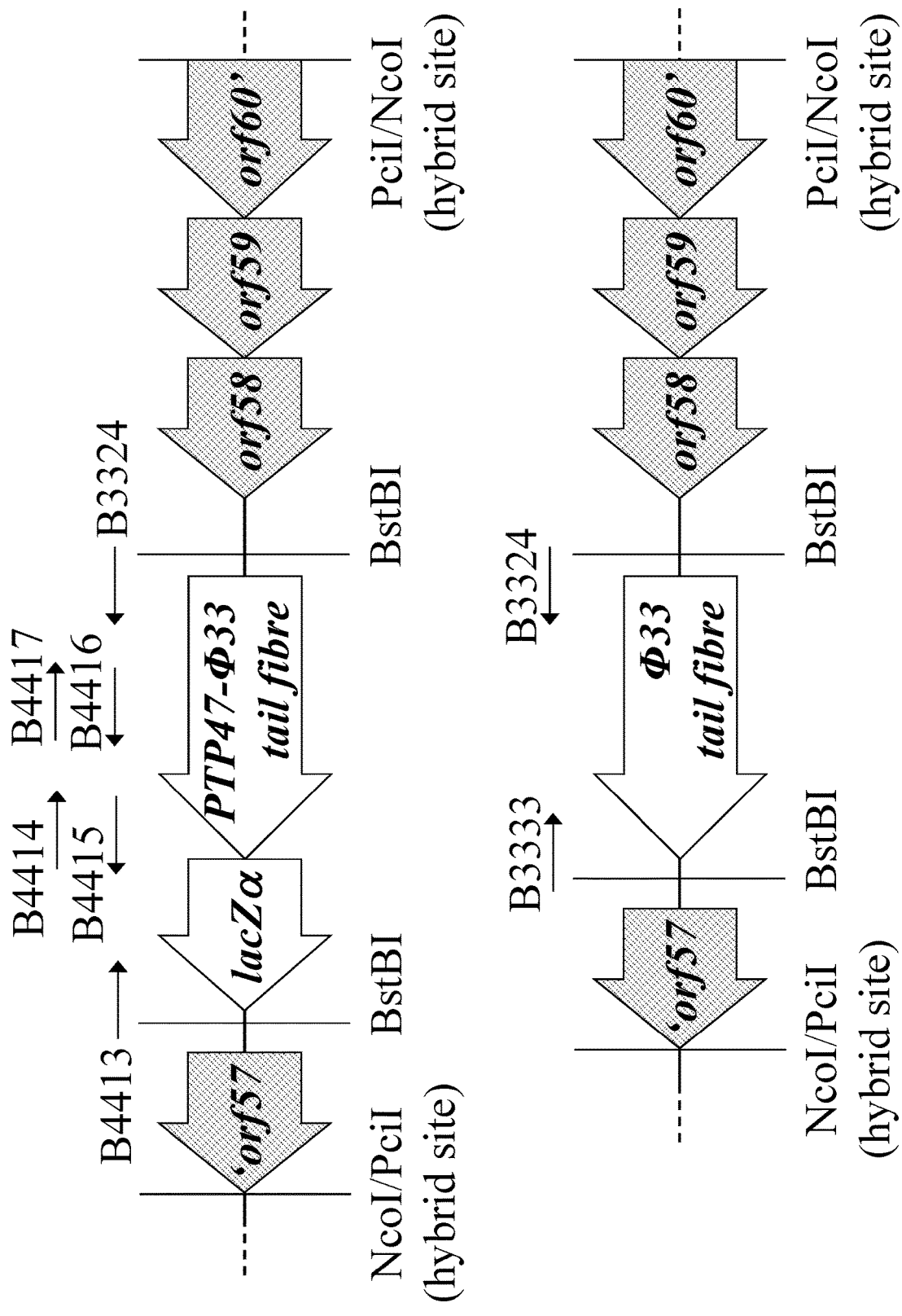
Figure 5D:
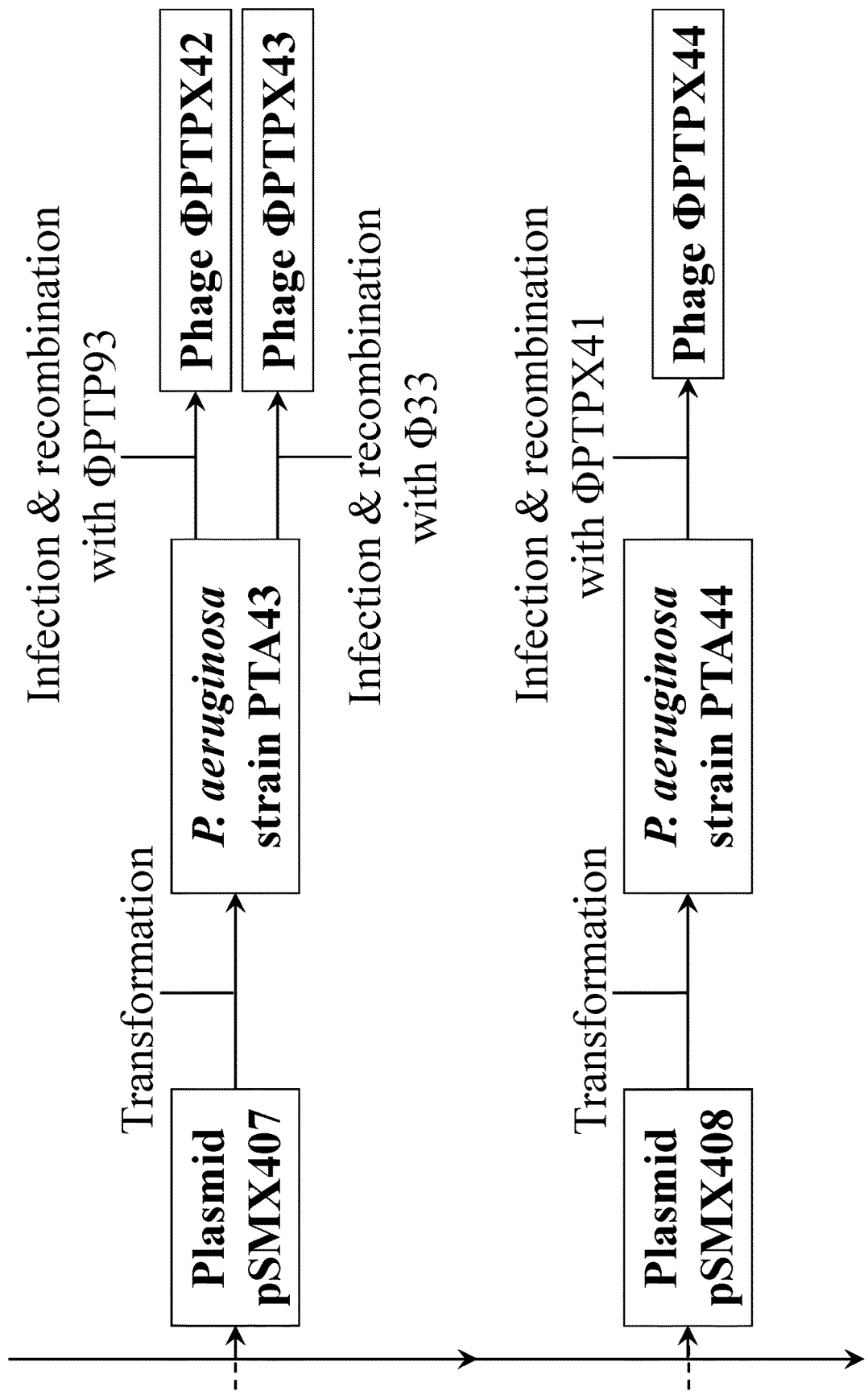
Figure 5E:
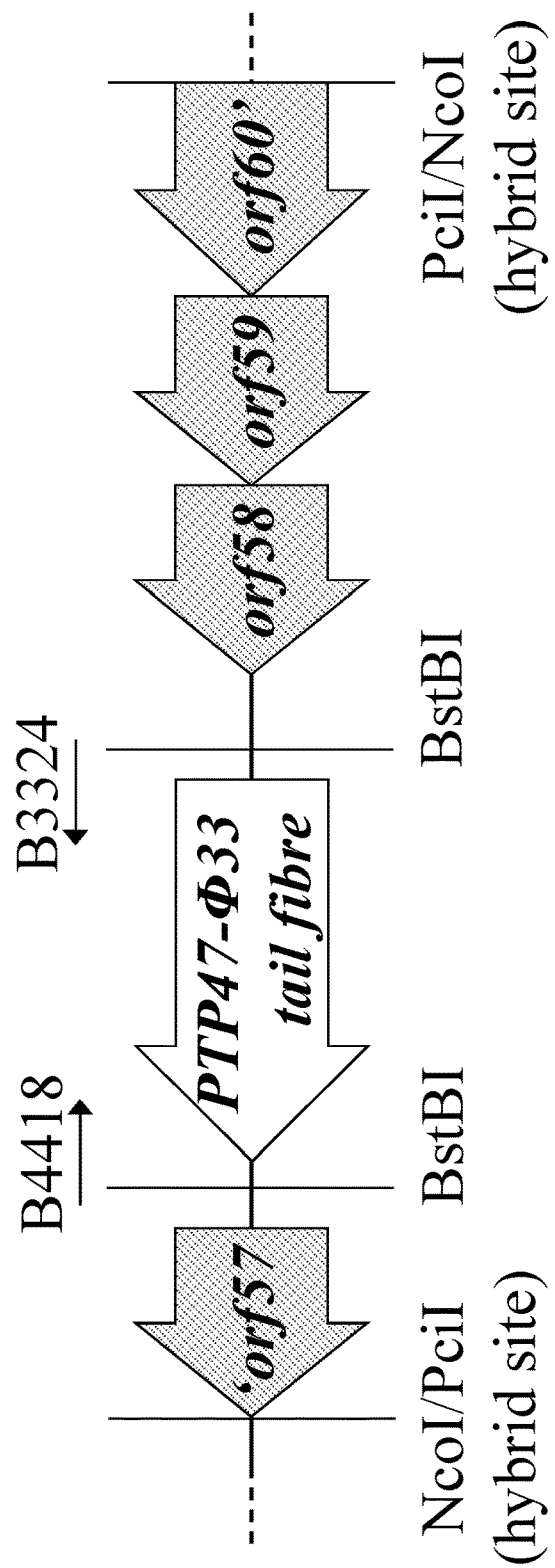
Figure 5F:
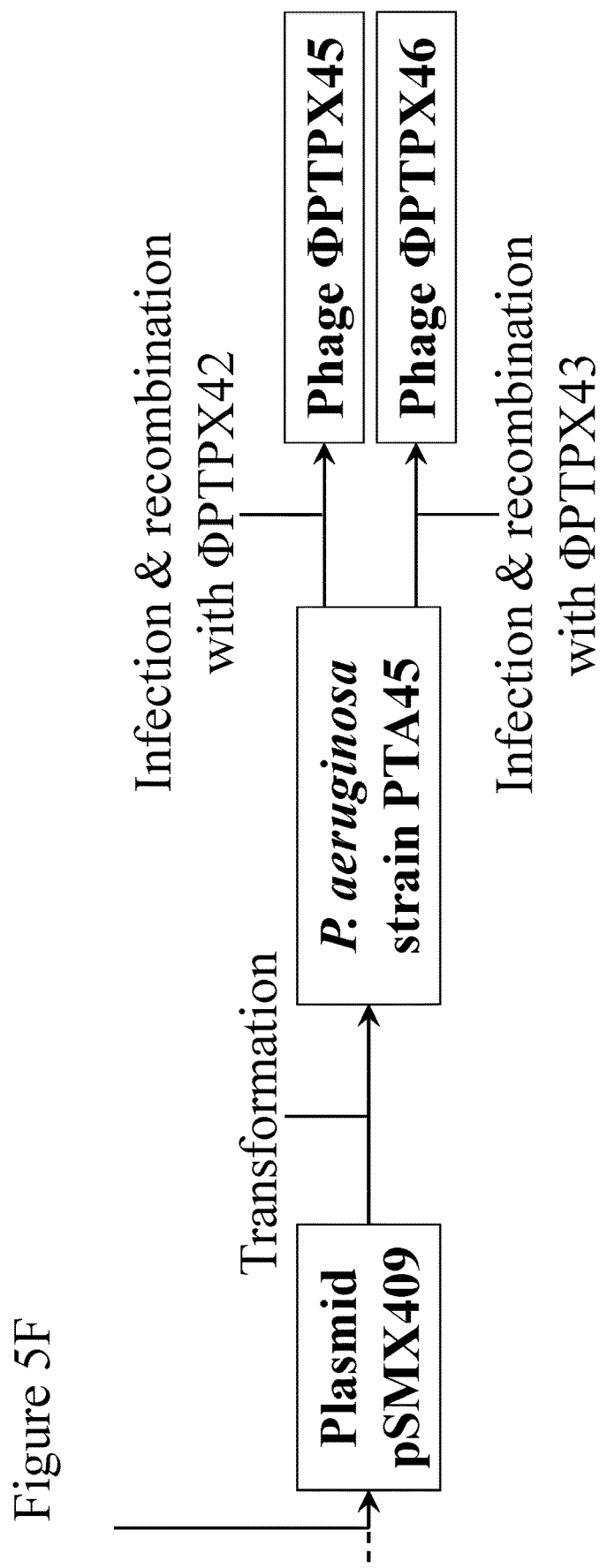

Genetic Modification of Phi33 to Replace the 3' Region of the Tail Fibre Gene, Encoding the C-Terminal Receptor-Binding Region, with that of PTP92, to Form the Phi33(C) PTP92(N) Tail Fibre Gene, at the Native Position within the Phi33 Genome 1. Plasmid pSMX403 (FIGS. 2A-2B; FIGS. 4A-4B) may be introduced into *P. aeruginosa* strain PAX40 by conjugation, selecting transconjugants on the basis of tetracycline resistance (50 μg/ml), yielding strain PTA40.

2. Strain PTA40 may be infected with phage Phi33, and the progeny phage harvested.

3. Recombinant phage in which the region of the Phi33 gene encoding the C-terminal, receptor-binding region of the tail fibre has been replaced by that of PTP92, and to which lacZα has been added, may be identified by plaquing the lysate from step (2) on *P. aeruginosa* strain PAX40, onto medium containing S-gal, looking for black plaques, which are indicative of β-galactosidase activity.

4. PCR may be carried out to check that the tail fibre gene has been replaced, and that lacZα is present.

5. Following identification of a verified isolate (PTPX40; FIGS. 4A-4B), this isolate may be plaque purified twice more on *P. aeruginosa* strain PAX40, prior to further use.

Genetic Modification of PTPX40 to Remove the lacZα Marker, Generating PTP93 (Phi33, Carrying the Phi33(N) PTP92(C) Tail Fibre Gene)

1. Plasmid pSMX404 (FIG. 3; FIGS. 4A-4B) may be introduced into *P. aeruginosa* strain PAX40 by conjugation, selecting transconjugants on the basis of tetracycline resistance (50 g/ml), yielding strain PTA41.

2. Strain PTA41 may be infected with phage PTPX40, and the progeny phage harvested.

3. Recombinant phage in which the lacZα marker has been removed may be identified by plaquing the lysate from step (2) on *P. aeruginosa* strain PAX40, onto medium containing S-gal, looking for white plaques, which is indicative of loss of β-galactosidase activity.

4. PCR may be carried out to check that the tail fibre gene has been retained, and that lacZα has been removed.

5. Following identification of a verified isolate (PTP93; FIGS. 4A-4B), this isolate may be plaque purified twice more on *P. aeruginosa* strain PAX40, prior to further use.

Construction of Plasmids for the Genetic Modification of PTP93 to Introduce Either the Phi33 Tail Fibre Gene, or the Gene Encoding the Phi33(N)PTP47(C) Tail Fibre at Ectopic Position 1

1. Plasmid pSMX405 (FIGS. 5A-5F), comprising pSM1080 containing a 2.8 kb fragment of Phi33 spanning a continuous 'orf60 to orf57' stretch (neither orf60 nor orf57 were complete), may be constructed as follows. FIGS. 5A-5F show the priming sites for the oligonucleotides described below for amplification of regions from the Phi33 genome.

PCR amplification of Phi33 DNA may be carried out using primers B4410 and B3332 (FIGS. 5A-5F), to yield a 2.9 kb fragment, which may be cleaned and digested with PciI. Following digestion, the DNA may be cleaned and ligated to pSM1080 that has been digested with NcoI and treated with alkaline phosphatase, to yield pSMX405 (FIGS. 5A-5F).

Primer B4410 consists of a 5' PciI site (underlined; FIGS. 5A-5F), followed by sequence that anneals approximately 240 bp downstream of the start codon of Phi33 orf60, in the sense orientation. Primer B3332 consists of sequence complementary to Phi33 orf57, and anneals approximately 120 bp downstream of an intrinsic PciI site within orf57.

```
B4410
                                       (SEQ ID NO: 24)
5'-CGCGACATGTCCTACAGCAGCGATGGAG-3'

B3332
                                       (SEQ ID NO: 25)
5'-TTACTCCCCCTTCAGGTAGATG-3'
```

2. Plasmid pSMX406 (FIGS. 5A-5F), comprising pSMX405 carrying the complete tail fibre gene from Phi33 and a promoterless lacZα marker, may be constructed as follows.

The complete tail fibre gene from Phi33 (FIGS. 5A-5F) may be amplified by PCR using primers B3324 and B4411. A promoterless lacZα marker may be amplified by PCR from pUC19 using primers B4412 and B4413 (FIGS. 5A-5F). The two PCR products may be joined together by SOEing PCR using the two outer primers, B3324 and B4413. The resulting PCR product may then be digested with BstBI, and ligated to pSMX405 that has also been digested with BstBI and treated with alkaline phosphatase prior to ligation. Plasmid pSMX406 may be isolated following screening of clones to identify a clone in which the Phi33 tail fibre has been cloned in the same orientation as orf57 (FIGS. 5A-5F).

Primer B3324 consists of a 5' BstBI site (underlined), followed by sequence that anneals to the ribosome binding site just upstream of the Phi33 tail fibre gene (FIGS. 5A-5F). Primer B4411 consists of 5' sequence complementary to the beginning of the lacZα marker from pUC19, followed by sequence complementary to the end of the tail fibre gene from Phi33 (underlined; FIGS. 5A-5F). Primer B4412 is the reverse complement of Primer B4411 (FIGS. 5A-5F). Primer B4413 consists of a 5' BstBI site (underlined), followed by sequence complementary to the region between the native Phi33 BstBI site and orf57, followed in turn by sequence complementary to the end of the lacZα marker from pUC19 (FIGS. 5A-5F).

```
Primer B3324
                                       (SEQ ID NO: 26)
5'-ACTCTTCGAATTAACGGGATCCTCATTCAGGAGTAATGAC-3'

Primer B4411
                                       (SEQ ID NO: 27)
5'-GTGAATCCGTAATCATGGTCATTTTACGTCACTCGCTGGAAAAG-3'

Primer B4412
                                       (SEQ ID NO: 28)
5'-CTTTTCCAGCGAGTGACGTAAAATGACCATGATTACGGATTCAC-3'

Primer B4413
                                       (SEQ ID NO: 29)
5'-GATATTCGAAGAGTCGTGGTTAGCGCCATTCGCCATTC-3'
```

3. Plasmid pSMX407 (FIGS. 5A-5F), comprising pSMX405 carrying a tail fibre gene consisting of the 5' section of Phi33 DNA encoding the N-terminal region of the Phi33 tail fibre, and the 3' section of PTP47 DNA encoding the C-terminal, receptor-binding region of the PTP47 tail fibre, in addition to a promoterless lacZα marker, may be constructed as follows.

The DNA region encoding the N-terminal region of the Phi33 tail fibre may be amplified by PCR using primers B3324 and B4417 (FIGS. 5A-5F). The DNA region encoding the C-terminal, receptor-binding region of the PTP47 tail fibre may be amplified by PCR using primers B4416 and B4414 (FIGS. 5A-5F). The two PCR products may be joined together by SOEing PCR using the outer primers B3324 and B4414. The lacZα marker from pUC19 may be amplified by PCR using primers B4415 and B4413 (FIGS. 5A-5F). The lacZα marker may be joined to the constructed tail fibre PCR product by SOEing PCR using the outer primers B3324 and B4413. The resulting PCR product may then be digested with BstBI and ligated to pSMX405 that has been digested with BstBI and treated with alkaline phosphatase prior to ligation. Plasmid pSMX407 may be isolated following screening of clones to identify a clone in which the Phi33 (N)PTP47(C) tail fibre has been cloned in the same orientation as orf57 (FIGS. 5A-5F).

Primer B4417 consists of a 5' section of sequence complementary to part of PTP47 encoding the C-terminal, receptor-binding region of the PTP47 tail fibre (underlined), followed by sequence complementary to part of Phi33 encoding the N-terminal region of the Phi33 tail fibre (FIGS. 5A-5F). Primer B4416 is the reverse complement of B4417 (FIGS. 5A-5F). B4414 consists of 5' sequence complementary to the beginning of the lacZα marker from pUC19, followed by sequence complementary to the end of the tail fibre gene from PTP47 (underlined; FIGS. 5A-5F). Primer B4415 is the reverse complement of primer B4414 (FIGS. 5A-5F).

```
Primer B4417
                                       (SEQ ID NO: 30)
5'-GATCACATAGGAGTTATTGCCGAGAGACCAGCCGGCCCGCTTG-3'

Primer B4416
                                       (SEQ ID NO: 31)
5'-CAAGCGGGCCGGCTGGTCTCTCGGCAATAACTCCTATGTGATC-3'

Primer B4414
                                       (SEQ ID NO: 32)
5'-GTGAATCCGTAATCATGGTCATTTTACGTCACTCGCTGGAAAAG-3'
```

-continued

Primer B4415
(SEQ ID NO: 33)
5'-CTTTTCCAGCGAGTGACGTAAAATGACCATGATTACGGATTCAC-3'

Genetic Modification of PTP93 to Add the Phi33 Tail Fibre Gene and a lacZα Marker, Upstream of Orf57

Figure 6A:
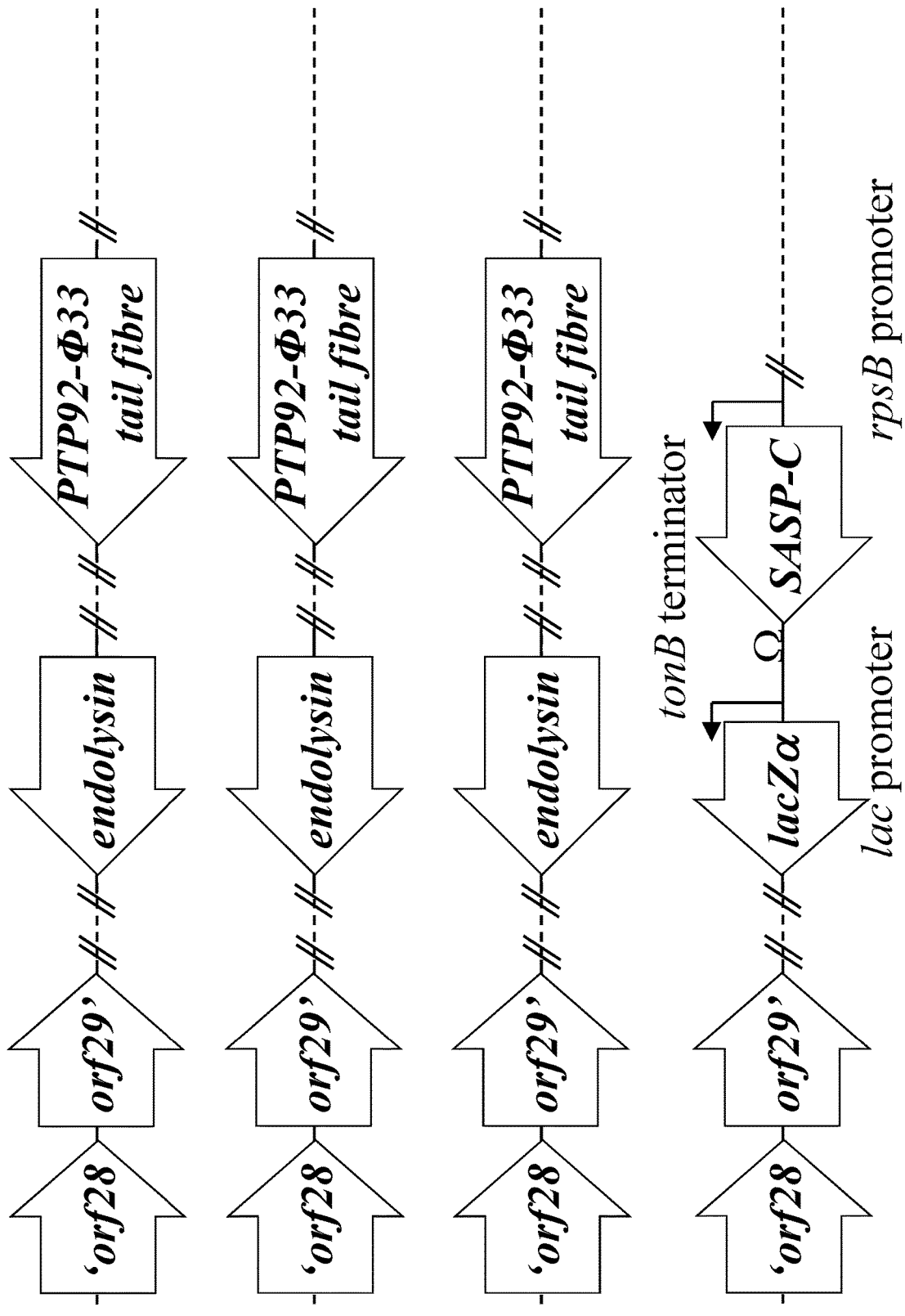
FIGS. 6A-6C are a schematic diagram showing genetic modification of phage to add an extra tail fibre gene, utilising a lacZα marker, and then to replace endolysin with rpsB-SASP-C, also utilising a lacZα marker.
Figure 6B:
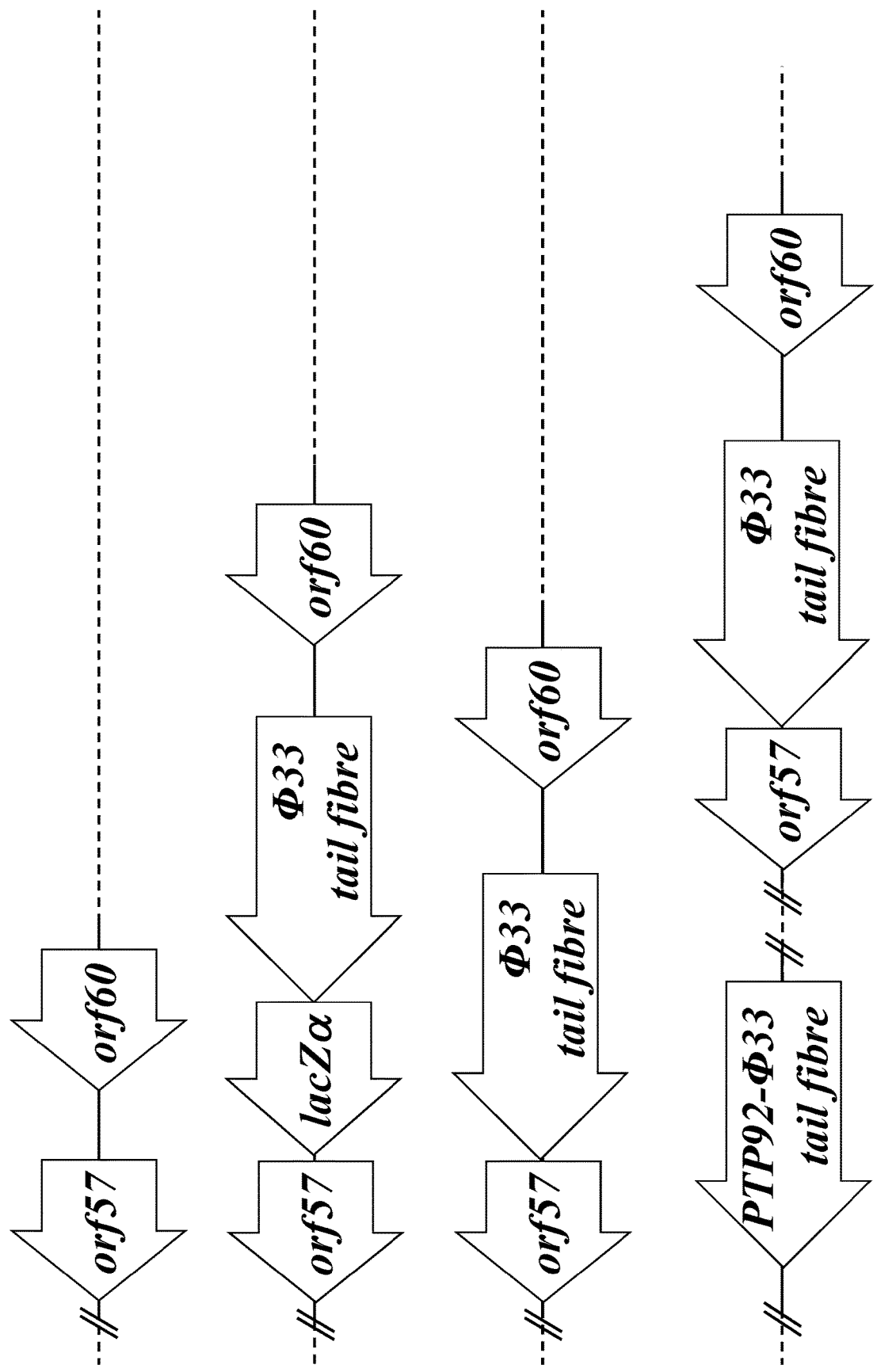
Figure 6C:
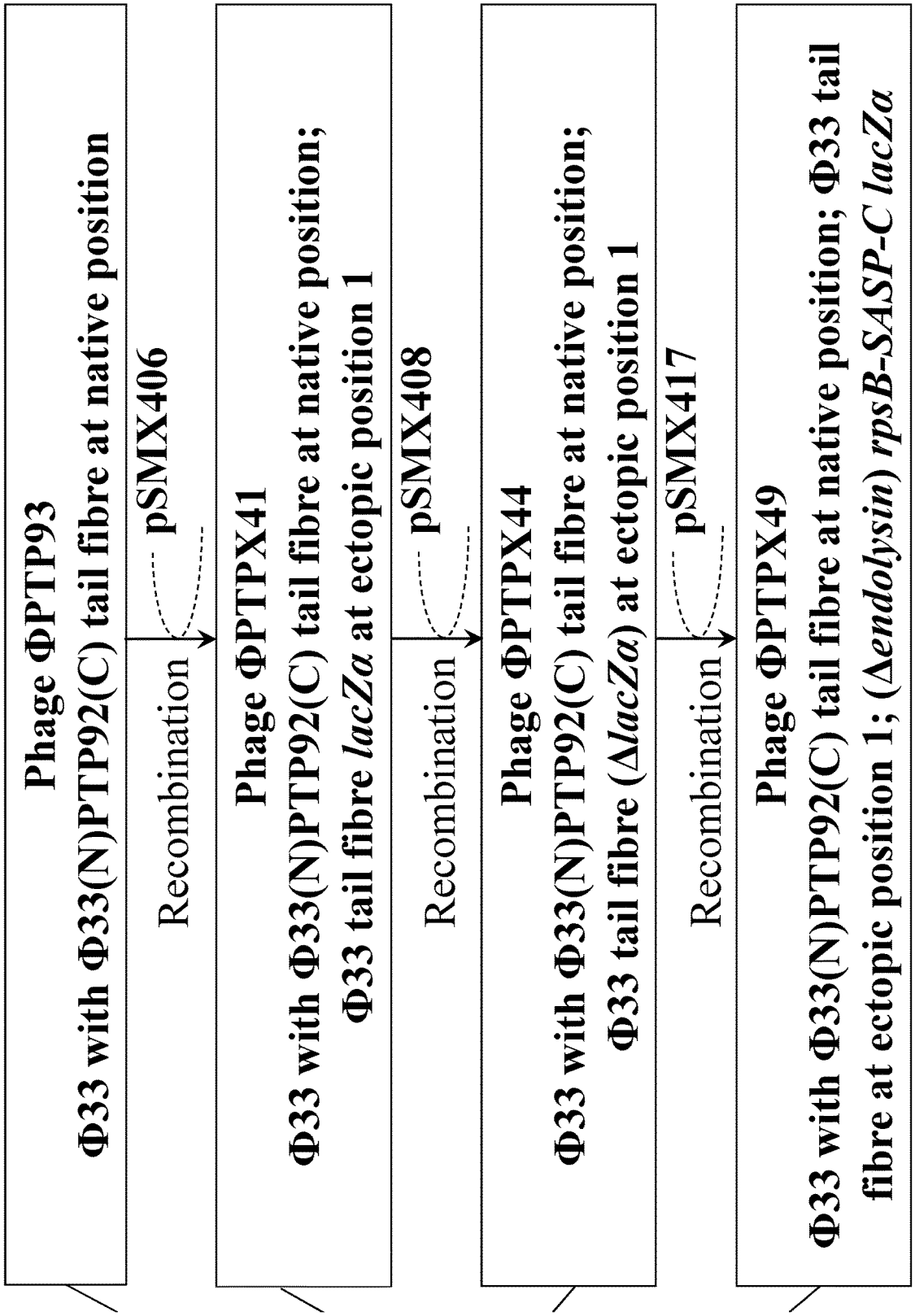

1. pSMX406 (FIGS. 5A-5F; FIGS. 6A-6C) may be introduced into *P. aeruginosa* strain PML14 by conjugation, selecting transconjugants on the basis of tetracycline resistance (50 µg/ml), yielding strain PTA42.

2. Strain PTA42 may be infected with PTP93, and the progeny phage harvested.

3. Recombinant phage, which have acquired the Phi33 tail fibre and lacZα marker upstream of orf57, may be identified by plaquing on *P. aeruginosa* strain PAX40 using medium containing S-gal, a chromogenic substrate that detects β-galactosidase activity, looking for black plaques.

4. PCR may be carried out to confirm that the Phi33 tail fibre and lacZα marker have been introduced upstream of orf57 in PTP93, and to confirm that the native PTP93 tail fibre region is still intact.

5. Following identification of a verified isolate (PTPX41; FIGS. 6A-6C), the new recombinant phage may be plaque purified twice more on *P. aeruginosa* strain PAX40, before further use. PTPX41 is therefore a Phi33 derivative carrying the gene encoding the Phi33(N)PTP92(C) tail fibre at the native position, and the Phi33 wild type tail fibre gene along with a lacZα marker at ectopic position 1.

Genetic Modification of PTP93 to Add the Phi33(N)PTP47 (C) Tail Fibre Gene and a lacZα Marker, Upstream of Orf57

Figure 7A:
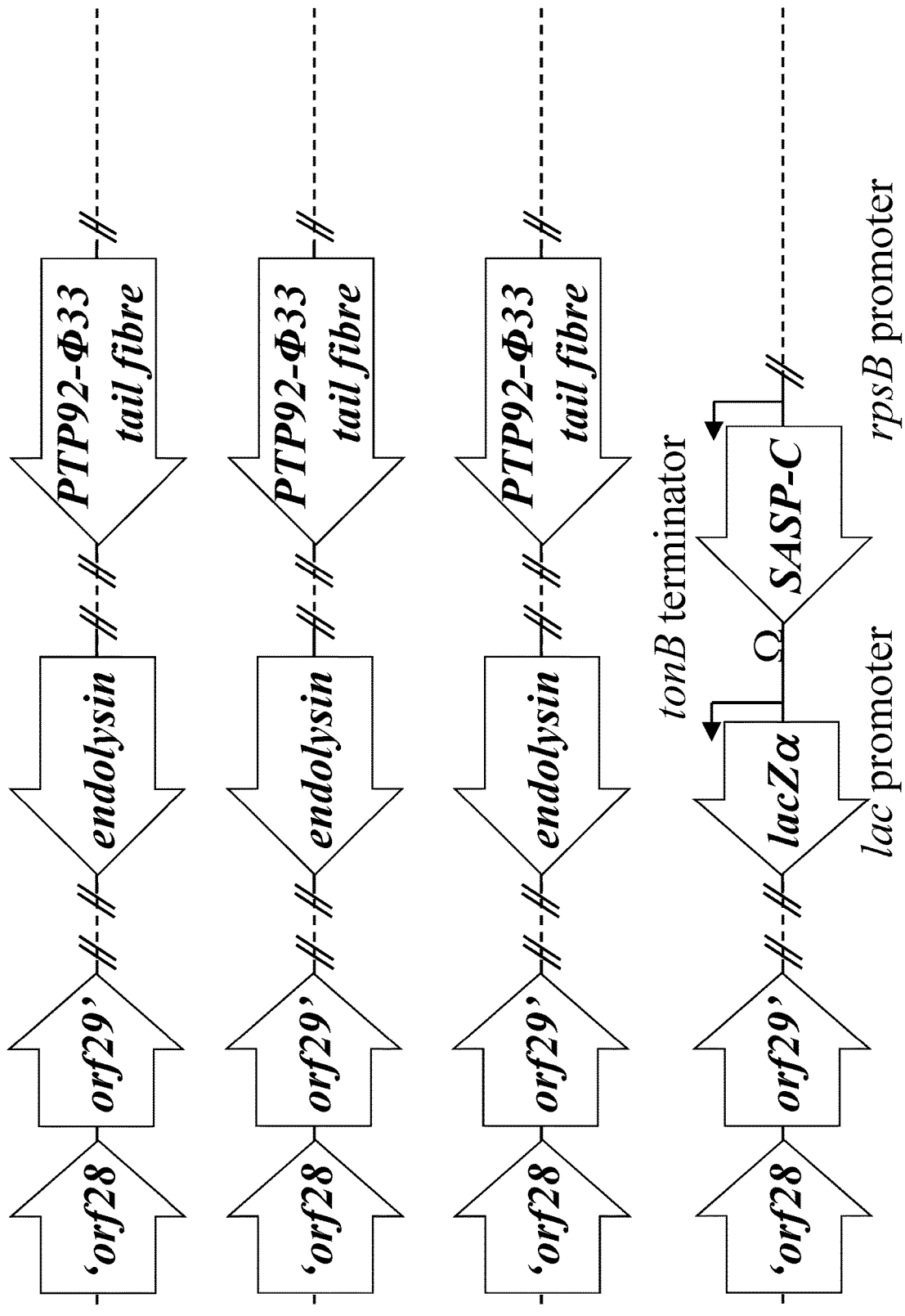
FIGS. 7A-7C are a schematic diagram showing genetic modification of further phage to add an extra tail fibre hybrid gene, utilising a lacZα marker, and then to replace endolysin with rpsB-SASP-C, also utilising a lacZα marker.
Figure 7B:
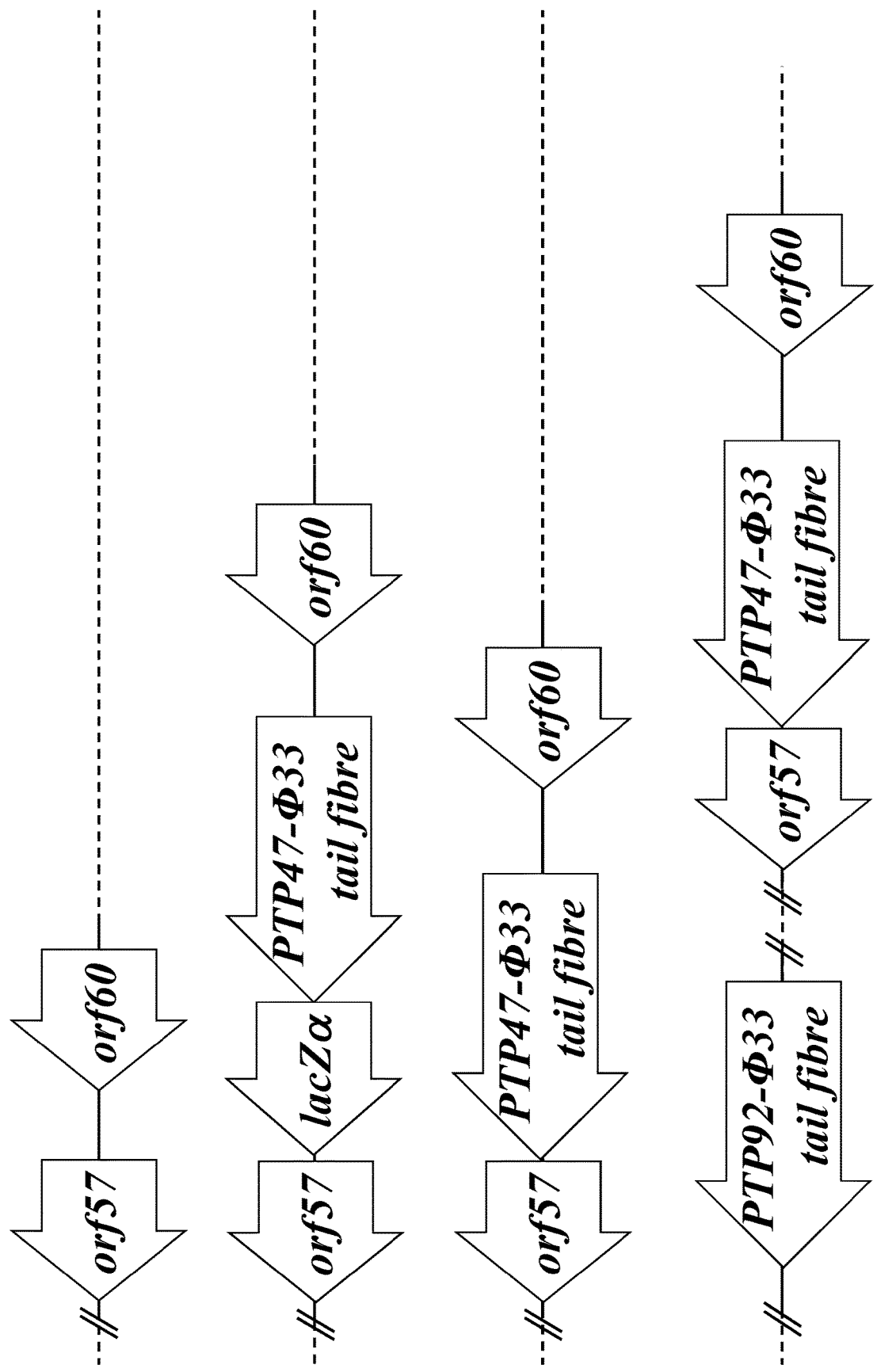
Figure 7C:
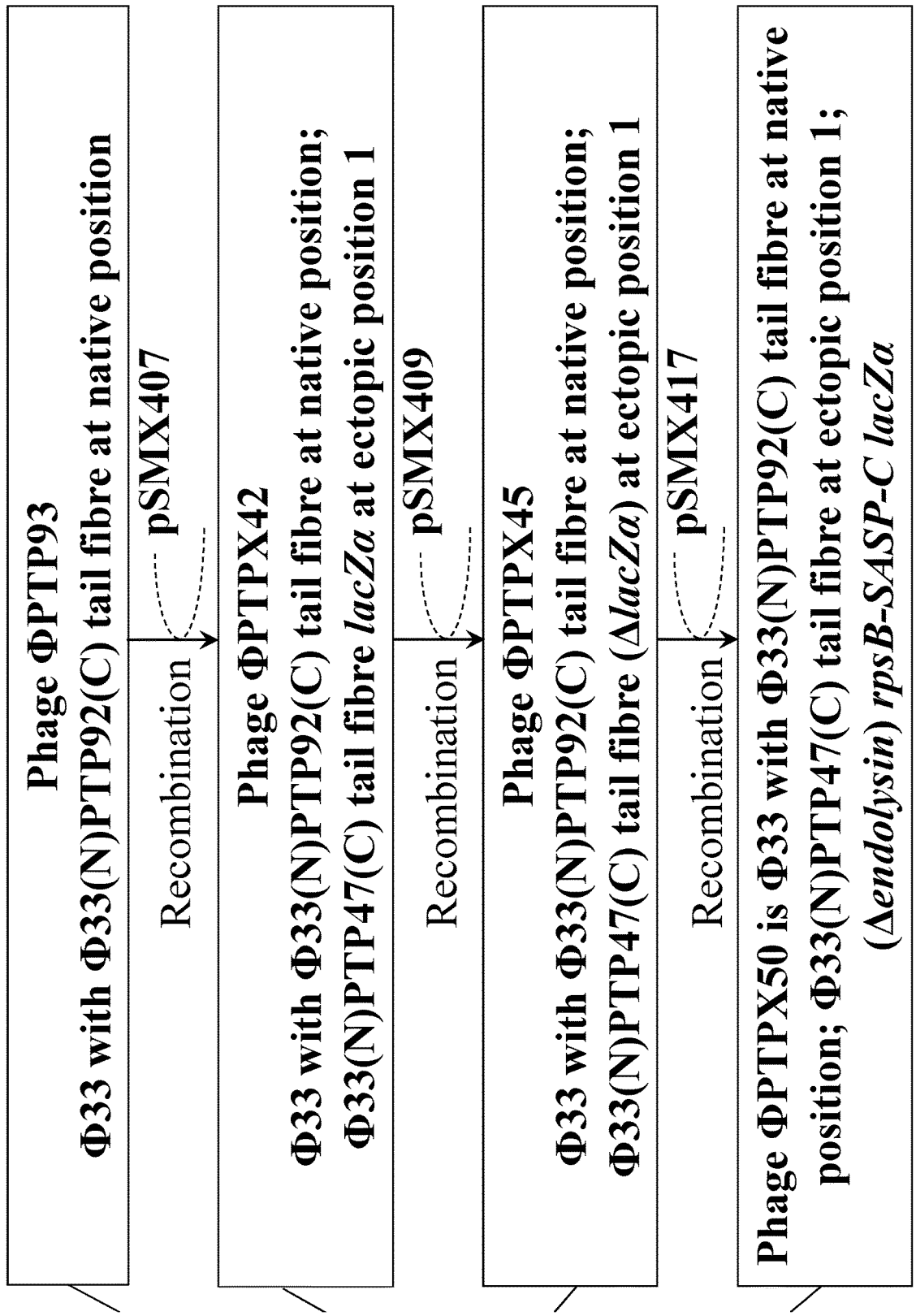

1. pSMX407 (FIGS. 5A-5F; FIGS. 7A-7C) may be introduced into *P. aeruginosa* strain PML14 by conjugation, selecting transconjugants on the basis of tetracycline resistance (50 µg/ml), yielding strain PTA43.

2. Strain PTA43 may be infected with PTP93, and the progeny phage harvested.

3. Recombinant phage, which have acquired the gene encoding the Phi33(N)PTP47(C) tail fibre, in addition to the lacZα marker, upstream of orf57, may be identified by plaquing on *P. aeruginosa* strain PAX40 using medium containing S-gal, a chromogenic substrate that detects β-galactosidase activity, looking for black plaques.

4. PCR may be carried out to confirm that the gene encoding the Phi33(N)PTP47(C) tail fibre, in addition to the lacZα marker, has been introduced upstream of orf57 in PTP93, and to confirm that the native PTP93 tail fibre region is still intact.

5. Following identification of a verified isolate (PTPX42; FIGS. 7A-7C), the new recombinant phage may be plaque purified twice more on *P. aeruginosa* strain PAX40, before further use. PTPX42 is therefore a Phi33 derivative carrying the gene encoding the Phi33(N)PTP92(C) tail fibre at the native position, and the gene encoding the Phi33(N)PTP47 (C) tail fibre along with a lacZα marker at ectopic position 1.

Genetic Modification of Phi33 to Add the Phi33(N)PTP47 (C) Tail Fibre Gene and a lacZα Marker, Upstream of Orf57

Figure 8A:
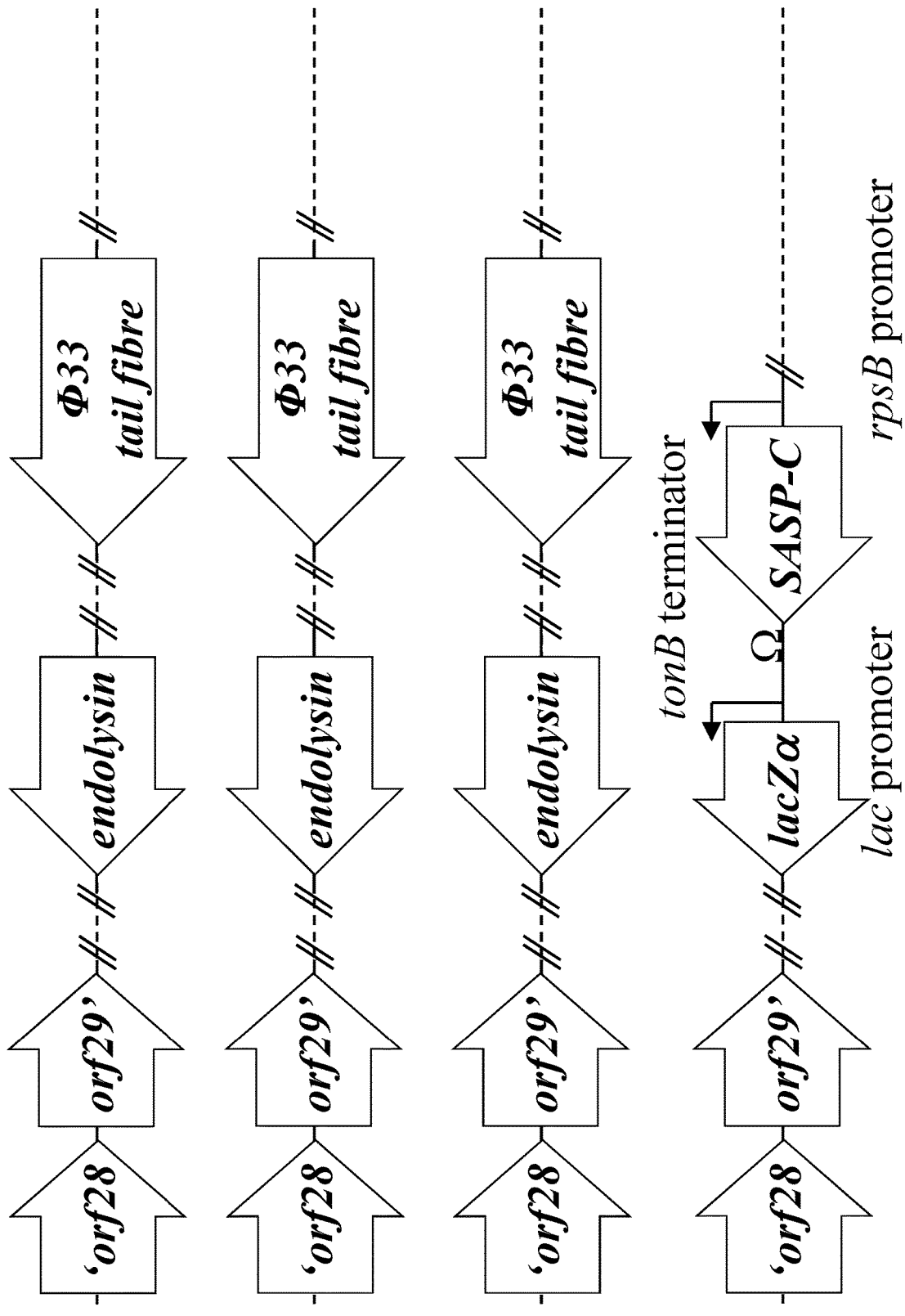
FIGS. 8A-8C are a schematic diagram showing genetic modification of further phage to add an extra tail fibre hybrid gene, utilising a lacZα marker, and then to replace endolysin with rpsB-SASP-C, also utilising a lacZα marker.
Figure 8B:
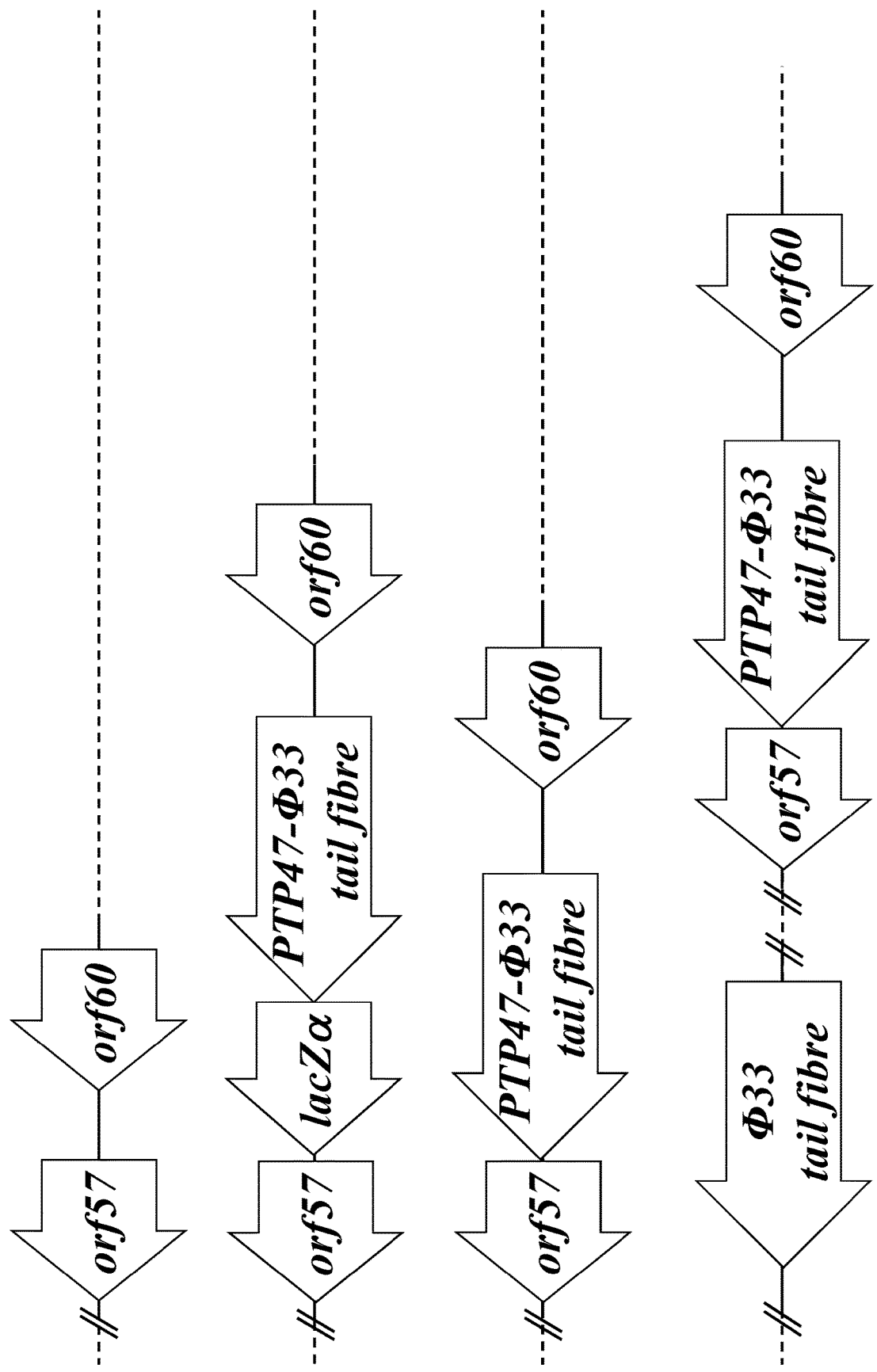
Figure 8C:
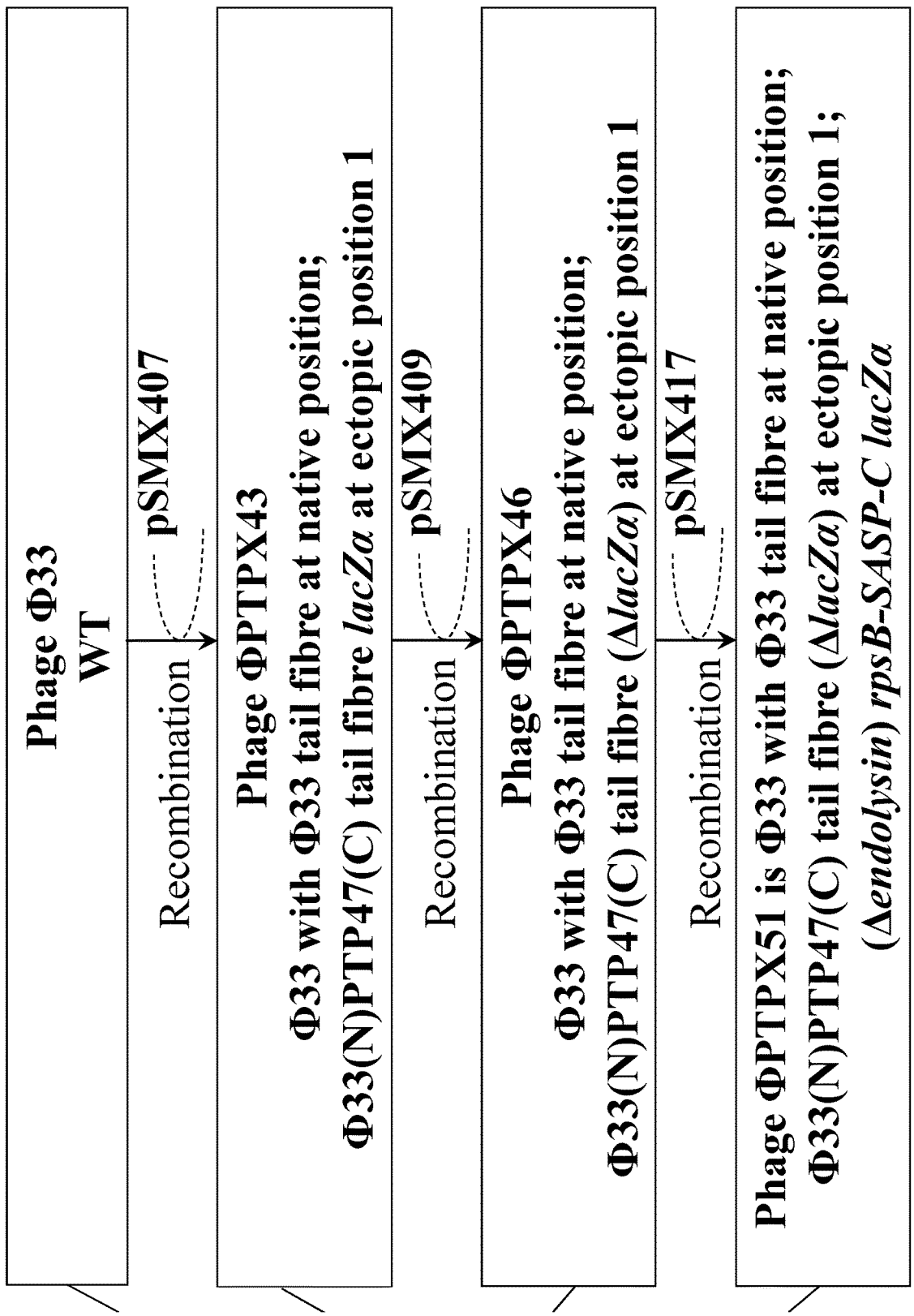

1. pSMX407 (FIGS. 5A-5F; FIGS. 8A-8C) may be introduced into *P. aeruginosa* strain PML14 by conjugation, selecting transconjugants on the basis of tetracycline resistance (50 µg/ml), yielding strain PTA43.

2. Strain PTA43 may be infected with Phi33, and the progeny phage harvested.

3. Recombinant phage, which have acquired the gene encoding the Phi33(N)PTP47(C) tail fibre, in addition to the lacZα marker, upstream of orf57, may be identified by plaquing on *P. aeruginosa* strain PAX40 using medium containing S-gal, a chromogenic substrate that detects β-galactosidase activity, looking for black plaques.

4. PCR may be carried out to confirm that the gene encoding the Phi33(N)PTP47(C) tail fibre, in addition to the lacZα marker, has been introduced upstream of orf57 in Phi33, and to confirm that the native Phi33 tail fibre region is still intact.

5. Following identification of a verified isolate (PTPX43; FIGS. 8A-8C), the new recombinant phage may be plaque purified twice more on *P. aeruginosa* strain PAX40, before further use. PTPX43 is therefore a Phi33 derivative carrying the native Phi33 tail fibre gene at the native position, and the gene encoding the Phi33(N)PTP47(C) tail fibre along with a lacZα marker at ectopic position 1.

Construction of Plasmids to Remove the lacZα Markers from the Double-Tail Fibre Phage. PTPX41, PTPX42 and PTPX43

1. Plasmid pSMX408 (FIGS. 5A-5F), consisting of pSMX405 carrying the Phi33 tail fibre gene, may be constructed as follows.

The Phi33 tail fibre gene may be amplified by PCR using primers B3324 and B3333 (FIGS. 5A-5F). The resulting PCR product may then be digested with BstBI and ligated to pSM405 that has been digested with BstBI and treated with alkaline phosphatase prior to ligation, to yield plasmid pSMX408.

Primer B3333 consists of a 5' BstBI site (underlined), followed by sequence complementary to the region between the native Phi33 BstBI site and orf57, followed in turn by sequence complementary to the 3' end of the tail fibre gene from Phi33 (FIGS. 5A-5F).

Primer B3333
(SEQ ID NO: 34)
5'-GCGCTTCGAAGAGTCGTGGTTACGTCACTCGCTGGAAAAG-3'

2. Plasmid pSMX409 (FIGS. 5A-5F), consisting of pSMX405 carrying the gene encoding the Phi33(N)PTP47 (C) tail fibre, may be constructed as follows.

The gene encoding the Phi33(N)PTP74(C) tail fibre may be amplified by PCR from pSMX407 using primers B3324 and B4418 (FIGS. 5A-5F). The resulting PCR product may then be digested with BstBI and ligated to pSM405 that has been digested with BstBI and treated with alkaline phosphatase prior to ligation, to yield plasmid pSMX409 (FIGS. 5A-5F).

Primer B4418 consists of a 5' BstBI site (underlined), followed by sequence complementary to the region between the native Phi33 BstBI site and orf57, followed in turn by sequence complementary to the 3' end of the tail fibre gene from PTP47 (FIGS. 5A-5F).

Primer B4418
(SEQ ID NO: 35)
5'-GATATTCGAAGAGTCGTGGTTACGTCACTCGCTGGAAAAG-3'

Removal of lacZα Marker from the Double-Tail Fibre Phage PTPX41

1. pSMX408 (FIGS. 5A-5F; FIGS. 6A-6C) may be introduced into *P. aeruginosa* strain PML14 by conjugation, selecting transconjugants on the basis of tetracycline resistance (50 µg/ml), yielding strain PTA44.

2. Strain PTA44 may be infected with PTPX41, and the progeny phage harvested.

3. Recombinant phage, from which the lacZα marker has been removed, may be identified by plaquing on *P. aerugi-*

*nosa* strain PAX40 using medium containing S-gal, a chromogenic substrate that detects β-galactosidase activity, looking for clear plaques.

4. PCR may be carried out to confirm that the lacZα marker has been removed, and that the two tail fibre genes are still intact.

5. Following identification of a verified isolate (PTPX44; FIGS. 6A-6C), the new recombinant phage may be plaque purified twice more on *P. aeruginosa* strain PAX40, before further use. PTPX44 is therefore a Phi33 derivative carrying the gene encoding the Phi33(N)PTP92(C) tail fibre at the native position, and the Phi33 tail fibre gene at ectopic position 1 (ΔlacZα).

Removal of lacZα Marker from the Double-Tail Fibre Phage PTPX42 and PTPX43

1. pSMX409 (FIGS. 5A-5F; FIGS. 7A-7C; FIGS. 8A-8C) may be introduced into *P. aeruginosa* strain PML14 by conjugation, selecting transconjugants on the basis of tetracycline resistance (50 µg/ml), yielding strain PTA45.

2. Strain PTA45 may be infected with PTPX42 (FIGS. 7A-7C) or PTPX43 (FIGS. 8A-8C), as appropriate, and the progeny phage harvested.

3. Recombinant phage, from which the lacZα marker has been removed, may be identified by plaquing on *P. aeruginosa* strain PAX40 using medium containing S-gal, a chromogenic substrate that detects D-galactosidase activity, looking for clear plaques.

4. PCR may be carried out to confirm that the lacZα marker has been removed, and that the two tail fibre genes are still intact.

5. Following identification of verified isolates, the new recombinant phage may be plaque purified twice more on *P. aeruginosa* strain PAX40, before further use. PTPX45 (FIGS. 7A-7C) is therefore a Phi33 derivative carrying the gene encoding the Phi33(N)PTP92(C) tail fibre at the native position and the gene encoding the Phi33(N)PTP47(C) tail fibre at ectopic position 1 (ΔlacZα). PTPX46 (FIGS. 8A-8C) is therefore a Phi33 derivative carrying the Phi33 tail fibre gene at the native position and the gene encoding the Phi33(N)PTP47(C) tail fibre at ectopic position 1 (ΔlacZα).

Construction of a Plasmid to Add a Third Tail Fibre Gene to PTPX44, at Ectopic Position 2, in the Intergenic Region Between Orf28 and Orf29

1. Plasmid pSMX410 (FIGS. 9A-9C), comprising pSM1080 carrying sequences of Phi33 DNA that flank the orf28-29 intergenic region, may be constructed as follows.

Figure 9A:
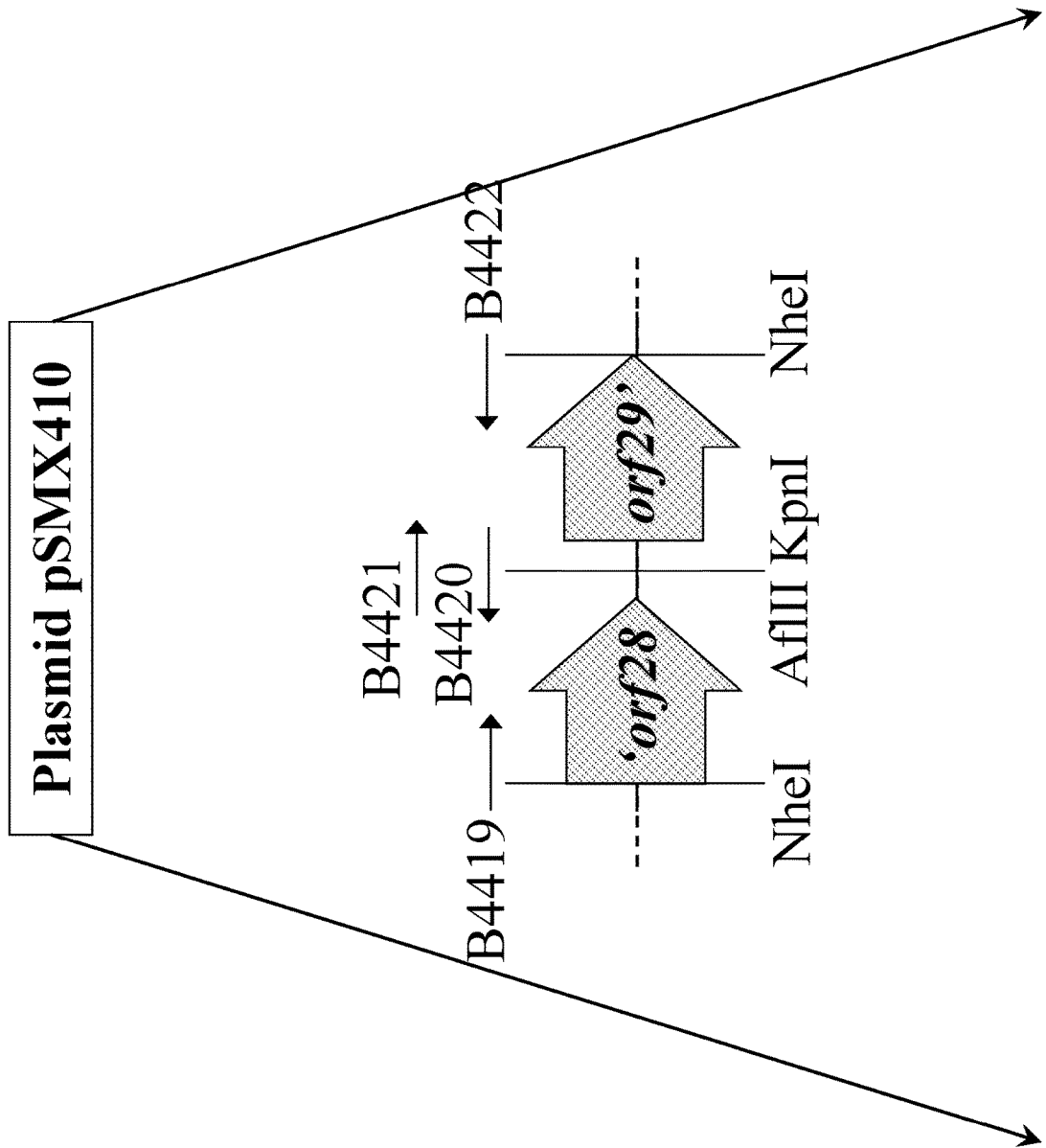
FIGS. 9A-9C are a schematic diagram showing construction of plasmids for the genetic modification of phage to add a third tail fibre hybrid gene, utilising a lacZα marker.
Figure 9B:
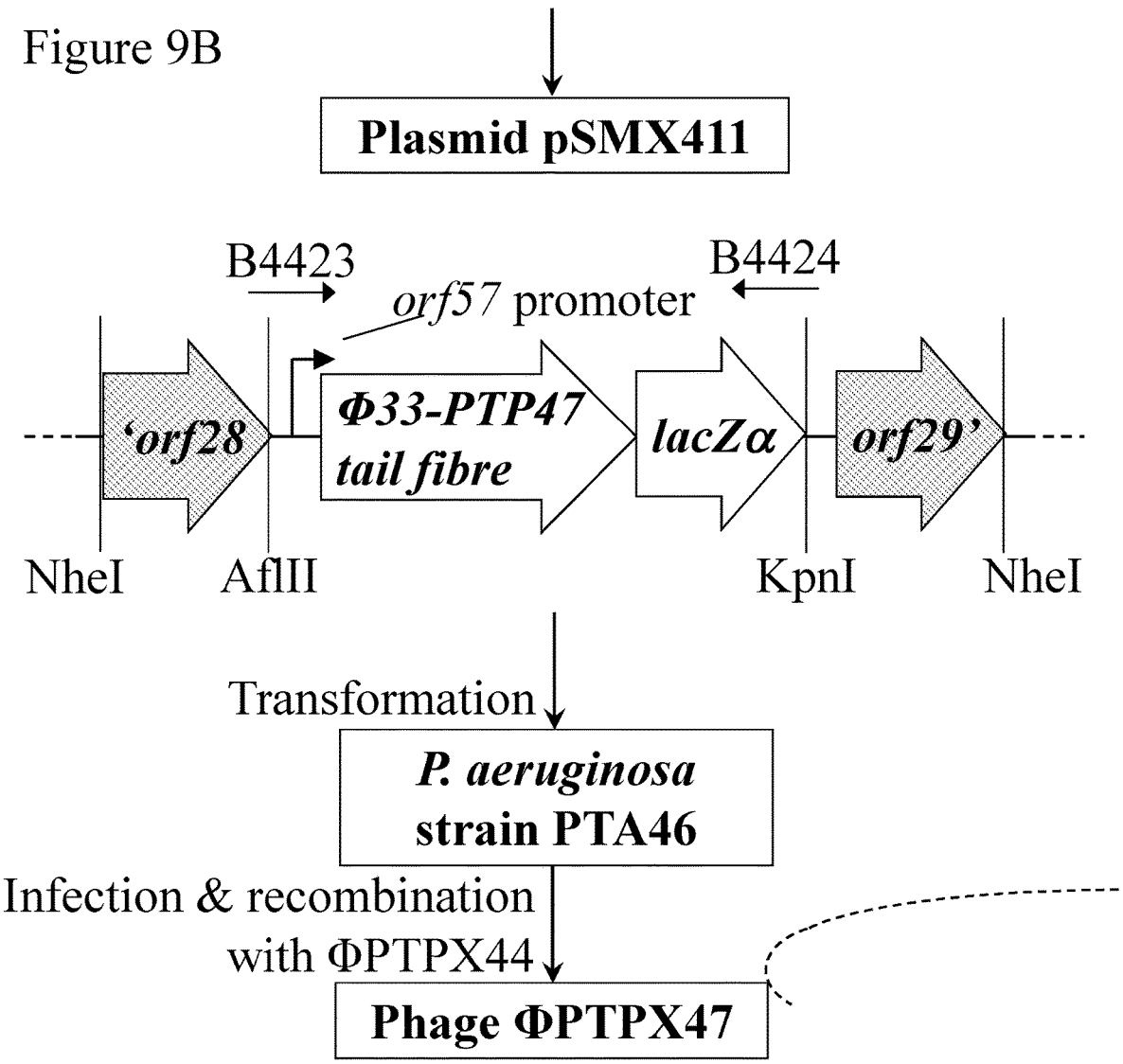
Figure 9C:
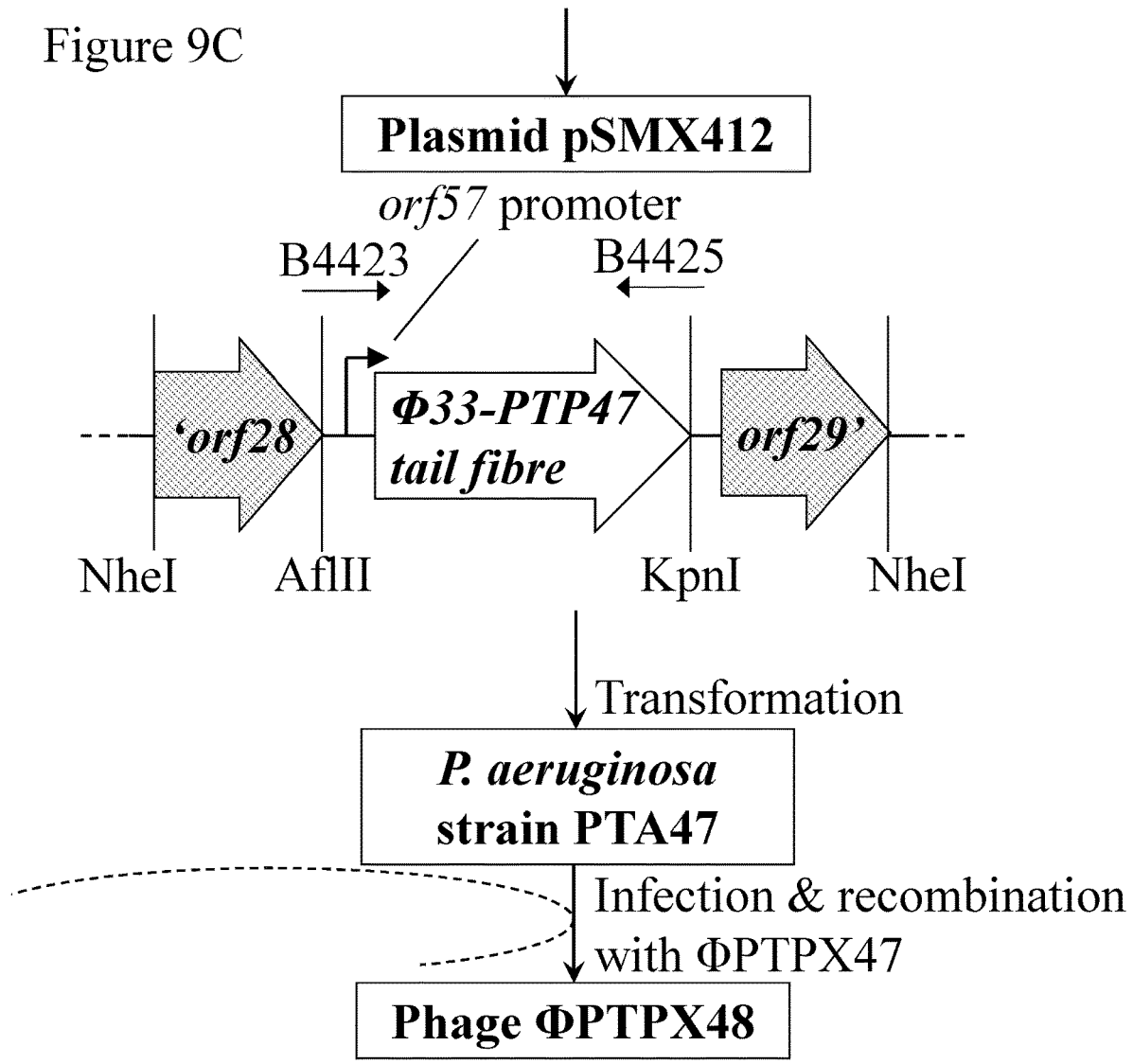

A region of Phi33 DNA flanking the end of orf28 may be amplified by PCR using primers B4419 and B4420 (FIGS. 9A-9C). A region of Phi33 DNA flanking the beginning of orf29 may be amplified by PCR using primers B4421 and B4422 (FIGS. 9A-9C). The resulting PCR products may then be joined by SOEing PCR using the outer primers, B4419 and B4422. The joined PCR product may be cleaned, digested with NheI and ligated to pSM1080 that has been digested with NheI and treated with alkaline phosphatase prior to ligation, to yield plasmid pSMX410 (FIGS. 9A-9C).

Primer B4419 consists of a 5' NheI restriction site (underlined), followed by Phi33 sequence within orf28 (FIGS. 9A-9C). Primer B4420 consists of 5' sequence complementary to that of the Phi33 orf28-orf29 intergenic region, KpnI and AflII restriction sites (underlined), followed by sequence complementary to more of the Phi33 orf28-orf29 intergenic region (FIGS. 9A-9C). Primer B4421 is the reverse complement of Primer B4420 (FIGS. 9A-9C). Primer B4422 consists of a 5' NheI restriction site (underlined), followed by Phi33 sequence complementary to the region downstream of orf29 (FIGS. 9A-9C).

```
Primer B4419
                                         (SEQ ID NO: 36)
5'-GATAGCTAGCCTGGGATTCGAAGGTTCC-3'

Primer B4420
                                         (SEQ ID NO: 37)
5'-CGAGAAAACCCGGATCGCCTGTAGGTACCTCCTTAAGTAGGATAAGG
CGTCCGGGTTTATC-3'

Primer B4421
                                         (SEQ ID NO: 38)
5'-GATAAACCCGGACGCCTTATCCTACTTAAGGAGGTACCTACAGGCGA
TCCGGGTTTTCTCG-3'

Primer B4422
                                         (SEQ ID NO: 39)
5'-GATAGCTAGCTATTCGCCCAAAAGAAAAG-3'
```

2. Plasmid pSMX411 (FIGS. 9A-9C), comprising pSMX410 carrying a gene constructed to encode the Phi33(N)PTP47(C) tail fibre, under the control of the native tail fibre promoter (Porf57), in addition to a lacZα marker, may be constructed as follows.

The DNA region comprising [Porf57-Phi33(N)PTP47(C) tail fibre gene-lacZα] may be amplified from plasmid pSMX407 (FIGS. 5A-5F), by PCR using primers B4423 and B4424 (FIGS. 9A-9C). The resulting PCR product may be digested with AflII and KpnI, and ligated to pSMX410 that has also been digested with AflII and KpnI, to yield plasmid pSMX411 (FIGS. 9A-9C).

Primer B4423 consists of a 5' AflII restriction site (underlined), followed by sequence of the Phi33 orf57 promoter (FIGS. 9A-9C). Primer B4424 consists of a 5' KpnI restriction site (underlined), followed by sequence that is complementary to the end of the lacZα marker (FIGS. 9A-9C).

```
Primer B4423
                                         (SEQ ID NO: 40)
5'-GATACTTAAGTACTGAGAAAAATCTGGATTC-3'

Primer B4424
                                         (SEQ ID NO: 41)
5'-GATAGGTACCTTAGCGCCATTCGCCATTC-3'
```

Figure 10A:
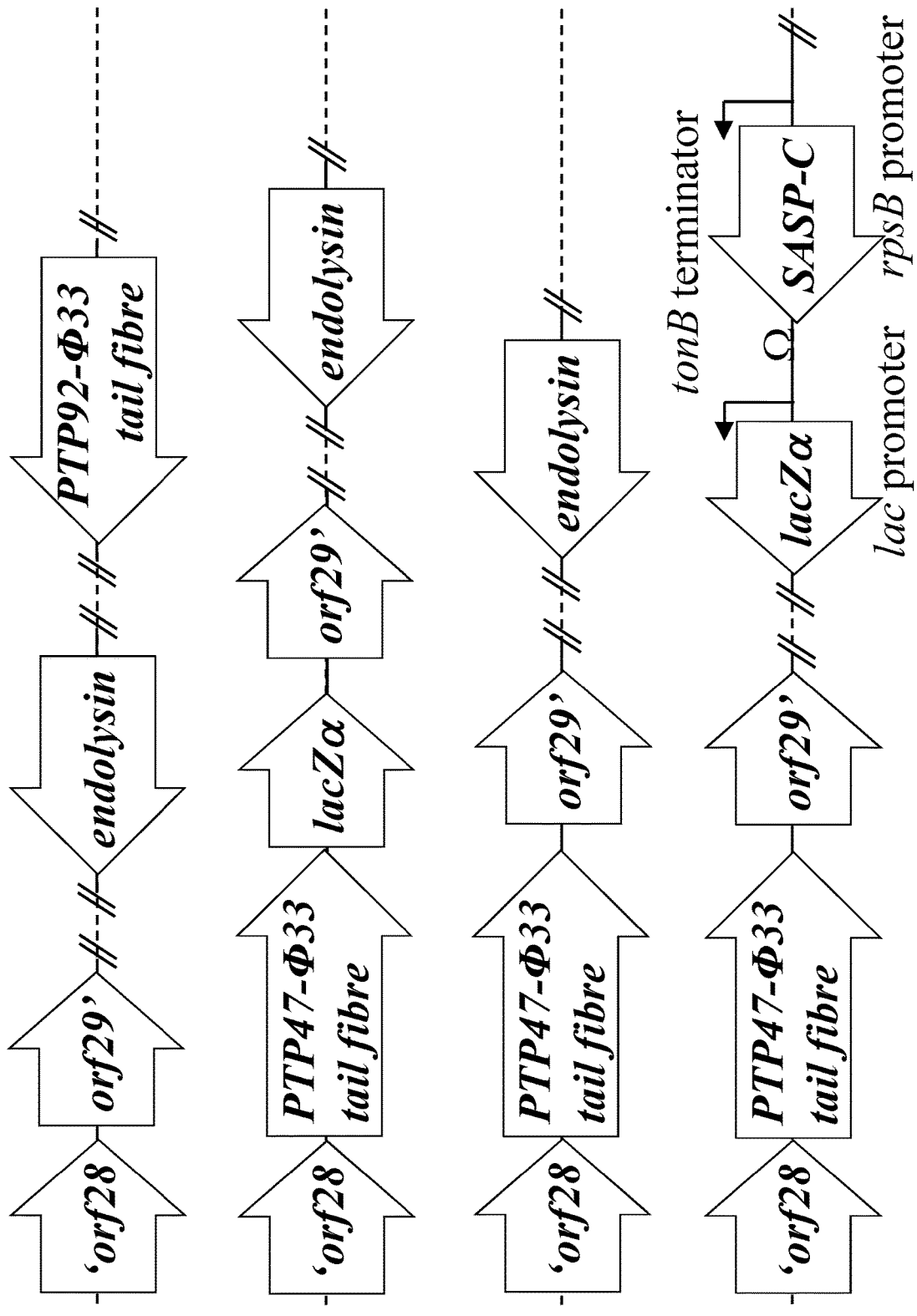
Figure 10B:
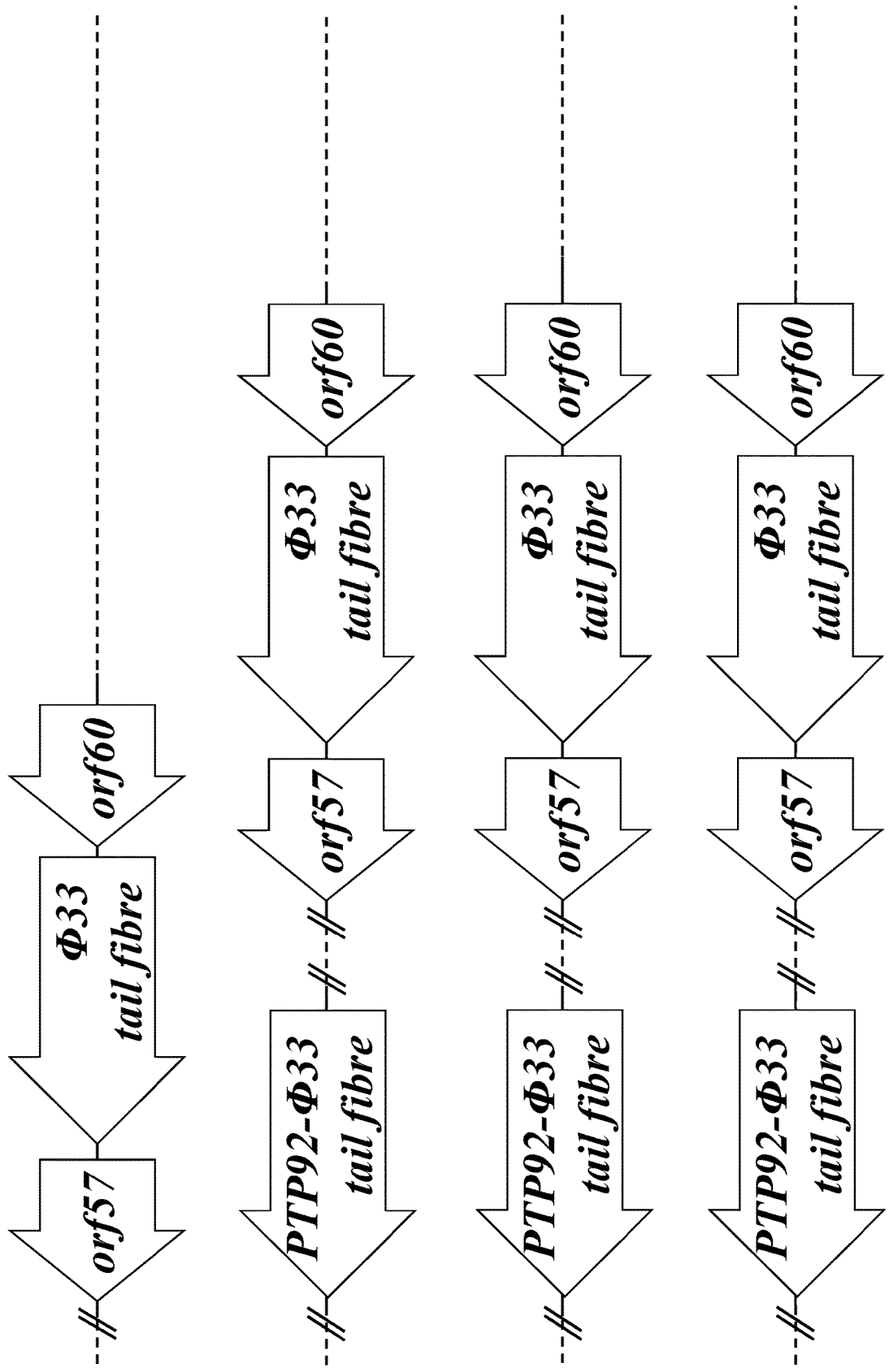
Figure 11A:
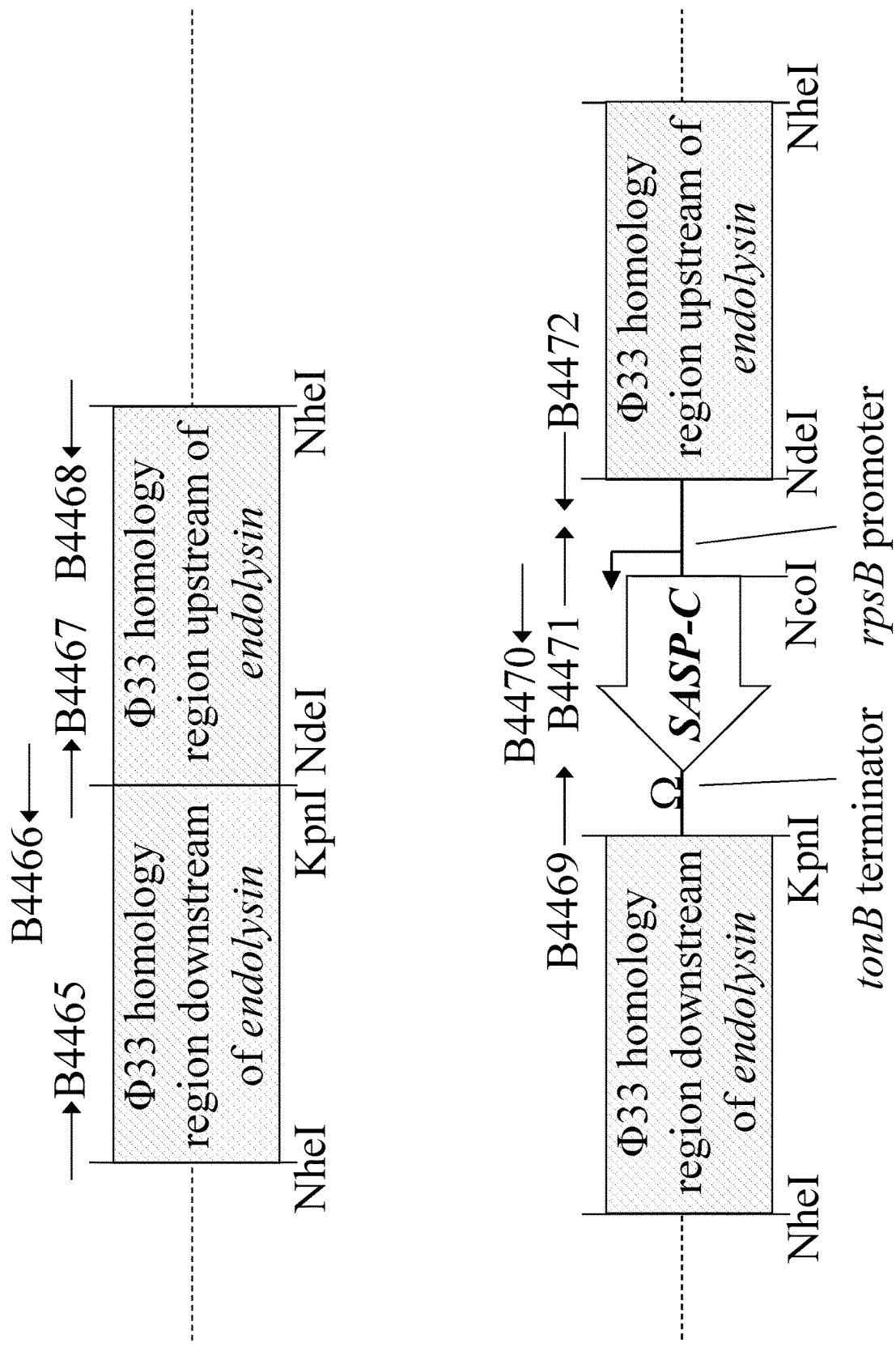
FIGS. 11A-11D are a schematic diagram showing construction of plasmids for the genetic modification production of phage to replace the endolysin gene with rpsB-SASP-C, utilising a lacZα marker.
Figure 11B:
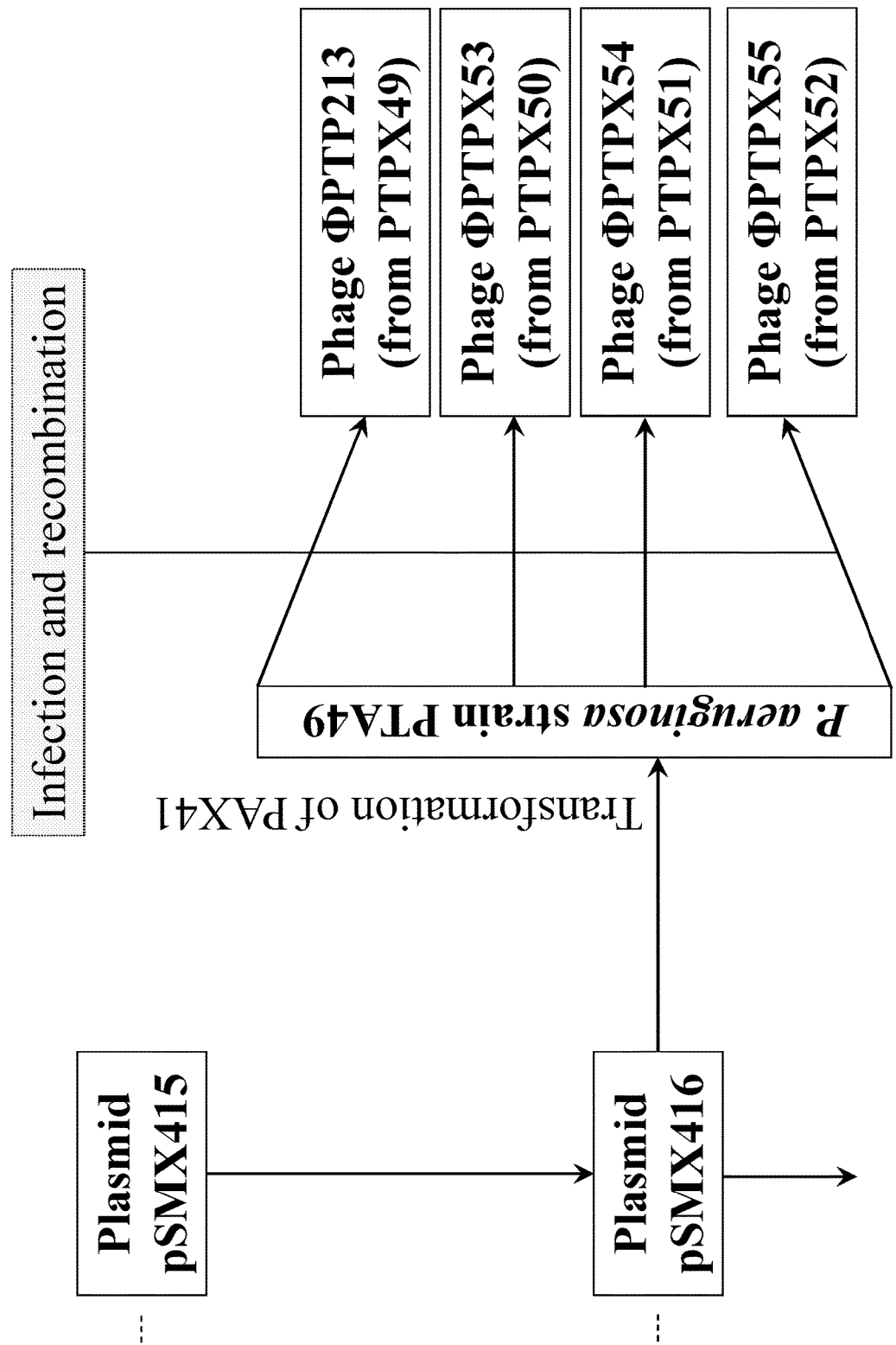
Figure 11C:
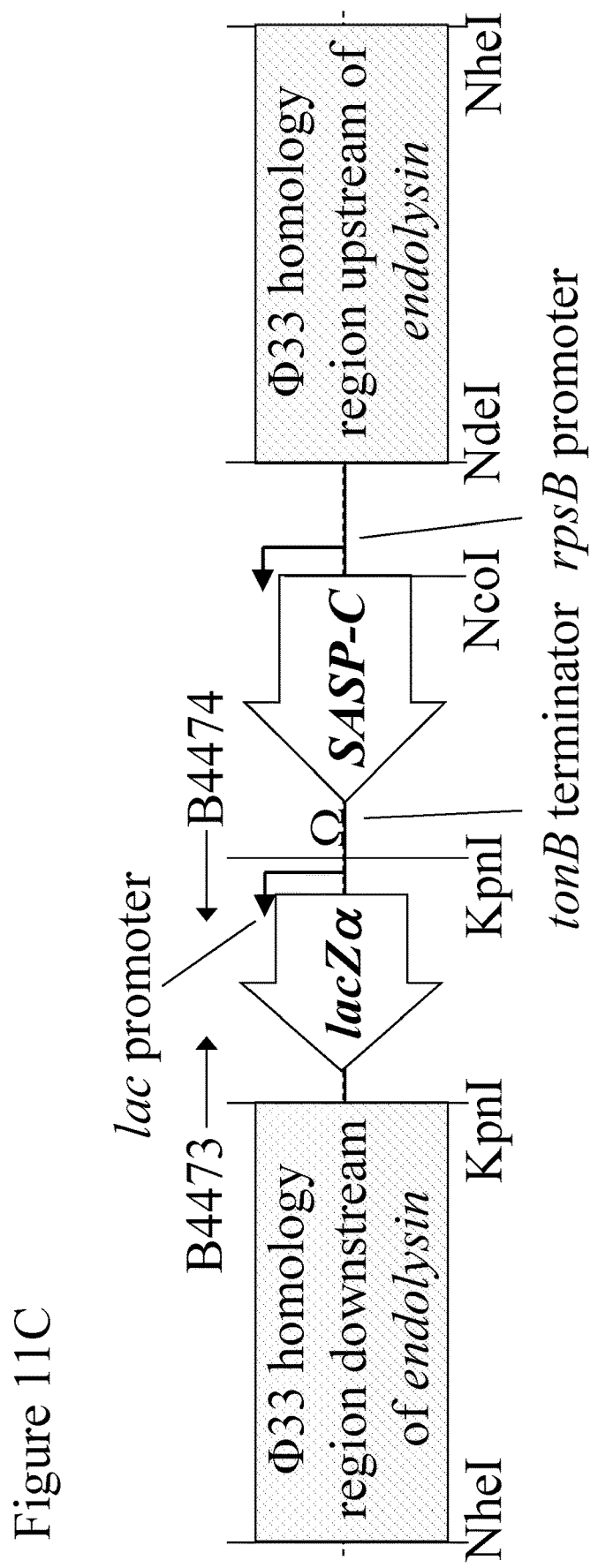
Figure 11D:
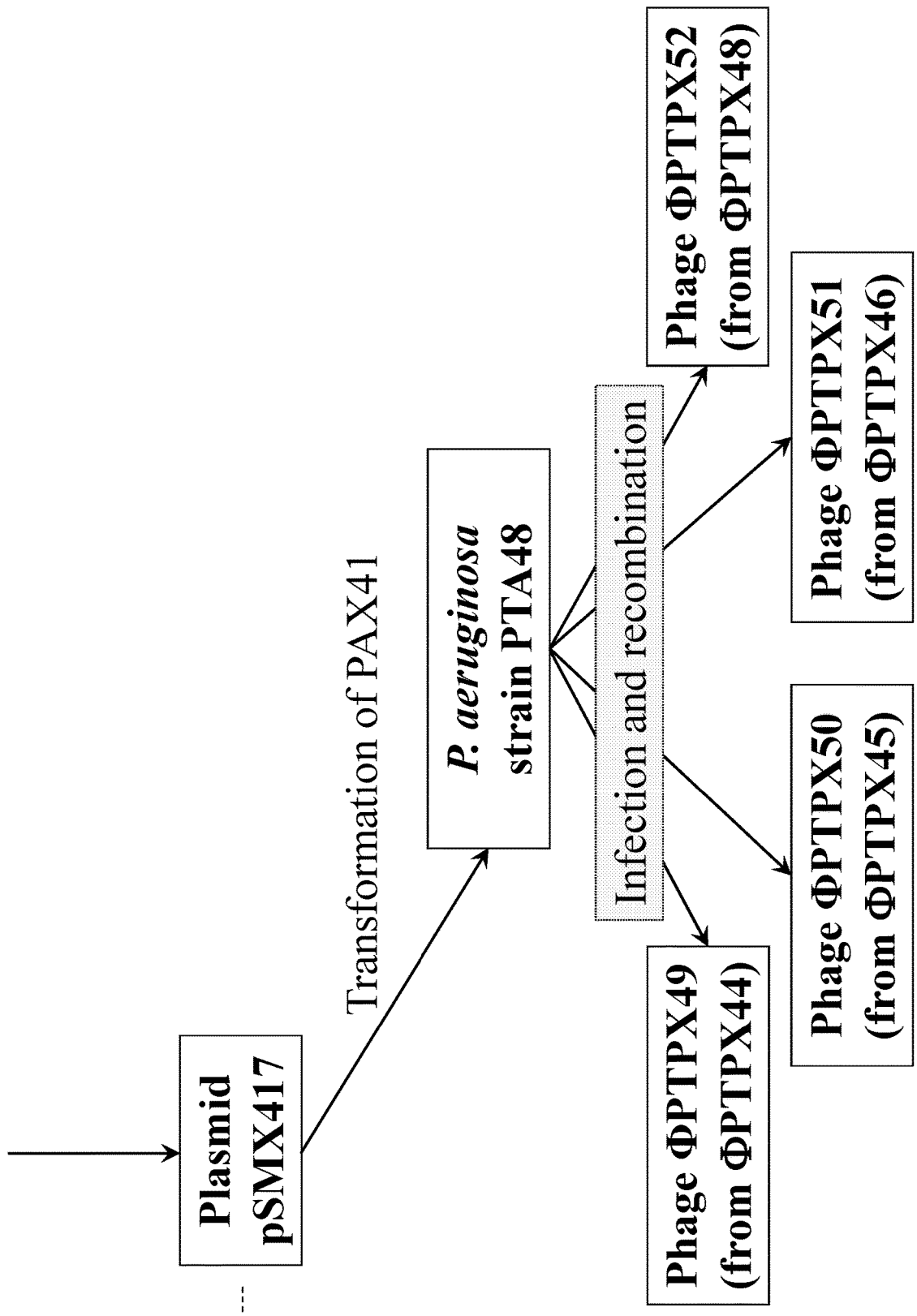

Genetic Modification of PTPX44 to Add the Phi33(N)PTP47(C) Tail Fibre Gene and a lacZα Marker, in the Intergenic Region Between Orf28 and Orf29 (Ectopic Position 2), to Generate a Bacteriophage Carrying Three Tail Fibre Genes 1. pSMX411 (FIGS. 9A-9C; FIGS. 10A-10C) may be introduced into *P. aeruginosa* strain PML14 by conjugation, selecting transconjugants on the basis of tetracycline resistance (50 µg/ml), yielding strain PTA46.

2. Strain PTA46 may be infected with PTPX44, and the progeny phage harvested.

3. Recombinant phage, which have acquired the gene encoding the Phi33(N)PTP47(C) tail fibre, in addition to the lacZα marker, in the orf28-29 intergenic region, may be identified by plaquing on *P. aeruginosa* strain PAX40 using medium containing S-gal, a chromogenic substrate that detects β-galactosidase activity, looking for black plaques.

4. PCR may be carried out to confirm that the gene encoding the Phi33(N)PTP47(C) tail fibre, in addition to the lacZα marker, has been introduced into the orf28-29 intergenic region and to confirm the presence of the gene encoding the Phi33(N)PTP92(C) tail fibre at the native position, and the native Phi33 tail fibre gene at ectopic position 1.

5. Following identification of a verified isolate (PTPX47; FIGS. 10A-10C), the new recombinant phage may be plaque purified twice more on *P. aeruginosa* strain PAX40, before further use. PTPX47 is therefore a Phi33 derivative carrying the gene encoding the Phi33(N)PTP92(C) tail fibre at the native position, the native Phi33 tail fibre gene at ectopic position 1, and the gene encoding the Phi33(N)PTP47(C) tail fibre along with a lacZα marker at ectopic position 2.

Construction of a Plasmid to Remove the lacZα Marker from the Triple-Tail Fibre Bacteriophage, PTPX47

1. Plasmid pSMX412 (FIGS. 9A-9C), comprising pSMX410 carrying the gene encoding the Phi33(N)PTP47 (C) tail fibre, under the control of the native promoter (Porf57) may be constructed as follows.

The [Porf57-Phi33(N)PTP47(C) tail fibre gene] region from pSMX407 (FIGS. 5A-5F) may be amplified by PCR using primers B4423 and B4425 (FIGS. 9A-9C). The resulting PCR product may be digested with AflII and KpnI and ligated to pSMX410 that has also been digested with AflII and KpnI, to yield plasmid pSMX412 (FIGS. 9A-9C).

Primer B4425 consists of a 5' KpnI site (underlined), followed by sequence complementary to the end of the PTP47 tail fibre gene (FIGS. 9A-9C).

Primer B4425
(SEQ ID NO: 42)
5'-GATA<u>GGTACC</u>TTACGTCACTCGCTGGAAAAG-3'

Genetic Modification of the Triple-Tail Fibre Bacteriophage, PTPX47 to Remove the lacZα Marker 1. pSMX412 (FIGS. 9A-9C; FIGS. 10A-10C) may be introduced into *P. aeruginosa* strain PML14 by conjugation, selecting transconjugants on the basis of tetracycline resistance (50 µg/ml), yielding strain PTA47.

2. Strain PTA47 may be infected with PTPX47, and the progeny phage harvested.

3. Recombinant phage, from which the lacZα marker has been removed, may be identified by plaquing on *P. aeruginosa* strain PAX40 using medium containing S-gal, a chromogenic substrate that detects β-galactosidase activity, looking for clear plaques, indicative of loss of β-galactosidase activity.

4. PCR may be carried out to confirm that the lacZα marker has been removed, and that the gene encoding the Phi33(N)PTP47(C) tail fibre is still present in the orf28-29 intergenic region (ectopic position 2), and to confirm the presence of the gene encoding the Phi33(N)PTP92(C) tail fibre at the native position, and the native Phi33 tail fibre gene at ectopic position 1.

5. Following identification of a verified isolate (PTPX48; FIGS. 10A-10C), the new recombinant phage may be plaque purified twice more on *P. aeruginosa* strain PAX40, before further use. PTPX48 is therefore a Phi33 derivative carrying the gene encoding the Phi33(N)PTP92(C) tail fibre at the native position, the native Phi33 tail fibre gene at ectopic position 1, and the gene encoding the Phi33(N)PTP47(C) tail fibre (ΔlacZα) at ectopic position 2.

Construction of a Plasmid to Generate a *P. aeruginosa* Strain Carrying the Phi33 Endolysin Gene and the *Escherichia coli* lacZΔM15 Immediately Downstream of the phoA Locus of the Bacterial Genome 1. Plasmid pSMX413 (FIGS. 1A-1C), comprising pSMX400 carrying the endolysin gene from Phi33, under the control of the native endolysin promoter, may be constructed as follows.

The endolysin promoter may be amplified by PCR from Phi33 using primers B4404 and B4405 (FIGS. 1A-1C). The endolysin gene itself may be amplified by PCR from Phi33 using primers B4406 and B4407 (FIGS. 1A-1C). The two PCR products may then be joined together by Splicing by Overlap Extension (SOEing) PCR, using the two outer primers, B4404 and B4407. The resulting PCR product may then be digested with AflII and BglII, and ligated to pSMX400 that has also been digested with AflII and BglII, to yield plasmid pSMX413 (FIGS. 1A-1C).

Primer B4404 consists of a 5' AflII restriction site (underlined), followed by a bi-directional transcriptional terminator (soxR terminator, 60-96 bases of genbank accession number DQ058714), and sequence of the beginning of the endolysin promoter region (underlined, in bold) (FIGS. 1A-1C). Primer B4405 consists of a 5' region of sequence that is complementary to the region overlapping the start codon of endolysin from Phi33, followed by sequence that is complementary to the end of the endolysin promoter region (underlined, in bold; FIGS. 1A-1C). Primer B4406 is the reverse complement of primer B4405 (see also FIGS. 1A-1C). Primer B4407 consists of a 5' BglII restriction site (underlined), followed by sequence complementary to the end of the Phi33 endolysin gene (FIGS. 1A-1C).

Primer B4404
(SEQ ID NO: 43)
5'-GATA<u>CTTAAG</u>AAAACAAACTAAAGCGCCCTTGTGGCGCTTTAGTTTTA
TACTACTGAGAAAAATCTGGATTC-3'

Primer B4405
(SEQ ID NO: 44)
5'-GATTTTCATCAATACTCCTGGATCCCGTTAATTCGAAGAGTCG-3'

Primer B4406
(SEQ ID NO: 45)
5'-CGACTCTTCGAATTAACGGGATCCAGGAGTATTGATGAAAATC-3'

Primer B4407
(SEQ ID NO: 46)
5'-GATA<u>AGATCT</u>TCAGGAGCCTTGATTGATC-3'

2. Plasmid pSMX414 (FIGS. 1A-1C), comprising pSMX413 carrying lacZΔM15 under the control of a lac promoter, may be constructed as follows.

The lacZΔM15 gene under the control of a lac promoter may be amplified by PCR from *Escherichia coli* strain DH10B using primers B4408 and B4409 (FIGS. 1A-1C). The resulting PCR product may then be digested with BglII and NheI, and ligated to pSMX413 that has also been digested with BglII and NheI, to yield plasmid pSMX414 (FIGS. 1A-1C).

Primer B4408 consists of a 5' BglII restriction site (underlined), followed by sequence of the lac promoter (FIGS. 1A-1C). Primer B4409 consists of a 5' NheI restriction site (underlined), followed by a bi-directional transcriptional terminator and sequence complementary to the 3' end of lacZΔM15 (underlined, in bold; FIGS. 1A-1C).

Primer B4408
(SEQ ID NO: 11)
5'-GATA<u>AGATCT</u>GAGCGCAACGCAATTAATGTG-3'

Primer B4409
(SEQ ID NO: 12)
5'-GATA<u>GCTAGC</u>AGTCAAAAGCCTCCGGTCGGAGGCTTTTGACT**TTATT
TTTGACACCAGACCAAC**-3'

Genetic Modification of *Pseudomonas aeruginosa* to Introduce the Phi33 Endolysin Gene and the *Escherichia coli* lacZΔM15 Allele Immediately Downstream of the phoA Locus of the Bacterial Genome 1. Plasmid pSMX414 may be transferred to *P. aeruginosa* by conjugation, selecting for primary recombinants by acquisition of resistance to tetracycline (50 µg/ml).

2. Double recombinants may then be selected via sacB-mediated counter-selection, by plating onto medium containing 10% sucrose.

3. Isolates growing on 10% sucrose may then be screened by PCR to confirm that endolysin and lacZΔM15 have been introduced downstream of the *P. aeruginosa* phoA gene.

4. Following verification of an isolate (PAX41), this strain may then be used as a host for further modification of bacteriophage, where complementation of a Δendolysin, lacZα+ genotype is required.

Construction of a Plasmid to Replace the Endolysin Gene of the Double-Tail Fibre Phage (PTPX44, PTPX45, PTPX46), or Similar Bacteriophage, or the Triple-Tail Fibre Phage (PTPX48), or Similar Bacteriophage, with rpsB-SASP-C and lacZα

1. Plasmid pSMX415 (FIGS. 11A-11D), comprising pSM1080 containing regions of Phi33 flanking the endolysin gene, may be constructed as follows.

The region of Phi33 sequence immediately downstream of the endolysin gene may be amplified by PCR using primers B4465 and B4466 (FIGS. 11A-11D). This PCR product may then be cleaned and digested with NdeI and NheI. The region of Phi33 sequence immediately upstream of the endolysin gene may be amplified by PCR using primers B4467 and B4468 (FIGS. 11A-11D). This second PCR product may then be cleaned and digested with NdeI and NheI. The two PCR product digests may then be cleaned again and ligated to pSM1080 that has been digested with NheI and treated with alkaline phosphatase prior to ligation. Clones carrying one insert of each of the two PCR products may be identified by PCR using primers B4465 and B4468, and by restriction digest of the purified plasmid DNA with NdeI, to identify plasmid pSMX415 (FIGS. 11A-11D).

Primer B4465 consists of a 5' NheI restriction site (underlined), followed by Phi33 sequence located approximately 340 bp downstream of the Phi33 endolysin gene (FIGS. 11A-11D). Primer B4466 consists of 5' NdeI and KpnI restriction sites (underlined), followed by sequence of Phi33 that is located immediately downstream of the endolysin gene (FIGS. 11A-11D). Primer B4467 consists of a 5' NdeI restriction site (underlined), followed by sequence that is complementary to sequence located immediately upstream of the Phi33 endolysin gene (FIGS. 11A-11D). Primer B4468 consists of a 5' NheI site (underlined), followed by Phi33 sequence that is located approximately 340 bp upstream of the endolysin gene (FIGS. 11A-11D).

```
Primer B4465
                                         (SEQ ID NO: 47)
5'-GATAGCTAGCTTGGCCAGAAAGAAGGCG-3'

Primer B4466
                                         (SEQ ID NO: 48)
5'-GATACATATGTCGGTACCTATTCGCCCAAAAGAAAAG-3'

Primer B4467
                                         (SEQ ID NO: 49)
5'-GATACATATGTCAATACTCCTGATTTTTG-3'

Primer B4468
                                         (SEQ ID NO: 50)
5'-GATAGCTAGCAATGAAATGGACGCGGATC-3'
```

2. Plasmid pSMX416 (FIGS. 11A-11D), comprising pSMX415 containing SASP-C under the control of an rpsB promoter, may be constructed as follows.

The SASP-C gene from *Bacillus megaterium* strain KM (ATCC 13632) may be amplified by PCR using primers B4469 and B4470 (FIGS. 11A-11D). The resulting PCR product may then be digested with KpnI and NcoI. The rpsB promoter may be amplified by PCR from *P. aeruginosa* using primers B4471 and B4472 (FIGS. 11A-11D). The resulting PCR product may then be digested with NcoI and NdeI. The two digested PCR products may then be cleaned and ligated to pSMX415 that has been digested with KpnI and NdeI, yielding plasmid pSMX416 (FIGS. 11A-11D).

Primer B4469 comprises a 5' KpnI restriction site, followed by a bi-directional transcriptional terminator, and then sequence complementary to the 3' end of the SASP-C gene from *B. megaterium* strain KM (ATCC 13632) (underlined, in bold; FIGS. 11A-11D). Primer B4470 comprises a 5' NcoI restriction site (underlined), followed by sequence of the 5' end of the SASP-C gene from *B. megaterium* strain KM (ATCC 13632) (FIGS. 11A-11D). Primer B4471 comprises a 5' NcoI restriction site (underlined), followed by sequence complementary to the end of the rpsB promoter from *P. aeruginosa* PAO1 (FIGS. 11A-11D). Primer B4472 comprises a 5' NdeI restriction site (underlined), followed by sequence of the beginning of the rpsB promoter from *P. aeruginosa* PAO1 (FIGS. 11A-11D).

```
Primer B4469
                                         (SEQ ID NO: 51)
5'-GATAGGTACCGATCTAGTCAAAAGCCTCCGACCGGAGGCTTTTGACT
TTAGTACTTGCCGCCTAG-3'

Primer B4470
                                         (SEQ ID NO: 52)
5'-GATACCATGGCAAATTATCAAAACGCATC-3'

Primer B4471
                                         (SEQ ID NO: 53)
5'-GATACCATGGTAGTTCCTCGATAAGTCG-3'

Primer B4472
                                         (SEQ ID NO: 54)
5'-GATACATATGCCTAGGGATCTGACCGACCGATCTACTCC-3'
```

3. Plasmid pSMX417 (FIGS. 11A-11D), comprising pSMX416 containing lacZα, may be constructed as follows.

lacZα may be PCR amplified using primers B4473 and B4474 (FIGS. 11A-11D). The resulting PCR product may then be digested with KpnI and ligated to pSMX416 that has also been digested with KpnI and treated with alkaline phosphatase prior to ligation, to yield pSMX417 (FIGS. 11A-11D).

Primer B4473 consists of a 5' KpnI restriction site (underlined), followed by sequence complementary to the 3' end of lacZα (FIGS. 11A-11D). Primer B4474 consists of a 5' KpnI restriction site (underlined), followed by sequence of the lac promoter driving expression of lacZα (FIGS. 11A-11D).

```
Primer B4473
                                         (SEQ ID NO: 55)
5'-GATAGGTACCTTAGCGCCATTCGCCATTC-3'

Primer B4474
                                         (SEQ ID NO: 56)
5'-GATAGGTACCGCGCAACGCAATTAATGTG-3'
```

Genetic Modification of the Double-Tail Fibre Phage (PTPX44, PTPX45, PTPX46), or Similar Bacteriophage, or the Triple-Tail Fibre Phage (PTPX48), or Similar Bacteriophage, to Replace Endolysin with rpsB-SASP-C and lacZα

1. Plasmid pSMX417 (FIGS. 11A-11D) may be introduced into *P. aeruginosa* strain PAX41 by conjugation, selecting transconjugants on the basis of tetracycline resistance (50 μg/ml), yielding strain PTA48.

2. Strain PTA48 may be infected in individual experiments with one of the double-tail fibre phage (PTPX44 (FIGS. 6A-6C), PTPX45 (FIGS. 7A-7C), PTPX46 (FIGS. 8A-8C)), or similar bacteriophage, or the triple-tail fibre phage (PTPX48; FIGS. 10A-10C), or similar bacteriophage, and the progeny phage harvested.

3. Recombinant phage, in which the endolysin gene has been replaced by rpsB-SASP-C and lacZα, may be identified by plaquing the lysate from step (2) on *P. aeruginosa* strain PAX41, onto medium containing S-gal, looking for black plaques, which are indicative of β-galactosidase activity.

4. PCR may be carried out to check that the endolysin gene has been replaced, and that rpsB-SASP-C and lacZα are present.

5. Following identification of verified isolates (for example, PTPX49 (FIGS. 6A-6C), PTPX50 (FIGS. 7A-7C), PTPX51 (FIGS. 8A-8C), PTPX52 (FIGS. 10A-10C), the isolates may be plaque purified twice more on *P. aeruginosa* strain PAX41, prior to further use.

Genetic Modification to Remove the lacZα Marker from PTPX49, PTPX50, PTPX51, PTPX52 and Similar Derivatives of Phi33 that Carry rpsB-SASP-C in Place of the Endolysin Gene 1. Plasmid pSMX416 (FIGS. 11A-11D) may be introduced into *P. aeruginosa* strain PAX41 by conjugation, selecting transconjugants on the basis of tetracycline resistance (50 μg/ml), yielding strain PTA49.

2. Strain PTA49 may be infected in individual experiments with phage PTPX49, or PTPX50, or PTPX51, or PTPX52, or other similar phage, and the progeny phage harvested.

3. Recombinant phage, in which lacZα marker has been removed, may be identified by plaquing the lysate from step (2) on *P. aeruginosa* strain PAX41, onto medium containing S-gal, looking for clear plaques, which are indicative of loss of D-galactosidase activity.

4. PCR may be carried out to confirm removal of the lacZα marker, while ensuring that rpsB-SASP-C is still present.

Figure 12A:
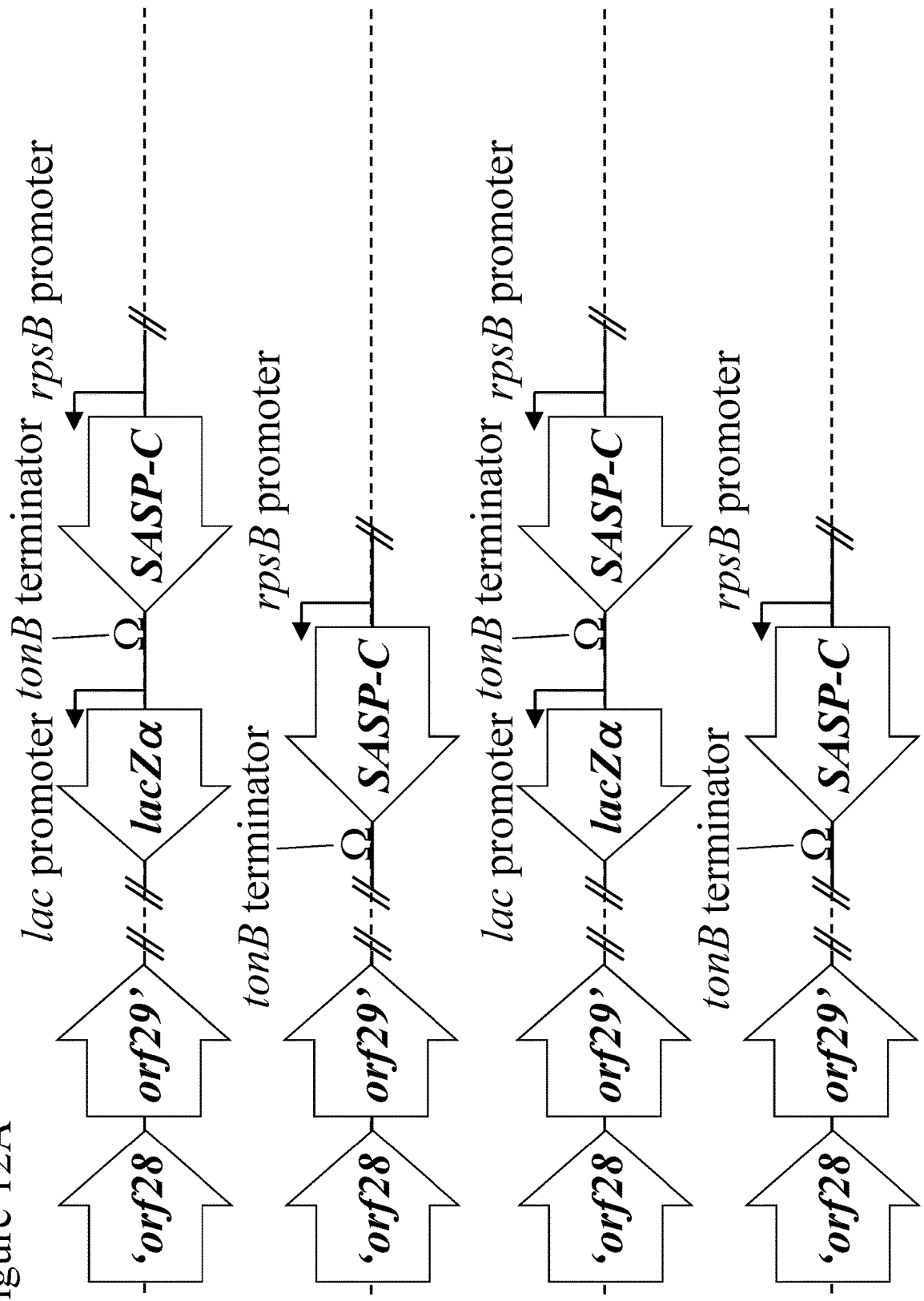
Figure 12B:
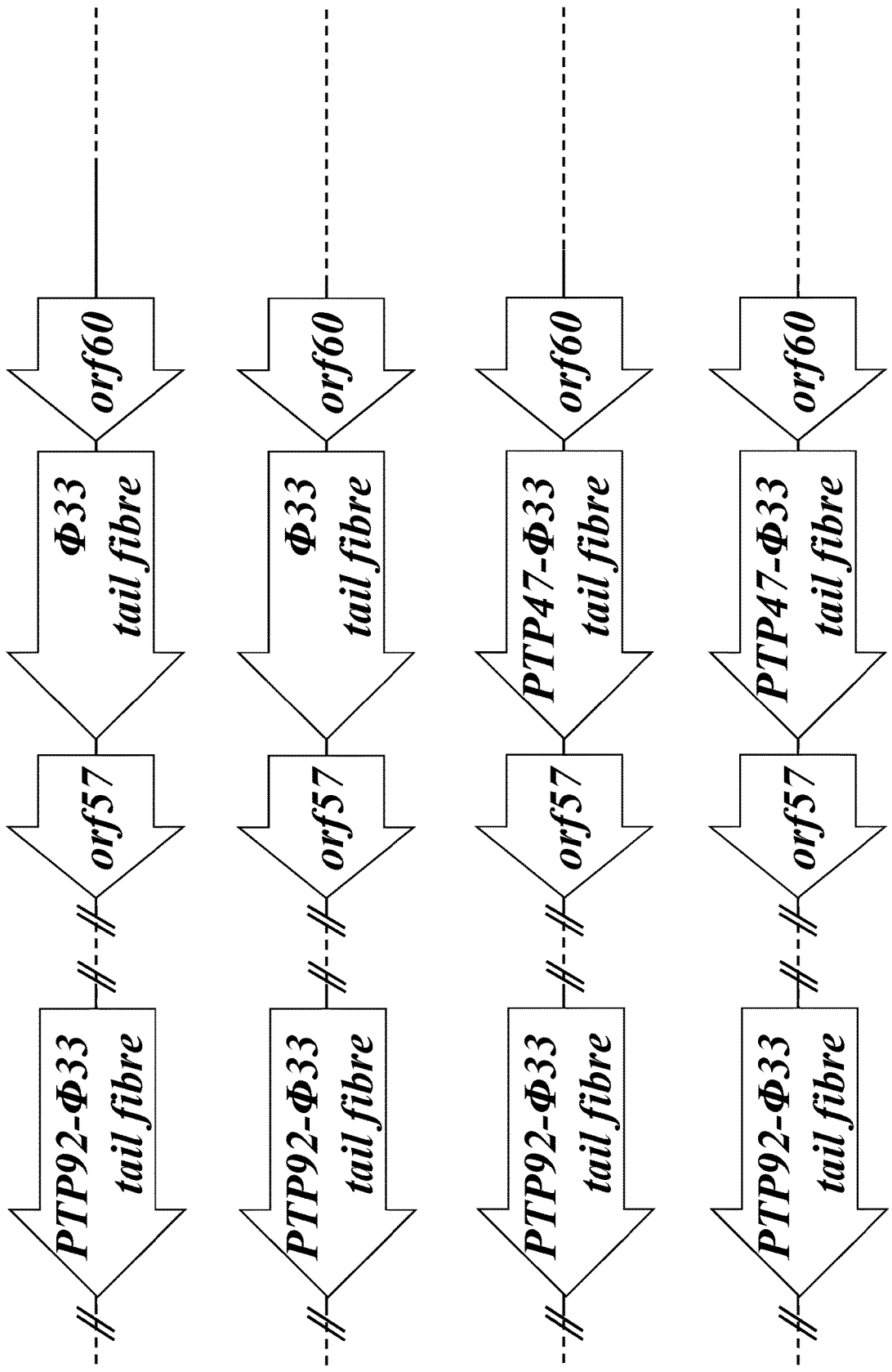

5. Following identification of verified isolates (for example, PTP213 (FIGS. 11A-11D; FIGS. 12A-12C), PTPX53 (FIGS. 11A-11D; FIGS. 12A-12C), PTPX54 (FIGS. 11A-11D; FIGS. 13A-13C), PTPX55 (FIGS. 11A-11D; FIGS. 13A-13C)), the isolates may be plaque purified twice more on *P. aeruginosa* strain PAX41, prior to further use.

TABLE 1

Host range of Phi33, PTP92, C36 and PTP47 against 44 European clinical isolates of *Pseudomonas aeruginosa*.

| Bacterial Strain no. | Phi33 | PTP47 | PTP92 | C36 |
|---|---|---|---|---|
| 2019 | + | + | − | + |
| 2020 | + | + | − | + |
| 2021 | + | + | + | + |
| 2029 | + | + | − | + |
| 2031 | + | + | + | + |
| 2039 | + | + | + | + |
| 2040 | + | + | − | + |
| 2041 | + | + | + | + |
| 2042 | + | + | + | + |
| 2045 | − | − | + | − |
| 2046 | + | + | + | + |
| 2047 | + | + | + | + |
| 2048 | + | + | + | + |
| 2049 | + | + | + | + |
| 2050 | + | + | + | + |
| 2051 | + | + | − | − |
| 2052 | − | − | − | − |
| 2053 | + | + | − | + |
| 2054 | − | + | − | + |
| 2055 | + | + | − | + |
| 2056 | + | + | + | + |
| 2057 | + | + | + | + |
| 2058 | + | + | + | + |
| 2483 | − | − | + | − |
| 2484 | + | + | − | + |
| 2705 | + | + | − | + |
| 2706 | + | + | − | + |
| 2707 | + | + | + | + |
| 2708 | + | + | + | + |
| 2709 | + | + | + | + |
| 2710 | − | + | + | − |
| 2711 | + | + | + | + |
| 2712 | + | + | − | + |
| 2713 | − | + | + | + |
| 2714 | + | + | + | + |
| 2715 | + | + | + | + |
| 2716 | + | + | − | − |
| 2717 | − | + | + | + |
| 2718 | − | + | + | + |
| 2719 | + | + | − | + |
| 2720 | + | + | + | + |
| 2721 | + | + | + | + |
| 2722 | + | + | + | + |
| 2723 | + | + | − | + |

Strains were tested for sensitivity to each phage by dropping 10 μl of crude phage lysate onto a soft agar overlay plate inoculated with bacteria. Plates were grown overnight at 32° C. and the strains were scored for sensitivity to each phage by assessing clearance zones at the point of inoculation. Where phage inhibited growth, as seen by clearance of the bacterial lawn, the strain was marked as sensitive (+), and where no inhibition of growth was seen, the strain was marked as not-sensitive (−)

TABLE 2

Host range of Phi33, PTP92 and PTP93 against 35 European clinical isolates of *Pseudomonas aeruginosa*.

| Isolate | Phi33 | PTP93 | PTP92 |
|---|---|---|---|
| 2019 | + | + | − |
| 2020 | + | + | − |
| 2029 | + | + | − |
| 2040 | + | + | − |
| 2045 | − | + | + |
| 2053 | + | + | − |
| 2483 | − | + | + |
| 2484 | + | + | − |
| 2705 | + | − | − |
| 2710 | − | + | + |
| 2711 | + | + | + |
| 2712 | + | + | − |
| 2713 | − | + | + |
| 2716 | + | + | − |
| 2717 | − | + | + |
| 2718 | − | + | + |
| 2720 | + | + | + |
| 2721 | + | + | + |
| 2722 | + | + | + |
| 2723 | + | − | − |
| 2728 | − | + | + |
| 2733 | + | + | − |
| 2734 | + | + | + |
| 2740 | − | + | + |
| 2741 | + | + | + |
| 2742 | + | + | + |
| 2743 | + | + | + |
| 2747 | + | + | + |
| 2748 | + | + | + |
| 2749 | + | + | − |
| 2750 | + | + | + |

TABLE 2-continued

Host range of Phi33, PTP92 and PTP93 against 35 European clinical isolates of *Pseudomonas aeruginosa*.

| Isolate | Phi33 | PTP93 | PTP92 |
|---|---|---|---|
| 2752 | + | + | + |
| 2753 | − | + | + |
| 2754 | + | + | + |
| 2756 | + | + | + |

Strains were tested for sensitivity to each phage by dropping 10 µl of crude phage lysate onto a soft agar overlay plate inoculated with bacteria. Plates were grown overnight at 32° C. and the strains were scored for sensitivity to each phage by assessing clearance zones at the point of inoculation. Where phage inhibited growth, as seen by clearance of the bacterial lawn, the strain was marked as sensitive (+), and where no inhibition of growth was seen, the strain was marked as not-sensitive (−)

TABLE 3

Host range of PTP213, Phi33, and PTP92 against 9 clinical isolates of *Pseudomonas aeruginosa*.

| Isolate | PTP213 | Phi33 | PTP92 |
|---|---|---|---|
| 2055 | + | + | − |
| 2710 | + | − | + |
| 2948 | + | + | − |
| 2967 | + | − | + |
| 2975 | + | − | + |
| 2992 | + | − | + |
| 3183 | + | − | + |
| 3193 | + | − | + |
| 3207 | + | + | + |

Strains were tested for sensitivity to each phage by dropping 10 µl of crude phage lysate onto a soft agar overlay plate inoculated with bacteria. Plates were grown overnight at 32° C. and the strains were scored for sensitivity to each phage by assessing clearance zones at the point of inoculation. Where phage inhibited growth, as seen by clearance of the bacterial lawn, the strain was marked as sensitive (+), and where no inhibition of growth was seen, the strain was marked as not-sensitive (−)

REFERENCES

Abedon S T. (2008). Bacteriophage Ecology: Population Growth, Evolution, an Impact of Bacterial Viruses. Cambridge. Cambridge University Press. Chapter 1.

Boucher, H. W., Talbot, G. H., Bradley, J. S., Edwards, J. E., Gilbert, D., Rice. L. B., & Bartlett, J. (2009). Bad bugs, no drugs: no ESKAPE! An update from the Infectious Diseases Society of America. *Clinical Infectious Diseases*, 48: 1-12.

Burrowes, B., & Harper. D. R. (2012). 14 Phage Therapy of Non-wound Infections. *Bacteriophages in Health and Disease: Bacteriophages in Health and Disease*, 203.

Carlton, R. M. (1999). Phage therapy: past history and future prospects. *Archivum Immunologiae et Therapiae Experimentalis—English Edition* 47:267-274.

Ceyssens P, Miroshnikov K, Mattheus W, Krylov V, Robben J, Noben J, Vanderschraeghe S, Sykilinda N, Kropinski A M, Volckaert G, Mesyanzhinov V, Lavigne R, (2009). Comparative analysis of the widespread and conserved PB1-like viruses infecting *Pseudomonas aeruginosa*. *Env. Microbiol.*, 11:2874-2883.

Francesconi, S. C., MacAlister, T. J., Setlow, B., & Setlow, P. (1988). Immunoelectron microscopic localization of small, acid-soluble spore proteins in sporulating cells of *Bacillus subtilis*. *J Bacteriol.*, 170: 5963-5967.

Frenkiel-Krispin, D., Sack, R., Englander, J., Shimoni, E., Eisenstein, M., Bullitt, E. & Wolf, S. G. (2004). Structure of the DNA-SspC complex: implications for DNA packaging, protection, and repair in bacterial spores. *J. Bacteriol.* 186:3525-3530.

Gill J J, Hyman P. (2010). Phage Choice, Isolation and Preparation for Phage therapy. *Current Pharmaceutical Biotechnology.* 11:2-14.

Kutateladze, M., & Adamia, R. (2010). Bacteriophages as potential new therapeutics to replace or supplement antibiotics. *Trends Biotechnol.* 28:591-595.

Lee, K. S., Bumbaca, D., Kosman. J., Setlow, P., & Jedrzejas, M. J. (2008). Structure of a protein-DNA complex essential for DNA protection in spores of *Bacillus* species. *Proc. Nat. Acad. Sci.* 105:2806-2811.

Nicholson W L, Setlow B, Setlow P. (1990). Binding of DNA in vitro by a small, acid-soluble spore protein from *Bacillus subtilis* and the effect of this binding on DNA topology. *J Bacteriol.* 172:6900-6906.

Rakhuba D V, Kolomiets E I, Szwajcer Dey E, Novik E I. (2010). Bacteriophage Receptors, Mechanisms of Phage Adsorption and Penetration into Host Cell. *Polish J. Microbio.*, 59:145-155.

Sambrook, J., Fritsch, E. F., & Maniatis, T. (1989). *Molecular cloning* (Vol. 2, pp. 14-9). New York: Cold Spring Harbor Laboratory Press.

Scholl, D., Rogers. S., Adhya, S., & Merril, C. R. (2001). Bacteriophage K1-5 encodes two different tail fiber proteins, allowing it to infect and replicate on both K1 and K5 strains of *Escherichia coli. J Virol.* 75:2509-2515.

Veesler D, Cambillau C. (2011). A Common Evolutionary Origin for Tailed-Bacteriophage *Functional* Modules and Bacterial Machineries. *Microbiol Mol Biol Rev.* 75:423-433.

Walker. B., Barrett. S., Polasky, S., Galaz, V., Folke, C., Engstrom, G., & de Zeeuw. A. (2009). Looming global-scale failures and missing institutions. *Science,* 325:1345-1346.

WHO (2014) Antimicrobial resistance: global report on surveillance 2014.

The invention claimed is:

1. A modified bacteriophage capable of infecting a plurality of different target bacteria, which bacteriophage includes an α/β small acid-soluble spore protein (SASP) gene encoding a SASP which is toxic to the target bacteria; wherein the bacteriophage is non-lytic; wherein the bacteriophage expresses a plurality of different host range determinants; and wherein each host range determinant has a different bacterial host specificity, wherein each host range determinant comprises a tail fibre protein, wherein each host range determinant comprises a tail fibre protein which comprises a receptor binding region for binding to the target bacteria and a region linking the receptor binding region to the body of the bacteriophage, and wherein each tail fibre protein is from a *Pseudomonas* bacteriophage.

2. The modified bacteriophage according to claim 1, wherein the bacterial host specificity of the host range determinant is within the same bacterial species.

3. The modified bacteriophage according to claim 1, which comprises an inactivated lysis gene, or a lysis gene which is inactivated by insertion of the SASP gene, optionally wherein the SASP is SASP-C, or optionally wherein the SASP is SASP-C from *Bacillus megaterium*.

4. The modified bacteriophage according to claim 1, wherein the SASP gene is under the control of a constitutive promoter, or a constitutive promoter which drives production of toxic levels of SASP when the modified bacteriophage is present in multiple copies in the target bacterium, and/or a promoter selected from pdhA, rpsB, pgi, fda, lasB and promoters having more than 90% sequence identity thereto.

5. The modified bacteriophage according to claim 1, wherein at least one of the target bacteria is *Pseudomonas*, or wherein the plurality of different target bacteria is a plurality of different *Pseudomonas* bacteria, and/or wherein the *Pseudomonas* bacteria comprise *Pseudomonas aeruginosa*.

6. A modified bacteriophage capable of infecting a plurality of different target bacteria, wherein the bacteriophage expresses a plurality of different host range determinants each comprising a tail fibre which comprises a receptor binding region for binding to the target bacteria and a linking region that links the receptor binding region to the body of the bacteriophage, wherein each host range determinant has a different bacterial host specificity, and wherein the receptor binding region is a C-terminal receptor binding region and the region linking the C-terminal receptor binding region to the body of the bacteriophage is an N-terminal region, which bacteriophage includes an α/β small acid-soluble spore protein (SASP) gene encoding a SASP which is toxic to the target bacteria, wherein the N-terminal region comprises amino acids 1 to 628 of the tail fibre protein and the C-terminal region comprises amino acids 629 to 964 of the tail fibre protein, based on the amino acid sequence of bacteriophage Phi33, and/or wherein the C-terminal region has no more than 96% amino acid sequence identity with the C-terminal region of bacteriophage Phi33.

7. The modified bacteriophage according to claim 6, wherein the C-terminal region is from any one of bacteriophage Phi33, LBL3, SPM-1, F8, PB1, KPP12, LMA2, SN, 14-1, JG024, NH4, PTP47, PTP92, C36 and PTP93.

8. The modified bacteriophage according to claim 7, wherein the C-terminal region amino sequence identity is less than 80%, or less than 70%, or less than 60% with the C-terminal region of bacteriophage Phi33.

9. The modified bacteriophage according to claim 6, wherein the N-terminal region has at least 95% amino acid sequence identity with the N-terminal region of bacteriophage Phi33.

10. The modified bacteriophage according to claim 9, wherein the N-terminal region is from any one of bacteriophage Phi33, LBL3, SPM-1, F8, PB1, KPP12, LMA2, SN, 14-1, JG024, NH4, PTP47, PTP92, C36 and PTP93.

11. The modified bacteriophage according to claim 1, wherein said *Pseudomonas* bacteriophage is selected from the group consisting of PB1-like, Phi33, LBL3, SPM-1, F8, PB1, KPP12, LMA2, SN, 14-1, JG024, NH4, PTP47, PTP92, C36 and PTP93.

12. The modified bacteriophage according to claim 1 in admixture with at least one other modified bacteriophage which is capable of infecting target bacteria, which includes a SASP gene encoding a SASP which is toxic to the target bacteria and which is non-lytic.

13. A composition for inhibiting or preventing bacterial cell growth, which comprises a modified bacteriophage according to claim 1, and a carrier therefor, wherein the composition is optionally formulated for pharmaceutical use and/or topical use.

14. The modified bacteriophage of claim 1, wherein at least one of said tail fibres comprises a receptor binding region of one *Pseudomonas* bacteriophaqe and a linking region from a different *Pseudomonas* bacteriophage.

15. The modified bacteriophage according to claim 1, wherein at least one of said tail fibres comprises an N-terminal region having at least 95% amino acid sequence identity to amino acids 1 to 628 of the tail fibre protein of bacteriophage Phi33, and a C-terminal region having no more than 96% amino acid sequence identity to amino acids 629 to 964 of the tail fibre protein of bacteriophage Phi33.

* * * * *

SEQUENCE LISTING

<160> NUMBER OF SEQ ID NOS: 70

<210> SEQ ID NO 1
<211> LENGTH: 18
<212> TYPE: DNA
<213> ORGANISM: Artificial Sequence
<220> FEATURE:
<223> OTHER INFORMATION: primer B4500

<400> SEQUENCE: 1
gtgatcacac ccgaactg                                                 18

<210> SEQ ID NO 2

```
<211> LENGTH: 22
<212> TYPE: DNA
<213> ORGANISM: Artificial Sequence
<220> FEATURE:
<223> OTHER INFORMATION: primer B4501

<400> SEQUENCE: 2
cgatgaagaa gagttggttt tg                                              22

<210> SEQ ID NO 3
<211> LENGTH: 20
<212> TYPE: DNA
<213> ORGANISM: Artificial Sequence
<220> FEATURE:
<223> OTHER INFORMATION: primer B4502

<400> SEQUENCE: 3
acgccggact acgaaatcag                                                 20

<210> SEQ ID NO 4
<211> LENGTH: 18
<212> TYPE: DNA
<213> ORGANISM: Artificial Sequence
<220> FEATURE:
<223> OTHER INFORMATION: primer B4503

<400> SEQUENCE: 4
tccggagacg ttgatggt                                                   18

<210> SEQ ID NO 5
<211> LENGTH: 21
<212> TYPE: DNA
<213> ORGANISM: Artificial Sequence
<220> FEATURE:
<223> OTHER INFORMATION: primer B4504

<400> SEQUENCE: 5
cctttcatcg atttccactt c                                               21

<210> SEQ ID NO 6
<211> LENGTH: 20
<212> TYPE: DNA
<213> ORGANISM: Artificial Sequence
<220> FEATURE:
<223> OTHER INFORMATION: primer B4505

<400> SEQUENCE: 6
ttcgtggacg cccagtccca                                                 20

<210> SEQ ID NO 7
<211> LENGTH: 30
<212> TYPE: DNA
<213> ORGANISM: Artificial Sequence
<220> FEATURE:
<223> OTHER INFORMATION: primer B4400

<400> SEQUENCE: 7
gataactagt cctggtccac cggggtcaag                                      30

<210> SEQ ID NO 8
<211> LENGTH: 36
<212> TYPE: DNA
<213> ORGANISM: Artificial Sequence
<220> FEATURE:
<223> OTHER INFORMATION: primer B4401

<400> SEQUENCE: 8
```

```
gctcagatct tccttaagtc agtcgcgcag gttcag                                36

<210> SEQ ID NO 9
<211> LENGTH: 37
<212> TYPE: DNA
<213> ORGANISM: Artificial Sequence
<220> FEATURE:
<223> OTHER INFORMATION: primer B4402

<400> SEQUENCE: 9
aggaagatct gagctagctc ggaccagaac gaaaaag                               37

<210> SEQ ID NO 10
<211> LENGTH: 29
<212> TYPE: DNA
<213> ORGANISM: Artificial Sequence
<220> FEATURE:
<223> OTHER INFORMATION: primer B4403

<400> SEQUENCE: 10
gatactcgag gcggatgaac attgaggtg                                        29

<210> SEQ ID NO 11
<211> LENGTH: 31
<212> TYPE: DNA
<213> ORGANISM: Artificial Sequence
<220> FEATURE:
<223> OTHER INFORMATION: primer B4408

<400> SEQUENCE: 11
gataagatct gagcgcaacg caattaatgt g                                     31

<210> SEQ ID NO 12
<211> LENGTH: 64
<212> TYPE: DNA
<213> ORGANISM: Artificial Sequence
<220> FEATURE:
<223> OTHER INFORMATION: primer B4409

<400> SEQUENCE: 12
gatagctagc agtcaaaagc ctccggtcgg aggcttttga ctttattttt gacaccagac      60
caac                                                                   64

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
gatagctagc atggttttca cgaccatg                                         28

<210> SEQ ID NO 14
<211> LENGTH: 50
<212> TYPE: DNA
<213> ORGANISM: Artificial Sequence
<220> FEATURE:
<223> OTHER INFORMATION: primer B4449

<400> SEQUENCE: 14
gatagctagc gaggtaccga cctaggtttt ccagcgagtg acgtaaaatg                 50

<210> SEQ ID NO 15
```

```
<211> LENGTH: 29
<212> TYPE: DNA
<213> ORGANISM: Artificial Sequence
<220> FEATURE:
<223> OTHER INFORMATION: primer B4450

<400> SEQUENCE: 15
gatacctagg ttagcgccat tcgccattc                                          29

<210> SEQ ID NO 16
<211> LENGTH: 42
<212> TYPE: DNA
<213> ORGANISM: Artificial Sequence
<220> FEATURE:
<223> OTHER INFORMATION: primer

<400> SEQUENCE: 16
ctattccagc gggtaacgta aaatgaccat gattacggat tc                           42

<210> SEQ ID NO 17
<211> LENGTH: 42
<212> TYPE: DNA
<213> ORGANISM: Artificial Sequence
<220> FEATURE:
<223> OTHER INFORMATION: primer B4451

<400> SEQUENCE: 17
gaatccgtaa tcatggtcat tttacgttac ccgctggaat ag                           42

<210> SEQ ID NO 18
<211> LENGTH: 43
<212> TYPE: DNA
<213> ORGANISM: Artificial Sequence
<220> FEATURE:
<223> OTHER INFORMATION: primer B4454

<400> SEQUENCE: 18
caagcgggcc ggctggtctc tcggcaataa ctcctatgtg atc                          43

<210> SEQ ID NO 19
<211> LENGTH: 43
<212> TYPE: DNA
<213> ORGANISM: Artificial Sequence
<220> FEATURE:
<223> OTHER INFORMATION: B4453

<400> SEQUENCE: 19
gatcacatag gagttattgc cgagagacca gccggcccgc ttg                          43

<210> SEQ ID NO 20
<211> LENGTH: 28
<212> TYPE: DNA
<213> ORGANISM: Artificial Sequence
<220> FEATURE:
<223> OTHER INFORMATION: primer B4429

<400> SEQUENCE: 20
gataggtacc gcgaccggtc tgtacttc                                           28

<210> SEQ ID NO 21
<211> LENGTH: 42
<212> TYPE: DNA
<213> ORGANISM: Artificial Sequence
<220> FEATURE:
<223> OTHER INFORMATION: primer B4455

<400> SEQUENCE: 21
```

-continued ctattccagc gggtaacgta aaatgaaatg dacgcggatc ag                          42

<210> SEQ ID NO 22
<211> LENGTH: 42
<212> TYPE: DNA
<213> ORGANISM: Artificial Sequence
<220> FEATURE:
<223> OTHER INFORMATION: primer B4456

<400> SEQUENCE: 22
ctgatccgcg tccatttcat tttacgttac ccgctggaat ag                          42

<210> SEQ ID NO 23
<211> LENGTH: 31
<212> TYPE: DNA
<213> ORGANISM: Artificial Sequence
<220> FEATURE:
<223> OTHER INFORMATION: primer B4457

<400> SEQUENCE: 23
gatagctagc ggcaataact cctatgtgat c                                      31

<210> SEQ ID NO 24
<211> LENGTH: 28
<212> TYPE: DNA
<213> ORGANISM: Artificial Sequence
<220> FEATURE:
<223> OTHER INFORMATION: primer B4410

<400> SEQUENCE: 24
cgcgacatgt cctacagcag cgatggag                                          28

<210> SEQ ID NO 25
<211> LENGTH: 22
<212> TYPE: DNA
<213> ORGANISM: Artificial Sequence
<220> FEATURE:
<223> OTHER INFORMATION: primer B3332

<400> SEQUENCE: 25
ttactccccc ttcaggtaga tg                                                22

<210> SEQ ID NO 26
<211> LENGTH: 40
<212> TYPE: DNA
<213> ORGANISM: Artificial Sequence
<220> FEATURE:
<223> OTHER INFORMATION: primer B3324

<400> SEQUENCE: 26
actcttcgaa ttaacgggat cctcattcag gagtaatgac                             40

<210> SEQ ID NO 27
<211> LENGTH: 44
<212> TYPE: DNA
<213> ORGANISM: Artificial Sequence
<220> FEATURE:
<223> OTHER INFORMATION: primer B4411

<400> SEQUENCE: 27
gtgaatccgt aatcatggtc attttacgtc actcgctgga aaag                        44

<210> SEQ ID NO 28
<211> LENGTH: 44
<212> TYPE: DNA

```
<213> ORGANISM: Artificial Sequence
<220> FEATURE:
<223> OTHER INFORMATION: primer B4412

<400> SEQUENCE: 28
cttttccagc gagtgacgta aaatgaccat gattacggat tcac         44

<210> SEQ ID NO 29
<211> LENGTH: 38
<212> TYPE: DNA
<213> ORGANISM: Artificial Sequence
<220> FEATURE:
<223> OTHER INFORMATION: primer B4413

<400> SEQUENCE: 29
gatattcgaa gagtcgtggt tagcgccatt cgccattc               38

<210> SEQ ID NO 30
<211> LENGTH: 43
<212> TYPE: DNA
<213> ORGANISM: Artificial Sequence
<220> FEATURE:
<223> OTHER INFORMATION: primer b4417

<400> SEQUENCE: 30
gatcacatag gagttattgc cgagagacca gccggcccgc ttg          43

<210> SEQ ID NO 31
<211> LENGTH: 43
<212> TYPE: DNA
<213> ORGANISM: Artificial Sequence
<220> FEATURE:
<223> OTHER INFORMATION: primer B4416

<400> SEQUENCE: 31
caagcgggcc ggctggtctc tcggcaataa ctcctatgtg atc          43

<210> SEQ ID NO 32
<211> LENGTH: 44
<212> TYPE: DNA
<213> ORGANISM: Artificial Sequence
<220> FEATURE:
<223> OTHER INFORMATION: primer B4414

<400> SEQUENCE: 32
gtgaatccgt aatcatggtc attttacgtc actcgctgga aaag         44

<210> SEQ ID NO 33
<211> LENGTH: 44
<212> TYPE: DNA
<213> ORGANISM: Artificial Sequence
<220> FEATURE:
<223> OTHER INFORMATION: primer B4415

<400> SEQUENCE: 33
cttttccagc gagtgacgta aaatgaccat gattacggat tcac         44

<210> SEQ ID NO 34
<211> LENGTH: 40
<212> TYPE: DNA
<213> ORGANISM: Artificial Sequence
<220> FEATURE:
<223> OTHER INFORMATION: primer B3333

<400> SEQUENCE: 34
gcgcttcgaa gagtcgtggt tacgtcactc gctggaaaag              40
```

```
<210> SEQ ID NO 35
<211> LENGTH: 40
<212> TYPE: DNA
<213> ORGANISM: Artificial Sequence
<220> FEATURE:
<223> OTHER INFORMATION: primer B4418

<400> SEQUENCE: 35
gatattcgaa gagtcgtggt tacgtcactc gctggaaaag                              40

<210> SEQ ID NO 36
<211> LENGTH: 28
<212> TYPE: DNA
<213> ORGANISM: Artificial Sequence
<220> FEATURE:
<223> OTHER INFORMATION: primer B4419

<400> SEQUENCE: 36
gatagctagc ctgggattcg aaggttcc                                          28

<210> SEQ ID NO 37
<211> LENGTH: 61
<212> TYPE: DNA
<213> ORGANISM: Artificial Sequence
<220> FEATURE:
<223> OTHER INFORMATION: primer B4420

<400> SEQUENCE: 37
cgagaaaacc cggatcgcct gtaggtacct ccttaagtag gataaggcgt ccgggtttat        60
c                                                                        61

<210> SEQ ID NO 38
<211> LENGTH: 61
<212> TYPE: DNA
<213> ORGANISM: Artificial Sequence
<220> FEATURE:
<223> OTHER INFORMATION: primer B4421

<400> SEQUENCE: 38
gataaacccg gacgccttat cctacttaag gaggtaccta caggcgatcc gggttttctc        60
g                                                                        61

<210> SEQ ID NO 39
<211> LENGTH: 29
<212> TYPE: DNA
<213> ORGANISM: Artificial Sequence
<220> FEATURE:
<223> OTHER INFORMATION: primer B4422

<400> SEQUENCE: 39
gatagctagc tattcgccca aaagaaaag                                         29

<210> SEQ ID NO 40
<211> LENGTH: 31
<212> TYPE: DNA
<213> ORGANISM: Artificial Sequence
<220> FEATURE:
<223> OTHER INFORMATION: primer

<400> SEQUENCE: 40
gatacttaag tactgagaaa aatctggatt c                                      31

<210> SEQ ID NO 41
```

-continued

```
<211> LENGTH: 29
<212> TYPE: DNA
<213> ORGANISM: Artificial Sequence
<220> FEATURE:
<223> OTHER INFORMATION: primer B4424

<400> SEQUENCE: 41
gataggtacc ttagcgccat tcgccattc                                    29

<210> SEQ ID NO 42
<211> LENGTH: 31
<212> TYPE: DNA
<213> ORGANISM: Artificial Sequence
<220> FEATURE:
<223> OTHER INFORMATION: primer B4425

<400> SEQUENCE: 42
gataggtacc ttacgtcact cgctggaaaa g                                 31

<210> SEQ ID NO 43
<211> LENGTH: 72
<212> TYPE: DNA
<213> ORGANISM: Artificial Sequence
<220> FEATURE:
<223> OTHER INFORMATION: primer B4404

<400> SEQUENCE: 43
gatacttaag aaaacaaact aaagcgccct tgtggcgctt tagttttata ctactgagaa  60
aaatctggat tc                                                     72

<210> SEQ ID NO 44
<211> LENGTH: 43
<212> TYPE: DNA
<213> ORGANISM: Artificial Sequence
<220> FEATURE:
<223> OTHER INFORMATION: primer B4405

<400> SEQUENCE: 44
gattttcatc aatactcctg gatcccgtta attcgaagag tcg                    43

<210> SEQ ID NO 45
<211> LENGTH: 43
<212> TYPE: DNA
<213> ORGANISM: Artificial Sequence
<220> FEATURE:
<223> OTHER INFORMATION: primer B4406

<400> SEQUENCE: 45
cgactcttcg aattaacggg atccaggagt attgatgaaa atc                    43

<210> SEQ ID NO 46
<211> LENGTH: 29
<212> TYPE: DNA
<213> ORGANISM: Artificial Sequence
<220> FEATURE:
<223> OTHER INFORMATION: primer B4407

<400> SEQUENCE: 46
gataagatct tcaggagcct tgattgatc                                    29

<210> SEQ ID NO 47
<211> LENGTH: 28
<212> TYPE: DNA
<213> ORGANISM: Artificial Sequence
<220> FEATURE:
<223> OTHER INFORMATION: primer B4465
```

```
<400> SEQUENCE: 47
gatagctagc ttggccagaa agaaggcg                                         28

<210> SEQ ID NO 48
<211> LENGTH: 37
<212> TYPE: DNA
<213> ORGANISM: Artificial Sequence
<220> FEATURE:
<223> OTHER INFORMATION: primer B4466

<400> SEQUENCE: 48
gatacatatg tcggtaccta ttcgcccaaa agaaaag                               37

<210> SEQ ID NO 49
<211> LENGTH: 29
<212> TYPE: DNA
<213> ORGANISM: Artificial Sequence
<220> FEATURE:
<223> OTHER INFORMATION: primer B4467

<400> SEQUENCE: 49
gatacatatg tcaatactcc tgatttttg                                        29

<210> SEQ ID NO 50
<211> LENGTH: 29
<212> TYPE: DNA
<213> ORGANISM: Artificial Sequence
<220> FEATURE:
<223> OTHER INFORMATION: primer B4468

<400> SEQUENCE: 50
gatagctagc aatgaaatgg acgcggatc                                        29

<210> SEQ ID NO 51
<211> LENGTH: 65
<212> TYPE: DNA
<213> ORGANISM: Artificial Sequence
<220> FEATURE:
<223> OTHER INFORMATION: primer B4469

<400> SEQUENCE: 51
gataggtacc gatctagtca aaagcctccg accggaggct tttgacttta gtacttgccg      60
cctag                                                                 65

<210> SEQ ID NO 52
<211> LENGTH: 29
<212> TYPE: DNA
<213> ORGANISM: Artificial Sequence
<220> FEATURE:
<223> OTHER INFORMATION: primer B4470

<400> SEQUENCE: 52
gataccatgg caaattatca aaacgcatc                                        29

<210> SEQ ID NO 53
<211> LENGTH: 28
<212> TYPE: DNA
<213> ORGANISM: Artificial Sequence
<220> FEATURE:
<223> OTHER INFORMATION: primer B4471

<400> SEQUENCE: 53
gataccatgg tagttcctcg ataagtcg                                         28
```

<210> SEQ ID NO 54
<211> LENGTH: 39
<212> TYPE: DNA
<213> ORGANISM: Artificial Sequence
<220> FEATURE:
<223> OTHER INFORMATION: primer B4472

<400> SEQUENCE: 54
gatacatatg cctagggatc tgaccgaccg atctactcc                                  39

<210> SEQ ID NO 55
<211> LENGTH: 29
<212> TYPE: DNA
<213> ORGANISM: Artificial Sequence
<220> FEATURE:
<223> OTHER INFORMATION: primer B4473

<400> SEQUENCE: 55
gataggtacc ttagcgccat tcgccattc                                             29

<210> SEQ ID NO 56
<211> LENGTH: 29
<212> TYPE: DNA
<213> ORGANISM: Artificial Sequence
<220> FEATURE:
<223> OTHER INFORMATION: primer B4474

<400> SEQUENCE: 56
gataggtacc gcgcaacgca attaatgtg                                             29

<210> SEQ ID NO 57
<211> LENGTH: 964
<212> TYPE: PRT
<213> ORGANISM: Bacteriophage SPM-1

<400> SEQUENCE: 57

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Ser Asn Ile Pro Met Pro Ala Gly Gly Ser Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ala
                165                 170                 175

Ser Gln Asn Ala Pro Val Tyr Pro Ala Ser Ala Gly Ala Ala Ala Gly
            180                 185                 190

```
Met Leu Glu Ala Lys Ser Trp Val Ser Gly Ala Asn Thr Phe Cys Val
            195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Val Leu Arg Val Lys Phe Asn Ala Met Asn Thr Gly Ala Ser Thr
        275                 280                 285

Ile Asn Val Ser Gly Phe Gly Ser Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Thr Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Ala Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400

Phe His Phe Asn Asn Arg Ala Lys Asp Phe Asp Tyr Arg Phe Ile
                405                 410                 415

Ser Glu Ala Asp Gly Ser Met Ala Phe Tyr Ser Arg Gln Gly Ser Ala
            420                 425                 430

Gly Pro Thr Gln Asp Ile Leu Phe Ser Arg Ser Asn Val Thr Phe Leu
        435                 440                 445

Gln Pro Arg Leu Asp Val Ala Lys Asn Leu Ala Tyr Ile Ala Asn Ser
    450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Ile Met Arg Trp
            500                 505                 510

Asp Trp Ala Ser Thr Asn Val Ile Phe Asn Asn Arg Pro Leu Phe Ala
        515                 520                 525

Gly Gln Tyr Val Pro Trp Asp Ser Gly Asn Phe Asp Pro Ala Thr Lys
    530                 535                 540

Leu Thr Val Gly Thr Thr Asn Asn Ile Ser Gly Pro Thr Gly Ile Arg
545                 550                 555                 560

Asn Thr Thr Ser Asn Thr Gly Asn Met Asn Thr Trp Gly Ser Ser Ser
                565                 570                 575

Thr Thr Ala Ser Tyr Gly Asn Ala Ala Leu Gln Ile Phe Gly Arg Gly
            580                 585                 590

Gly Gly Glu Pro Ala Ala Ile Tyr Phe Asp Asn Ser Gln Thr Gly Trp
        595                 600                 605
```

```
Tyr Leu Gly Met Asp Lys Asp Gly Gln Leu Lys Arg Ala Gly Trp Ser
    610                 615                 620

Leu Gly Asn Asn Ser Tyr Val Val Thr Asp Glu Ser Asn Ile Arg Asn
625                 630                 635                 640

His Val Asn Gly Met Ser Gly Ala Pro Val Trp Gly Gly Gln Trp Phe
                645                 650                 655

Trp Gly Glu Trp Asn Phe Asn Pro Asn Thr Lys Leu Thr Ile Lys Ala
                660                 665                 670

Gly Thr Gln Glu Thr Ser Ser Thr Ala Ile Phe Ser Thr Leu Pro
                675                 680                 685

Phe Ala Pro Ile Ala Ser Leu Ser Asp Tyr Ser Gln Ala Pro Leu Thr
690                 695                 700

Ile Tyr Asn Ser Pro Thr Gly Pro Ser Ala Lys Pro Ala Val Ile Ala
705                 710                 715                 720

Phe Ile Arg Pro Gly Asn Trp Gly Ala Phe Phe Gly Ile Asp Thr Asp
                725                 730                 735

Asn Lys Leu Lys Trp Gly Gly Gly Ser Leu Gly Asn Asn Ser Arg Glu
                740                 745                 750

Ile Ala Asp Ser Ser Asn Ile Met Asn Leu Trp Ala Ser Asn Pro Thr
                755                 760                 765

Ala Pro Ser Trp Asn Gly Gln Thr Val Trp Arg Ser Gly Asn Phe Asp
770                 775                 780

Pro Ala Thr Lys Val Asp Leu Asn Ala Ala Asn Ala Thr Asn Gly Ser
785                 790                 795                 800

Met Ile Phe Asn Arg Ile Ser Gly Thr Gly Ser Gly Ile Ala Ser Ser
                805                 810                 815

Gly Arg Val Gly Ala Ile Asn Leu Gln Asn Gly Ala His Ser Gly Gln
                820                 825                 830

Ala Ala Ala Val Thr Phe Glu Arg Gly Gly Ser Ile Phe Val Asn Phe
                835                 840                 845

Gly Leu Asp Thr Asp Asn Val Leu Lys Val Gly Gly Asn Leu Gly
                850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Gly Gly Val Gly Ser Tyr Gly
                885                 890                 895

Ile Phe Ala Val Leu Asp Asn Ala Ala Pro Ile Ala Thr Val Gln Pro
                900                 905                 910

Gly Val Val Val Asp Gly Ser Ile Leu Ile Tyr Ser Ser Cys Ala Ala
                915                 920                 925

Asn Tyr Asn Ser Gly Gln Lys Pro Ala Gly Thr Trp Arg Cys Met Gly
                930                 935                 940

Tyr Val Val Asn Arg Asp Ala Asn Thr Ala Asp Ser Ala Thr Leu Phe
945                 950                 955                 960

Gln Arg Val Thr

<210> SEQ ID NO 58
<211> LENGTH: 964
<212> TYPE: PRT
<213> ORGANISM: Bacteriophage F8

<400> SEQUENCE: 58

Met Ile Thr Pro Glu Leu Ile Pro Ser Pro Phe Ala Ala Gln Gly Asp
1               5                   10                  15
```

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
                35                  40                  45

Gln Ala Lys Ala Val Glu Arg Lys Ile Gln Asn Gln Leu Phe Phe Ile
            50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
            115                 120                 125

Trp Ser Val Met Arg Ser Asn Ile Pro Met Pro Ala Gly Gly Ser Gly
        130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ala Ala
                165                 170                 175

Ser Gln Asn Ala Pro Val Tyr Pro Ala Ser Gly Ala Ala Ala Gly
            180                 185                 190

Met Leu Glu Ala Lys Ser Trp Val Ser Gly Ala Asn Thr Phe Cys Val
            195                 200                 205

Gln Arg Tyr Thr Asp Arg Val Gly Asn Val Ala Val Arg Gly Leu Asn
            210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Val Leu Arg Val Lys Phe Asn Ala Met Asn Thr Gly Ala Ser Thr
            275                 280                 285

Ile Asn Val Ser Gly Phe Gly Ser Lys Ala Ile Val Gly Ala Ala Asn
            290                 295                 300

Phe Pro Leu Thr Gly Gly Glu Leu Gly Gln Gly Leu Ile Ala Glu Leu
305                 310                 315                 320

Val Phe Asp Ala Thr Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
            355                 360                 365

Trp Ala Asp Val Val Asn Lys Pro Asn Val Ala Ile Gln Asp Thr Thr
        370                 375                 380

Pro Trp Phe Ala Asn Leu Glu Leu Ser Asp Ala Arg Pro Phe Ile Asp
385                 390                 395                 400

Phe His Phe Asn Asn Asn Arg Ala Lys Asp Phe Asp Tyr Arg Phe Ile
                405                 410                 415

Ser Glu Ala Asp Gly Ser Met Ala Phe Tyr Ser Arg Gln Gly Ser Ala
            420                 425                 430

Gly Pro Thr Gln Asp Ile Leu Phe Ser Arg Ser Asn Val Thr Phe Leu

```
            435                 440                 445
Gln Pro Arg Leu Asp Val Ala Lys Asn Leu Ala Tyr Ile Ala Asn Ser
450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                    485                 490                 495

Asn Thr Thr Asn Pro Asp Gly Ser Tyr Arg Ser Gln Ile Met Arg Trp
                500                 505                 510

Asp Trp Ala Ser Thr Asn Val Ile Phe Asn Asn Arg Pro Leu Phe Ala
            515                 520                 525

Gly Gln Tyr Val Pro Trp Asp Ser Gly Asn Phe Asp Pro Ala Thr Lys
        530                 535                 540

Leu Thr Val Gly Thr Thr Asn Asn Ile Ser Gly Pro Thr Gly Ile Arg
545                 550                 555                 560

Asn Thr Thr Ser Asn Thr Gly Asn Met Asn Thr Trp Gly Ser Ser Ser
                565                 570                 575

Thr Thr Ala Ser Tyr Gly Asn Ala Ala Leu Gln Ile Phe Gly Arg Gly
            580                 585                 590

Gly Gly Glu Pro Ala Ala Ile Tyr Phe Asp Asn Ser Gln Thr Gly Trp
        595                 600                 605

Tyr Leu Gly Met Asp Lys Asp Gly Gln Leu Lys Arg Ala Gly Trp Ser
610                 615                 620

Leu Gly Asn Asn Ser Tyr Val Val Thr Asp Glu Ser Asn Ile Arg Asn
625                 630                 635                 640

His Val Asn Gly Met Ser Gly Ala Pro Val Trp Gly Gln Trp Phe
                645                 650                 655

Trp Gly Glu Trp Asn Phe Asn Pro Asn Thr Lys Leu Thr Ile Lys Ala
            660                 665                 670

Gly Thr Gln Glu Thr Ser Ser Thr Ala Ile Phe Ser Gly Thr Leu Pro
        675                 680                 685

Phe Ala Pro Ile Ala Ser Leu Ser Asp Tyr Ser Gln Ala Pro Leu Thr
690                 695                 700

Ile Tyr Asn Ser Pro Thr Gly Pro Ser Ala Lys Pro Ala Val Ile Ala
705                 710                 715                 720

Phe Ile Arg Pro Gly Asn Trp Gly Ala Phe Gly Ile Asp Thr Asp
                725                 730                 735

Asn Lys Leu Lys Trp Gly Gly Gly Ser Leu Gly Asn Asn Ser Arg Glu
                740                 745                 750

Ile Ala Asp Ser Ser Asn Ile Met Asn Leu Trp Ala Ser Asn Pro Thr
            755                 760                 765

Ala Pro Ser Trp Asn Gly Thr Val Trp Arg Ser Gly Asn Phe Asp
        770                 775                 780

Pro Ala Thr Lys Val Asp Leu Asn Ala Ala Asn Ala Thr Asn Gly Ser
785                 790                 795                 800

Met Ile Phe Asn Arg Ile Ser Gly Thr Gly Ser Gly Ile Ala Ser Ser
                805                 810                 815

Gly Arg Val Gly Ala Ile Asn Leu Gln Asn Gly Ala His Ser Gly Gln
            820                 825                 830

Ala Ala Ala Val Thr Phe Glu Arg Gly Gly Ser Ile Phe Val Asn Phe
        835                 840                 845

Gly Leu Asp Thr Asp Asn Val Leu Lys Val Gly Gly Asn Leu Gly
850                 855                 860
```

```
Ala Asn Ala Tyr Pro Val Ile His Ala Gly Asn Tyr Asn Asn Tyr Ile
865                 870                 875                 880

Asn Gln Ala Leu Val Gln Val Gly Leu Gly Val Gly Ser Tyr Gly
            885                 890                 895

Ile Phe Ala Val Leu Asp Asn Ala Ala Pro Ile Ala Thr Val Gln Pro
                900                 905                 910

Gly Val Val Asp Gly Ser Ile Leu Ile Tyr Ser Ser Cys Ala Ala
            915                 920                 925

Asn Tyr Asn Ser Gly Gln Lys Pro Ala Gly Thr Trp Arg Cys Met Gly
            930                 935                 940

Tyr Val Val Asn Arg Asp Ala Asn Thr Ala Asp Ser Ala Thr Leu Phe
945                 950                 955                 960

Gln Arg Val Thr

<210> SEQ ID NO 59
<211> LENGTH: 964
<212> TYPE: PRT
<213> ORGANISM: Bacteriophage PB1

<400> SEQUENCE: 59

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Ser Asn Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ala
                165                 170                 175

Ser Gln Asn Ala Pro Val Tyr Pro Ala Ser Gly Ala Ala Ala Gly
            180                 185                 190

Met Leu Glu Ala Lys Ser Trp Ile Ser Gly Ser Asn Thr Phe Cys Val
            195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
                260                 265                 270
```

```
Met Ile Leu Arg Val Lys Phe Asn Thr Val Asn Thr Gly Ala Ser Thr
    275                 280                 285

Ile Asn Val Ser Gly Phe Gly Ala Lys Ala Ile Val Gly Ala Ala Asn
290                 295                 300

Phe Pro Leu Thr Gly Gly Glu Leu Gly Gln Gly Leu Ile Ala Glu Leu
305                 310                 315                 320

Val Phe Asp Ala Thr Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
                340                 345                 350

Lys Gln Val Lys Asp Tyr Val Ala Ser Gln Lys Leu Thr Glu Val Asp
                355                 360                 365

Trp Ala Asp Val Val Asn Lys Pro Asn Val Ala Ile Gln Asp Thr Thr
            370                 375                 380

Pro Trp Phe Ala Asn Leu Glu Leu Ser Asp Ala Arg Pro Phe Ile Asp
385                 390                 395                 400

Phe His Phe Asn Asn Asn Arg Ala Lys Asp Phe Asp Tyr Arg Phe Ile
                    405                 410                 415

Ser Glu Ala Asp Gly Ser Met Ala Phe Tyr Ser Arg Gln Gly Ser Ala
                420                 425                 430

Gly Pro Thr Gln Asp Ile Leu Phe Ser Arg Ser Asn Val Thr Phe Leu
                435                 440                 445

Gln Pro Arg Leu Asp Val Ala Lys Asn Leu Ala Tyr Ile Ala Asn Ser
            450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                    485                 490                 495

Asn Thr Thr Asn Pro Asp Gly Ser Tyr Arg Ser Gln Val Met Arg Trp
                500                 505                 510

Asp Trp Ala Ser Thr Asn Val Ile Phe Asn Asn Arg Pro Leu Phe Ala
            515                 520                 525

Gly Gln Tyr Val Pro Trp Asp Ser Gly Asn Phe Asp Pro Ala Thr Lys
530                 535                 540

Leu Thr Val Gly Thr Thr Asn Asn Ile Ser Gly Pro Thr Gly Ile Arg
545                 550                 555                 560

Asn Thr Thr Ser Asn Thr Gly Asn Met Asn Thr Trp Gly Ser Ser Ser
                565                 570                 575

Thr Thr Ala Ser Tyr Gly Asn Ala Ala Leu Gln Ile Phe Gly Arg Gly
                580                 585                 590

Gly Gly Glu Pro Ala Ala Ile Tyr Phe Asp Asn Ser Gln Thr Gly Trp
                595                 600                 605

Tyr Leu Gly Met Asp Lys Asp Gly Gln Leu Lys Arg Ala Gly Trp Ser
            610                 615                 620

Leu Gly Asn Asn Ser Tyr Val Val Thr Asp Glu Ser Asn Ile Arg Asn
625                 630                 635                 640

His Val Asn Gly Met Ser Gly Ala Pro Val Trp Gly Gly Gln Trp Phe
                    645                 650                 655

Trp Gly Glu Trp Asn Phe Asn Pro Asn Thr Lys Leu Thr Ile Lys Ala
                660                 665                 670

Gly Thr Gln Glu Thr Ser Ser Thr Ala Ile Phe Ser Gly Thr Leu Pro
                675                 680                 685
```

```
Phe Ala Pro Ile Ala Ser Leu Ser Asp Tyr Ser Gln Ala Pro Leu Thr
            690                 695                 700

Ile Tyr Asn Ser Pro Thr Gly Pro Ser Ala Lys Pro Val Ile Ala
705                 710                 715                 720

Phe Ile Arg Pro Gly Asn Trp Gly Ala Phe Gly Ile Asp Thr Asp
            725                 730                 735

Asn Lys Leu Lys Trp Gly Gly Ser Leu Gly Asn Asn Ser Arg Glu
            740                 745                 750

Ile Ala Asp Ser Ser Asn Ile Met Asn Leu Trp Ala Ser Asn Pro Thr
            755                 760                 765

Ala Pro Ser Trp Asn Gly Gln Thr Val Trp Arg Ser Gly Asn Phe Asp
770                 775                 780

Pro Ala Thr Lys Val Asp Leu Asn Ala Ala Asn Ala Thr Asn Gly Asn
785                 790                 795                 800

Met Ile Phe Asn Arg Ile Ser Gly Thr Gly Ser Gly Ile Ala Ser Ser
            805                 810                 815

Gly Arg Val Gly Ala Ile Asn Leu Gln Asn Gly Ala His Ser Gly Gln
            820                 825                 830

Ala Ala Ala Val Thr Phe Glu Arg Gly Gly Ser Ile Phe Val Asn Phe
            835                 840                 845

Gly Leu Asp Thr Asp Asn Val Leu Lys Val Gly Gly Asn Leu Gly
850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Gly Gly Val Gly Ser Tyr Gly
            885                 890                 895

Ile Phe Ala Val Leu Asp Asn Ala Ala Pro Ile Ala Thr Val Gln Pro
            900                 905                 910

Gly Val Val Val Asp Gly Ser Ile Leu Ile Tyr Ser Ser Cys Ala Ala
            915                 920                 925

Asn Tyr Asn Ser Gly Gln Lys Pro Ala Gly Thr Trp Arg Cys Met Gly
            930                 935                 940

Tyr Val Val Asn Arg Asp Ala Asn Thr Pro Asp Ser Ala Thr Leu Phe
945                 950                 955                 960

Gln Arg Val Thr

<210> SEQ ID NO 60
<211> LENGTH: 964
<212> TYPE: PRT
<213> ORGANISM: Bacteriophage C36

<400> SEQUENCE: 60

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95
```

```
Val Gly Asn Asp Gly Ile Met Arg Arg Tyr Arg Ser Met Val Asn Ala
                100                 105                 110

Asn Ala Ser Asp Pro Leu Ser Ser Thr Thr Trp Glu Glu Gln Pro Ala
            115                 120                 125

Trp Ser Val Met Arg Ser Ser Ile Pro Met Pro Ala Gly Gly Pro Gly
        130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Val Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Ile Ser Gly Ser Asn Thr Phe Cys Val
        195                 200                 205

Gln Arg Tyr Thr Asp Arg Val Gly Asn Val Ala Val Arg Gly Leu Asn
210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Pro Ala Asn Ala
            245                 250                 255

Tyr Thr Leu Thr Leu Val Pro Gln Leu Gln Gly Gly Leu Val Asp Gly
        260                 265                 270

Met Ile Leu Arg Val Lys Phe Asn Thr Val Asn Thr Gly Ala Ser Thr
            275                 280                 285

Ile Asn Val Ser Gly Phe Gly Ala Lys Ala Ile Val Gly Ala Ala Asn
        290                 295                 300

Phe Pro Leu Thr Gly Gly Glu Leu Gly Gln Gly Leu Ile Ala Glu Leu
305                 310                 315                 320

Val Phe Asp Ala Thr Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Ala Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400

Phe His Phe Asn Asn Arg Ala Lys Asp Phe Asp Tyr Arg Phe Ile
                405                 410                 415

Ser Glu Ala Asp Gly Ser Met Ala Phe Tyr Ser Arg Gln Gly Ser Ala
                420                 425                 430

Gly Pro Thr Gln Asp Ile Leu Phe Ser Arg Ser Asn Val Thr Phe Leu
        435                 440                 445

Gln Pro Arg Leu Asp Val Ala Lys Asn Leu Ala Tyr Ile Ala Asn Ser
        450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Ile Met Arg Trp
            500                 505                 510

Asp Trp Ala Ser Thr Asn Val Ile Phe Asn Asn Arg Pro Leu Phe Ala
```

```
            515                 520                 525
Gly Gln Tyr Val Pro Trp Asp Ser Gly Asn Phe Asp Pro Ala Thr Lys
530                 535                 540

Leu Thr Val Gly Thr Thr Asn Ile Ser Gly Pro Thr Gly Ile Arg
545                 550                 555                 560

Asn Thr Thr Ser Asn Thr Gly Asn Met Asn Thr Trp Gly Ser Ser Ser
                565                 570                 575

Thr Thr Ala Ser Tyr Gly Asn Ala Ala Val Gln Ile Phe Gly Arg Gly
            580                 585                 590

Asp Gly Glu Pro Ala Ala Ile Tyr Phe Asp Asn Ser Gln Thr Gly Trp
        595                 600                 605

Tyr Leu Gly Met Asp Lys Asp Gly Gln Leu Lys Arg Ala Gly Trp Ser
    610                 615                 620

Leu Gly Asn Asn Ser Tyr Val Val Thr Asp Glu Ser Asn Ile Arg Phe
625                 630                 635                 640

His Val Asn Ser Met Ala Gly Thr Pro Val Trp Gly Gly Asn Glu Phe
                645                 650                 655

Trp Gly Pro Trp Asn Phe Asn Pro Asn Thr Lys Leu Thr Ile Lys Ala
            660                 665                 670

Gly Thr Gln Glu Thr Ser Ser Thr Ala Ile Phe Ser Gly Thr Met Pro
        675                 680                 685

Phe Ala Pro Ile Ala Ser Leu Ser Asp Tyr Ser Gln Ala Pro Leu Thr
    690                 695                 700

Ile Tyr Asn Ser Pro Thr Gly Pro Ser Ala Lys Pro Ala Val Ile Ala
705                 710                 715                 720

Phe Ile Arg Pro Gly Asn Trp Gly Ala Phe Phe Gly Ile Asp Thr Asp
                725                 730                 735

Asn Lys Leu Lys Trp Gly Gly Ser Leu Gly Asn Ser Ser Arg Glu
            740                 745                 750

Ile Ala Asp Ser Ser Asn Ile Met Asn Leu Trp Ala Ala Asn Pro Thr
        755                 760                 765

Ala Pro Ser Trp Asn Gly Gln Thr Val Trp Arg Ser Gly Asn Phe Asp
    770                 775                 780

Pro Ala Thr Lys Val Asp Leu Asn Ala Ala Asn Ala Thr Asn Gly Asn
785                 790                 795                 800

Met Val Phe Asn Arg Ile Ser Gly Thr Gly Ser Gly Ile Ala Ser Ser
                805                 810                 815

Gly Arg Val Gly Ala Ile Asn Leu Gln Asn Gly Ala His Ser Gly Gln
            820                 825                 830

Ala Ala Ala Val Thr Phe Glu Arg Gly Gly Ser Ile Phe Val Asn Phe
        835                 840                 845

Gly Leu Asp Thr Asp Asn Val Leu Lys Val Gly Gly Asn Leu Gly
    850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Gly Val Gly Ser Tyr Gly
                885                 890                 895

Ile Phe Ala Val Leu Asp Asn Ala Ala Pro Ile Ala Thr Val Gln Pro
            900                 905                 910

Gly Val Val Val Asp Gly Ser Ile Leu Ile Tyr Ser Ser Cys Ser Ala
        915                 920                 925

Asn Tyr Asn Ser Gly Gln Arg Pro Ala Gly Thr Trp Arg Cys Met Gly
    930                 935                 940
```

Tyr Val Val Asn Arg Asp Ala Asn Thr Pro Asp Ser Ala Thr Leu Phe
945                 950                 955                 960

Gln Arg Val Thr

<210> SEQ ID NO 61
<211> LENGTH: 964
<212> TYPE: PRT
<213> ORGANISM: Bacteriophage LBL3

<400> SEQUENCE: 61

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Ser Asn Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Met Asn Thr Gly Ala Ser Thr
        275                 280                 285

Ile Asn Val Ser Gly Phe Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Thr Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

-continued

Lys Gln Val Lys Asp Tyr Val Ala Ser Gln Lys Leu Thr Glu Val Asp
        355                 360                 365

Trp Ala Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400

Phe His Phe Asn Asn Asn Arg Ala Lys Asp Phe Asp Tyr Arg Phe Ile
                    405                 410                 415

Ser Glu Ala Asp Gly Ser Met Ala Phe Tyr Ser Arg Gln Gly Ser Ala
                420                 425                 430

Gly Pro Thr Gln Asp Ile Leu Phe Ser Arg Ser Asn Val Thr Phe Leu
                435                 440                 445

Gln Pro Arg Leu Asp Val Ala Lys Asn Leu Ala Tyr Ile Ala Asn Ser
    450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Ile Met Arg Trp
                500                 505                 510

Asp Trp Ala Ser Thr Asn Val Ile Phe Asn Asn Arg Pro Leu Phe Ala
    515                 520                 525

Gly Gln Tyr Val Pro Trp Asp Ser Gly Asn Phe Asp Pro Ala Thr Lys
    530                 535                 540

Leu Thr Val Gly Thr Thr Asn Asn Ile Ser Arg Pro Thr Gly Ile Arg
545                 550                 555                 560

Asn Thr Thr Ser Asn Thr Gly Asn Met Asn Thr Trp Gly Ser Ser Ser
                565                 570                 575

Thr Thr Ala Ser Tyr Gly Asn Ala Ala Leu Gln Ile Phe Gly Arg Gly
                580                 585                 590

Gly Gly Glu Pro Ala Ala Ile Tyr Phe Asp Asn Ser Gln Thr Gly Trp
            595                 600                 605

Tyr Leu Gly Met Asp Lys Asp Gly Gln Leu Lys Arg Ala Gly Trp Ser
    610                 615                 620

Leu Gly Asn Asn Ser Tyr Val Val Thr Asp Glu Ser Asn Ile Arg Phe
625                 630                 635                 640

His Val Asn Ser Met Ala Gly Thr Pro Val Trp Gly Asn Glu Phe
                645                 650                 655

Trp Gly Pro Trp Asn Phe Asn Pro Asn Thr Lys Leu Thr Ile Lys Ala
            660                 665                 670

Gly Thr Gln Glu Thr Ser Ser Thr Ala Ile Phe Ser Gly Thr Met Pro
            675                 680                 685

Phe Ala Pro Ile Ala Ser Leu Ser Asp Tyr Ser Gln Ala Pro Leu Thr
    690                 695                 700

Val Tyr Asn Ser Pro Thr Gly Pro Ser Ala Lys Pro Ala Val Ile Ala
705                 710                 715                 720

Phe Ile Arg Pro Gly Asn Trp Gly Ala Phe Phe Gly Ile Asp Thr Asp
                725                 730                 735

Asn Lys Leu Lys Trp Gly Gly Ser Leu Gly Asn Ser Ser Arg Glu
            740                 745                 750

Ile Ala Asp Ser Ser Asn Ile Met Asn Leu Trp Ala Ala Asn Pro Thr
                755                 760                 765

```
Ala Pro Thr Trp Asn Gly Gln Thr Ile Trp Arg Ser Gly Asn Phe Asp
770                 775                 780

Pro Ala Thr Lys Val Asp Leu Asn Ala Ala Asn Ala Thr Asn Gly Asn
785                 790                 795                 800

Met Ile Phe Asn Arg Ile Ala Gly Thr Gly Ser Gly Ile Ala Ser Ser
                805                 810                 815

Asp Arg Val Gly Ala Ile Ser Leu Gln Asn Gly Ala Thr Ala Gly Ala
            820                 825                 830

Ala Ala Ala Val Thr Phe Glu Arg Gly Gly Phe Phe Val Asn Phe
        835                 840                 845

Gly Leu Asp Thr Asp Asn Val Leu Lys Val Gly Gly Asn Leu Gly
    850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Gly Val Gly Ser Tyr Gly
                885                 890                 895

Ile Phe Ala Val Leu Asp Tyr Ala Ala Pro Thr Ala Thr Val Gln Pro
                900                 905                 910

Gly Val Ile Val Asp Gly Ser Ile Leu Ile Tyr Ser Ser Cys Ser Ala
            915                 920                 925

His Tyr Asn Ser Gly Gln Arg Pro Ala Gly Thr Trp Arg Cys Met Gly
        930                 935                 940

Tyr Val Leu Asn Arg Asp Ala Arg Asp Pro Asp Ser Ala Thr Leu Phe
945                 950                 955                 960

Gln Arg Val Thr

<210> SEQ ID NO 62
<211> LENGTH: 964
<212> TYPE: PRT
<213> ORGANISM: Bacteriophage Phi33

<400> SEQUENCE: 62

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
                20                  25                  30

Asp Gly Tyr Thr Pro Asp Tyr Glu Ile Ser Leu Ala Ser Asn Asn Pro
            35                  40                  45

Gln Ala Lys Ala Val Glu Arg Lys Ile Gln Asn Gln Leu Phe Phe Ile
        50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ile Asp Pro Leu Ser Ser Thr Thr Trp Glu Gln Pro Ala
        115                 120                 125

Trp Ser Val Met Arg Ser Asn Ile Pro Met Pro Ala Gly Gly Pro Gly
130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ala
                165                 170                 175
```

-continued

```
Ser Gln Asn Ala Pro Val Tyr Pro Ala Ser Ala Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Met Asn Thr Gly Ala Ser Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Ala Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
        435                 440                 445

Gln Pro Arg Leu Asp Val Ala Lys Asn Leu Ala Tyr Ile Ala Asn Ser
    450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Ile Met Arg Trp
            500                 505                 510

Asp Trp Ala Ser Thr Asn Val Ile Phe Asn Asn Arg Pro Leu Phe Ala
        515                 520                 525

Gly Gln Tyr Val Pro Trp Asp Ser Gly Asn Phe Asp Pro Ser Thr Lys
    530                 535                 540

Leu Thr Val Asn Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Leu Gln Ile Phe Gly Lys Gly
            580                 585                 590

Gly Gly Glu Pro Ala Ala Leu Tyr Phe Asp Asn Ser Gln Thr Gly Trp
```

```
                595                 600                 605
Tyr Leu Gly Met Asp Lys Asp Gly Gln Leu Lys Arg Ala Gly Trp Ser
610                 615                 620

Leu Gly Asn Asn Ala Tyr Val Ile Thr Asp Glu Ser Asn Ile Arg Phe
625                 630                 635                 640

His Val Asn Ser Met Ala Gly Thr Pro Val Trp Gly Gly Asn Glu Phe
                645                 650                 655

Trp Gly Pro Trp Asn Phe Asn Pro Asn Thr Lys Leu Thr Ile Lys Ala
                660                 665                 670

Gly Thr Gln Glu Thr Ser Ser Thr Ala Ile Phe Ser Gly Thr Met Pro
                675                 680                 685

Phe Ala Pro Ile Ala Ser Leu Ser Asp Tyr Ser Gln Ala Pro Leu Thr
690                 695                 700

Val Tyr Asn Ala Pro Thr Gly Pro Ser Ala Lys Pro Ala Val Ile Ala
705                 710                 715                 720

Phe Ile Arg Pro Gly Asn Trp Gly Ala Phe Phe Gly Ile Asp Thr Asp
                725                 730                 735

Asn Lys Leu Lys Trp Gly Gly Gly Ser Leu Gly Asn Ser Ser Arg Glu
                740                 745                 750

Ile Ala Asp Ser Ser Asn Ile Met Asn Leu Trp Ala Ala Asn Pro Thr
                755                 760                 765

Ala Pro Ser Trp Asn Gly Gln Thr Ile Trp Arg Ser Gly Asn Phe Asp
770                 775                 780

Pro Ala Thr Lys Val Asp Leu Asn Ala Ala Asn Ala Thr Asn Gly Asn
785                 790                 795                 800

Met Ile Phe Asn Arg Ile Ala Gly Thr Gly Ser Gly Ile Ala Ser Ser
                805                 810                 815

Gly Arg Val Gly Ala Ile Asn Leu Gln Asn Gly Glu His Ser Gly Gln
                820                 825                 830

Ala Ala Ala Val Thr Phe Glu Arg Gly Gly Ser Ile Phe Val Asn Phe
                835                 840                 845

Gly Leu Asp Thr Asp Asn Val Leu Lys Val Gly Gly Gly Asn Leu Gly
                850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Glu Gly Val Gly Ser Tyr Gly
                885                 890                 895

Ile Phe Ala Val Leu Asp Asn Ala Ala Pro Thr Ala Thr Val Gln Pro
                900                 905                 910

Gly Val Val Val Asp Gly Ser Ile Leu Ile Tyr Ser Ser Cys Ala Ala
                915                 920                 925

Asn Tyr Asn Ser Gly Lys Arg Pro Ala Gly Thr Trp Arg Cys Met Gly
                930                 935                 940

Tyr Val Val Asn Arg Asp Ala Asn Thr Pro Asp Ser Ala Thr Leu Phe
945                 950                 955                 960

Gln Arg Val Thr
```

<210> SEQ ID NO 63
<211> LENGTH: 964
<212> TYPE: PRT
<213> ORGANISM: Bacteriophage LMA2

<400> SEQUENCE: 63

Met Ile Thr Pro Glu Leu Ile Pro Ser Pro Phe Ala Ala Gln Gly Asp

-continued

```
1               5                   10                  15
Lys Asp Pro Ile Pro Gln Thr Ser Ser Thr Gly Phe Ala Asn Leu Arg
                20                  25                  30

Asp Gly Tyr Thr Pro Asp Tyr Glu Ile Ser Leu Ala Ser Asn Asn Pro
                35                  40                  45

Gln Ala Lys Val Val Glu Arg Lys Ile Gln Asn Gln Leu Phe Phe Ile
            50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
                100                 105                 110

Asn Ala Ser Asp Pro Leu Ser Ser Thr Thr Trp Glu Glu Gln Pro Ala
            115                 120                 125

Trp Ser Ala Met Arg Ser Asn Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ala Asn Thr Phe Cys Val
            195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
                260                 265                 270

Met Ile Leu Arg Val Lys Phe Asn Thr Met Asn Thr Gly Ala Thr Thr
            275                 280                 285

Ile Asn Val Ser Gly Leu Gly Ala Lys Ala Ile Val Gly Ala Ala Asn
            290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
            355                 360                 365

Trp Ala Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
            420                 425                 430
```

-continued

```
Gly Pro Thr Gln Asp Ile Leu Phe Asn Arg Asn Ser Val Thr Phe Phe
        435                 440                 445

Gln Pro Arg Leu Asp Val Ala Lys Asn Leu Ala Tyr Ile Ala Asn Ser
    450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Val Met Arg Trp
                500                 505                 510

Asp Trp Ala Ser Thr Asn Val Ile Phe Asn Asn Arg Pro Leu Phe Ala
            515                 520                 525

Gly Gln Tyr Thr Pro Trp Asp Ser Gly Asn Phe Asp Pro Ser Thr Lys
        530                 535                 540

Leu Thr Val Asn Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Ile Gln Ile Phe Gly Lys Gly
                580                 585                 590

Gly Gly Glu Pro Ala Ala Ile Tyr Phe Asp Asn Ser Gln Thr Gly Trp
            595                 600                 605

Tyr Leu Gly Met Asp Lys Asp Gly Gln Leu Lys Arg Ala Gly Trp Ser
        610                 615                 620

Leu Gly Asn Asn Ser Tyr Val Ile Thr Asp Glu Leu Asn Ile Arg Asn
625                 630                 635                 640

His Ile Asn Gly Met Ala Ala Arg Pro Val Trp Gly Gly Asn Glu Phe
                645                 650                 655

Trp Gly Pro Trp Asn Phe Asn Pro Asn Thr Lys Leu Thr Ile Lys Ala
                660                 665                 670

Gly Thr Gln Glu Thr Ser Ser Thr Ala Ile Tyr Ser Gly Thr Met Pro
            675                 680                 685

Phe Ala Pro Ile Ala Ser Leu Ser Asp Tyr Ser Gln Ala Pro Leu Thr
        690                 695                 700

Ile Tyr Asn Ala Pro Thr Gly Pro Ser Ala Lys Pro Ala Val Ile Ala
705                 710                 715                 720

Phe Ile Arg Pro Gly Asn Trp Gly Ala Phe Phe Gly Leu Asp Thr Asp
                725                 730                 735

Asn Lys Leu Lys Trp Gly Gly Ser Leu Gly Asn Ser Ser Met Glu
                740                 745                 750

Ile Ala Asp Ser Ser Asn Ile Met Asn Leu Trp Ala Ala Asn Pro Thr
            755                 760                 765

Ala Pro Thr Trp Asn Gly Gln Thr Val Trp Arg Ser Gly Asn Phe Asp
        770                 775                 780

Pro Ala Thr Lys Val Asp Leu Asn Ala Pro Asn Ala Thr Asn Gly Asn
785                 790                 795                 800

Met Ile Phe Asn Arg Ile Ala Gly Thr Gly Ser Gly Ile Ala Ser Ser
                805                 810                 815

Gly Arg Val Gly Ala Ile Ser Leu Gln Asn Gly Ala Thr Ala Gly Ala
                820                 825                 830

Ala Ala Ala Val Thr Phe Glu Arg Gly Gly Gly Phe Phe Val Asn Phe
            835                 840                 845
```

```
Gly Leu Asp Thr Asp Asn Val Leu Lys Val Gly Gly Gly Asn Leu Gly
            850                 855                 860

Ala Asn Ala Tyr Pro Val Ile His Ala Gly Asn Tyr Asn Ser Tyr Ile
865                 870                 875                 880

Asn Gln Ala Leu Val Gln Val Gly Leu Gly Gly Val Gly Ser Tyr Ala
            885                 890                 895

Ala Leu Ala Val Tyr Asp Thr Ser Ala Pro Ala Ser Ser Val Gly Pro
            900                 905                 910

Gly Thr Ile Leu Asp Gly Ser Val Leu Phe Tyr Ser Ser Phe Asn Ala
            915                 920                 925

Asn Phe Arg Ser Gly Thr Lys Pro Thr Gly Thr Trp Arg Cys Met Gly
            930                 935                 940

Tyr Ile Leu Asn Arg Asp Gly Thr Asn Pro Asp Ser Ala Thr Leu Phe
945                 950                 955                 960

Gln Arg Val Thr
```

<210> SEQ ID NO 64
<211> LENGTH: 963
<212> TYPE: PRT
<213> ORGANISM: Bacteriophage KPP12

<400> SEQUENCE: 64

```
Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Ala Met Arg Ser Asn Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Gly Ala Ala Ala Gly
            180                 185                 190

Met Leu Glu Ala Lys Ser Trp Val Ser Gly Ala Asn Thr Phe Cys Val
    195                 200                 205

Gln Arg Tyr Thr Asp Arg Val Gly Asn Val Ala Leu Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255
```

```
Tyr Thr Leu Thr Leu Val Pro Gln Leu Gln Gly Gly Leu Val Asp Gly
            260                 265                 270

Met Ile Leu Arg Val Lys Phe Asn Thr Met Asn Thr Gly Ala Ser Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
                340                 345                 350

Lys Gln Val Lys Asp Tyr Val Ala Ser Gln Lys Leu Thr Glu Val Asp
            355                 360                 365

Trp Ala Asp Val Val Asn Lys Pro Asn Val Ala Ile Gln Asp Thr Thr
370                 375                 380

Pro Trp Phe Ala Asn Leu Glu Leu Ser Asp Ala Arg Pro Phe Ile Asp
385                 390                 395                 400

Phe His Phe Asn Asn Arg Ala Lys Asp Phe Asp Tyr Arg Phe Ile
                405                 410                 415

Ser Glu Ala Asp Gly Ser Met Ala Phe Tyr Ser Arg Gln Gly Ser Ala
                420                 425                 430

Gly Pro Thr Gln Asp Ile Leu Phe Ser Arg Ser Asn Val Thr Phe Leu
                435                 440                 445

Gln Pro Arg Leu Asp Val Ala Lys Asn Leu Ala Tyr Ile Ala Asn Ser
            450                 455                 460

Gly Ser Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Ile Met Arg Trp
            500                 505                 510

Asp Trp Ala Ser Thr Asn Val Ile Phe Asn Asn Arg Pro Leu Phe Ala
        515                 520                 525

Gly Gln Tyr Thr Pro Trp Asp Ser Gly Asn Phe Asp Pro Ser Thr Lys
    530                 535                 540

Leu Thr Val Asn Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Ser Ser
                565                 570                 575

Thr Thr Ala Ser Tyr Gly Asn Ala Ala Leu Gln Ile Phe Gly Lys Gly
                580                 585                 590

Gly Gly Glu Pro Ala Ala Leu Tyr Phe Asp Asn Ser Gln Thr Gly Trp
            595                 600                 605

Tyr Leu Gly Met Asp Lys Asp Gly Gln Leu Lys Arg Ala Gly Trp Ser
        610                 615                 620

Leu Gly Asn Asn Ala Tyr Val Ile Thr Asp Glu Ser Asn Ile Arg Phe
625                 630                 635                 640

His Val Asn Ser Met Ala Gly Thr Pro Val Trp Gly Asn Glu Phe
                645                 650                 655

Trp Gly Ser Trp Asn Phe Asn Pro Asn Thr Lys Leu Thr Ile Lys Ala
                660                 665                 670

Gly Thr Gln Glu Thr Ser Ser Thr Ala Ile Phe Ser Glu Thr Met Pro
```

```
                675                 680                 685
Phe Ala Pro Ile Ala Ser Leu Ser Asp Tyr Ser Gln Ala Pro Leu Thr
        690                 695                 700

Ile Tyr Asn Ala Pro Thr Gly Pro Ser Ala Lys Pro Ala Val Ile Ala
705                 710                 715                 720

Phe Ile Arg Pro Gly Asn Trp Gly Ala Phe Gly Leu Asp Thr Asp
                725                 730                 735

Asn Lys Leu Lys Trp Gly Gly Ser Leu Gly Asn Ser Ser Arg Glu
        740                 745                 750

Ile Ala Asp Ser Arg Asn Ile Met Asn Leu Trp Ala Ala Asn Pro Thr
        755                 760                 765

Ala Pro Thr Trp Asn Gly Gln Thr Val Trp Arg Ser Gly Asn Phe Asp
770                 775                 780

Pro Ala Thr Lys Val Asp Leu Asn Ala Pro Asn Ala Thr Asn Gly Asn
785                 790                 795                 800

Met Ile Phe Asn Arg Ile Ala Gly Thr Gly Ser Gly Ile Ala Ser Ser
                805                 810                 815

Gly Arg Val Gly Ala Ile Ser Leu Gln Asn Gly Ala Thr Ala Gly Ala
                820                 825                 830

Ala Ala Ala Val Thr Phe Glu Arg Gly Gly Phe Phe Val Asn Phe Gly
        835                 840                 845

Leu Asp Thr Asp Asn Val Leu Lys Val Gly Gly Gly Asn Leu Gly Ala
850                 855                 860

Asn Ala Tyr Pro Val Ile His Ala Gly Asn Tyr Asn Ser Tyr Ile Asn
865                 870                 875                 880

Gln Ala Leu Val Gln Val Gly Leu Gly Val Gly Ser Tyr Ala Ala
                885                 890                 895

Leu Ala Val Tyr Asp Thr Ser Ala Pro Ala Ser Ser Val Gly Pro Gly
                900                 905                 910

Thr Ile Leu Asp Gly Ser Val Leu Phe Tyr Ser Ser Phe Asp Ala Asn
        915                 920                 925

Phe Arg Ser Gly Thr Lys Pro Thr Gly Thr Trp Arg Cys Met Gly Tyr
        930                 935                 940

Val Leu Asn Arg Asp Gly Thr Asn Pro Asp Ser Ala Ala Leu Phe Gln
945                 950                 955                 960

Arg Val Thr

<210> SEQ ID NO 65
<211> LENGTH: 962
<212> TYPE: PRT
<213> ORGANISM: Bacteriophage JG024

<400> SEQUENCE: 65

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
                20                  25                  30

Asp Gly Tyr Thr Pro Asp Tyr Glu Ile Ser Leu Ala Ser Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
```

```
                        85                  90                  95
Val Gly Asn Asp Gly Ile Met Arg Arg Tyr Arg Ser Met Val Asn Ala
                100                 105                 110

Asn Ala Ser Asp Pro Leu Ser Ser Thr Thr Trp Glu Glu Gln Pro Ala
            115                 120                 125

Trp Ser Val Met Arg Thr Asn Ile Pro Met Pro Ala Gly Gly Pro Gly
        130                 135                 140

Leu Ser Ser Gly Gly Glu Val Ile Thr Thr Gly Arg Asn Phe Asn Glu
145                 150                 155                 160

Leu Leu Asn Gly Thr Trp Glu Phe Phe Ser Asp Ala Ile Val Val Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ser Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln His Gly Arg Val Thr Tyr Gly Thr Ala Ala Gly Pro Ala Asn Ala
                245                 250                 255

Tyr Thr Leu Thr Leu Val Pro Gln Ile Gln Gly Gly Leu Val Asp Gly
            260                 265                 270

Met Ile Leu Arg Val Lys Phe Asn Thr Met Asn Thr Gly Ala Thr Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Glu Ser Gln Lys Leu Thr Glu Val Asp
        355                 360                 365

Trp Thr Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
        435                 440                 445

Gln Pro Arg Leu Asp Val Ala Lys Asn Leu Ala Tyr Ile Ala Asn Ser
    450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Val Met Arg Trp
            500                 505                 510
```

```
Asp Trp Ala Ser Thr Asn Val Ile Phe Asn Asn Arg Pro Leu Phe Ala
            515                 520                 525

Gly Gln Tyr Thr Pro Trp Asp Ser Gly Asn Phe Asp Pro Ser Thr Lys
530                 535                 540

Leu Thr Val Ser Ala Thr Asn Gln Ile Ser Gly Pro Thr Gly Ile Arg
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Ile Gln Ile Phe Gly Lys Gly
            580                 585                 590

Gly Gly Glu Pro Ala Ala Ile Tyr Phe Asp Asn Ser Gln Thr Gly Trp
        595                 600                 605

Tyr Leu Gly Met Asp Lys Asp Gly Gln Leu Lys Arg Ala Gly Trp Ser
    610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Asn Val Glu Phe
                645                 650                 655

Trp Gly Pro Trp Asn Phe Asp Pro Asn Leu Lys Leu Thr Leu Asn Ala
            660                 665                 670

Phe Asn Asp Ser Ser Tyr Thr Arg Met Thr Asn Ser Gly Ala Lys Asp
        675                 680                 685

Val Gly Ile Ala Ser Met Thr Ser Tyr Ala Asp Ala Ala Met Ser Phe
    690                 695                 700

Phe Asn Tyr Glu Ala Ser Asn Pro Thr Gly Pro Arg Ala Ala Val Ile
705                 710                 715                 720

Ser Phe Val Arg Asn Gly Ser Arg Gly Val Leu Phe Gly Leu Asp Ser
                725                 730                 735

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
        755                 760                 765

Ala Ala Pro Asn Trp Asn Gly Gln Thr Ile Trp Arg Ser Gly Asn Phe
    770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
        835                 840                 845

Asp Ala Asp Asn Val Val Lys Ile Gly Gly Gly Thr Met Gly Gly Val
850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Gly Val Gly Ser Tyr Ala Ile Leu
                885                 890                 895

Ala Val Leu Asp Thr Ser Ala Pro Ala Ala Ser Ile Ala Pro Gly Thr
            900                 905                 910

Ile Met Asp Ser Ser Lys Leu Phe Tyr Ser Ser Cys Asp Ser Thr Tyr
        915                 920                 925
```

Arg Ser Ser Ala Ser Pro Thr Gly Thr Trp Arg Cys Met Gly Tyr Val
930                 935                 940

Tyr Asn Arg Asp Ser Thr Asn Gly Asp Ser Ala Ser Leu Phe Gln Arg
945                 950                 955                 960

Val Thr

<210> SEQ ID NO 66
<211> LENGTH: 962
<212> TYPE: PRT
<213> ORGANISM: Bacteriophage PTP92

<400> SEQUENCE: 66

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Gln Pro Ala
        115                 120                 125

Trp Ser Val Met Arg Thr Asn Ile Pro Met Pro Ala Gly Gly Pro Gly
130                 135                 140

Leu Ser Ser Gly Gly Glu Val Ile Thr Gly Arg Asn Phe Asn Glu
145                 150                 155                 160

Leu Leu Asn Gly Thr Trp Glu Phe Phe Ser Asp Ala Ile Val Val Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ser Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln His Gly Arg Val Thr Tyr Gly Thr Ala Ala Gly Pro Ala Asn Ala
                245                 250                 255

Tyr Thr Leu Thr Leu Val Pro Gln Ile Gln Gly Gly Leu Val Asp Gly
            260                 265                 270

Met Ile Leu Arg Val Lys Phe Asn Thr Met Asn Thr Gly Ala Thr Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

```
Arg Ile Gln Val Gly Asn Ala Asp Gln Asp Tyr Gln Ala Pro Ser Trp
            340                 345                 350
Lys Gln Val Lys Asp Tyr Val Glu Ser Gln Lys Leu Thr Glu Val Asp
            355                 360                 365
Trp Thr Asp Val Val Asn Lys Pro Asn Val Ala Ile Gln Asp Thr Thr
            370                 375                 380
Pro Trp Phe Ala Asn Leu Glu Leu Ser Asp Ala Arg Pro Phe Ile Asp
385                 390                 395                 400
Phe His Phe Asn Ser Asn Arg Ala Lys Asp Phe Asp Tyr Arg Leu Ile
            405                 410                 415
Ser Glu Ala Asp Gly Ser Leu Ala Phe Tyr Ser Arg Gln Gly Ser Ala
            420                 425                 430
Gly Pro Thr Gln Asp Ile Leu Phe Asn Arg Asn Ser Val Thr Phe Phe
            435                 440                 445
Gln Pro Arg Leu Asp Val Ala Lys Asn Leu Ala Tyr Ile Ala Asn Ser
            450                 455                 460
Gly Pro Leu Trp Gln Asn Thr Thr Ala Asp Gln Pro Gly Trp Lys Phe
465                 470                 475                 480
Thr Phe Ala Gln Gly Val Asp Ala Asn Asn Ala Val Ile Ala Val
            485                 490                 495
Asn Thr Thr Asn Pro Asp Gly Ser Tyr Arg Ser Gln Val Met Arg Trp
            500                 505                 510
Asp Trp Ala Ser Thr Asn Val Ile Phe Asn Asn Arg Pro Leu Phe Ala
            515                 520                 525
Gly Gln Tyr Thr Pro Trp Asp Ser Gly Asn Phe Asp Pro Ser Thr Lys
            530                 535                 540
Leu Thr Val Ser Ala Thr Asn Gln Ile Ser Gly Pro Thr Gly Ile Arg
545                 550                 555                 560
Asn Thr Asn Gly Asn Thr Gly Asn Met Asn Thr Trp Gly Ser Gly Ser
            565                 570                 575
Thr Thr Ala Ser Tyr Gly Asn Ala Ala Ile Gln Ile Phe Gly Lys Gly
            580                 585                 590
Gly Gly Glu Pro Ala Ala Ile Tyr Phe Asp Asn Ser Gln Thr Gly Trp
            595                 600                 605
Tyr Leu Gly Met Asp Lys Asp Gly Gln Leu Lys Arg Ala Gly Trp Ser
            610                 615                 620
Leu Gly Asn Asn Ser Tyr Val Ile Thr Asp Glu Ser Asn Ile Arg Thr
625                 630                 635                 640
His Ile Asn Thr Met Ala Ala Arg Pro Ile Trp Gly Asn Val Glu Phe
            645                 650                 655
Trp Gly Pro Trp Asn Phe Asp Pro Asn Leu Lys Leu Thr Leu Asn Ala
            660                 665                 670
Phe Asn Asp Ser Ser Tyr Thr Arg Met Thr Asn Ser Gly Ala Lys Asp
            675                 680                 685
Val Gly Ile Ala Ser Met Thr Ser Tyr Ala Asp Ala Ala Met Ser Phe
            690                 695                 700
Phe Asn Tyr Glu Ala Ser Asn Pro Thr Gly Pro Arg Ala Ala Val Ile
705                 710                 715                 720
Ser Phe Val Arg Asn Gly Ser Arg Gly Val Leu Phe Gly Leu Asp Ser
            725                 730                 735
Asp Asn Lys Leu Lys Trp Gly Gly Tyr Ser Leu Gly Ala Val Ala Phe
            740                 745                 750
Glu Ile Ala Asp Ser Asn Asn Leu Met Ser Leu Trp Ser Ser His Ala
```

```
            755                 760                 765
Ala Ala Pro Asn Trp Asn Gly Gln Thr Ile Trp Arg Ser Gly Asn Phe
    770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
        835                 840                 845

Asp Ala Asp Asn Val Val Lys Ile Gly Gly Gly Thr Met Gly Gly Val
    850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Gly Val Gly Ser Tyr Ala Ile Leu
                885                 890                 895

Ala Val Leu Asp Thr Ser Ala Pro Ala Ala Ser Ile Ala Pro Gly Thr
            900                 905                 910

Ile Met Asp Ser Ser Lys Leu Phe Tyr Ser Ser Cys Asp Ser Thr Tyr
        915                 920                 925

Arg Ser Ser Ala Ser Pro Thr Gly Thr Trp Arg Cys Met Gly Tyr Val
    930                 935                 940

Tyr Asn Arg Asp Ser Thr Asn Gly Asp Ser Ala Ser Leu Phe Gln Arg
945                 950                 955                 960

Val Thr

<210> SEQ ID NO 67
<211> LENGTH: 962
<212> TYPE: PRT
<213> ORGANISM: Bacteriophage NH-4

<400> SEQUENCE: 67

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Arg Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Thr Asn Ile Pro Met Pro Ala Gly Gly Pro Gly
    130                 135                 140

Leu Ser Ser Gly Gly Glu Val Ile Thr Gly Arg Asn Phe Asn Glu
145                 150                 155                 160

Leu Leu Asn Gly Thr Trp Glu Phe Phe Ser Asp Ala Ile Val Val Ala
```

```
            165                 170                 175
Ser Gln Asn Ala Pro Val Tyr Pro Ala Ser Gly Ala Ala Gly
            180                 185                 190

Met Leu Glu Ala Lys Ser Trp Val Ser Gly Ser Asn Thr Phe Cys Val
            195                 200                 205

Gln Arg Tyr Thr Asp Arg Val Gly Asn Val Ala Val Arg Gly Leu Asn
            210                 215                 220

Ala Gly Ala Trp Thr Asn Trp Met Tyr Ala Val Asn Val Met Ala Leu
225                 230                 235                 240

Gln His Gly Arg Val Thr Tyr Gly Thr Ala Ala Gly Pro Ala Asn Ala
            245                 250                 255

Tyr Thr Leu Thr Leu Val Pro Gln Ile Gln Gly Gly Leu Val Asp Gly
            260                 265                 270

Met Ile Leu Arg Val Lys Phe Asn Thr Met Asn Thr Gly Ala Thr Thr
            275                 280                 285

Ile Asn Val Ser Gly Leu Gly Ala Lys Ala Ile Val Gly Ala Ala Asn
            290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
            325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
            355                 360                 365

Trp Thr Asp Val Val Asn Lys Pro Asn Val Ala Ile Gln Asp Thr Thr
            370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
            405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
            435                 440                 445

Gln Pro Arg Leu Asp Val Ala Lys Asn Leu Ala Tyr Ile Ala Asn Ser
            450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
            485                 490                 495

Asn Thr Thr Asn Pro Asp Gly Ser Tyr Arg Ser Gln Val Met Arg Trp
            500                 505                 510

Asp Trp Ala Ser Thr Asn Val Ile Phe Asn Asn Arg Pro Leu Phe Ala
            515                 520                 525

Gly Gln Tyr Thr Pro Trp Asp Ser Gly Asn Phe Asp Pro Ser Thr Lys
            530                 535                 540

Leu Thr Val Ser Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Gly Ser
            565                 570                 575

Thr Thr Ala Ser Tyr Gly Asn Ala Ala Ile Gln Ile Phe Gly Lys Gly
            580                 585                 590
```

Gly Gly Glu Pro Ala Ala Ile Tyr Phe Asp Asn Ser Gln Thr Gly Trp
            595                 600                 605

Tyr Leu Gly Met Asp Lys Asp Gly Gln Leu Lys Arg Ala Gly Trp Ser
        610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Asn Val Glu Phe
                645                 650                 655

Trp Gly Pro Trp Asn Phe Asn Pro Asn Thr Lys Leu Thr Leu Gly Ser
            660                 665                 670

Phe Asn Asp Ser Gln His Thr Arg Met Val Asn Ser Ala Ala Lys Asp
        675                 680                 685

Val Gly Ile Ala Ser Met Thr Ser Tyr Ala Asp Ala Ala Met Ser Phe
    690                 695                 700

Phe Asn Tyr Glu Ala Ser Thr Pro Thr Gly Asn Arg Ala Ala Val Ile
705                 710                 715                 720

Ser Phe Val Arg Asn Gly Ala Arg Gly Val Leu Phe Gly Leu Asp Thr
                725                 730                 735

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
        755                 760                 765

Ala Ala Pro Asn Trp Asn Gly Gln Thr Ile Trp Arg Ser Gly Asn Phe
    770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
        835                 840                 845

Asp Ala Asp Asn Val Val Lys Ile Gly Gly Thr Met Gly Gly Val
    850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Gly Val Gly Ser Tyr Ala Ile Leu
                885                 890                 895

Ala Val Leu Asp Thr Ser Ala Pro Ala Ser Ile Ala Pro Gly Thr
            900                 905                 910

Ile Met Asp Ser Ser Lys Leu Phe Tyr Ser Ser Cys Asp Ser Thr Tyr
        915                 920                 925

Arg Ser Ser Ala Arg Pro Thr Gly Thr Trp Arg Cys Met Gly Tyr Val
    930                 935                 940

Tyr Asn Arg Asp Ser Thr Asn Gly Asp Ser Ala Ser Leu Phe Gln Arg
945                 950                 955                 960

Val Thr

<210> SEQ ID NO 68
<211> LENGTH: 962
<212> TYPE: PRT
<213> ORGANISM: Bacteriophage 14-1

<400> SEQUENCE: 68

-continued

```
Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
                20                  25                  30

Asp Gly Tyr Thr Pro Asp Tyr Glu Ile Ser Leu Ala Ser Asn Asn Pro
            35                  40                  45

Gln Ala Lys Ala Val Glu Arg Lys Ile Gln Asn Gln Leu Phe Phe Ile
50                      55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
            115                 120                 125

Trp Ser Val Met Arg Ser Ser Ile Pro Met Pro Ala Gly Gly Pro Gly
130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Ile Ser Arg Ser Asn Thr Phe Cys Val
            195                 200                 205

Gln Arg Tyr Thr Asp Arg Val Gly Asn Val Ala Val Arg Gly Leu Asn
210                 215                 220

Ala Gly Glu Trp Thr Asn Trp Met Tyr Ala Val Asn Val Met Ala Leu
225                 230                 235                 240

Gln Gln Gly Arg Val Thr Tyr Gly Val Ala Ala Gly Pro Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Val Asn Thr Gly Ala Ser Thr
            275                 280                 285

Ile Asn Val Ser Gly Leu Gly Ala Lys Ala Ile Val Gly Ala Ala Asn
290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
            355                 360                 365

Trp Thr Asp Val Val Asn Lys Pro Asn Val Ala Ile Gln Asp Thr Thr
            370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415
```

```
Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
        435                 440                 445

Gln Pro Arg Leu Asp Val Ala Lys Asn Leu Ala Tyr Ile Ala Asn Ser
    450                 455                 460

Gly Pro Ile Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Val Met Arg Trp
            500                 505                 510

Asp Trp Ala Ser Thr Asn Val Ile Phe Asn Asp Arg Pro Leu Phe Ala
        515                 520                 525

Gly Gln Tyr Thr Pro Trp Asp Ser Gly Asn Phe Asp Pro Ser Thr Lys
    530                 535                 540

Leu Thr Val Ser Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Ile Gln Ile Phe Gly Lys Gly
            580                 585                 590

Gly Gly Glu Pro Ala Ala Ile Tyr Phe Asp Asn Ser Gln Thr Gly Trp
        595                 600                 605

Tyr Leu Gly Met Asp Lys Asp Gly Arg Leu Lys Arg Ala Gly Trp Ser
    610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Asn Val Glu Phe
                645                 650                 655

Trp Gly Pro Trp Asn Phe Asp Pro Asn Leu Lys Leu Thr Leu Asn Ala
            660                 665                 670

Phe Asn Asp Ser Ser Tyr Thr Arg Met Thr Asn Ser Gly Ala Lys Asp
        675                 680                 685

Val Gly Ile Ala Ser Met Thr Ser Tyr Ala Asp Ala Ala Met Ser Phe
    690                 695                 700

Phe Asn Tyr Glu Ala Ser Asn Pro Thr Gly Pro Arg Ala Ala Val Ile
705                 710                 715                 720

Ser Phe Val Arg Asn Gly Ser Arg Gly Val Leu Phe Gly Leu Asp Ser
                725                 730                 735

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
        755                 760                 765

Ala Ala Pro Asn Trp Asn Gly Gln Thr Ile Trp Arg Ser Gly Asn Phe
    770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
```

```
                    835                 840                 845
Asp Ala Asp Asn Val Val Lys Ile Gly Gly Gly Thr Met Gly Gly Val
        850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Gly Val Gly Ser Tyr Gly Ile Phe
                885                 890                 895

Ala Val Leu Asp Asn Ala Ala Pro Ile Ala Thr Val Gln Pro Gly Val
        900                 905                 910

Val Val Asp Gly Ser Ile Leu Ile Tyr Ser Ser Cys Ala Ala Asn Tyr
                915                 920                 925

Asn Ser Gly Gln Arg Pro Ala Gly Thr Trp Arg Cys Met Gly Tyr Val
        930                 935                 940

Val Asn Arg Asp Ala Asn Thr Pro Asp Ser Ala Thr Leu Phe Gln Arg
945                 950                 955                 960

Val Thr

<210> SEQ ID NO 69
<211> LENGTH: 962
<212> TYPE: PRT
<213> ORGANISM: Bacteriophage PTP47

<400> SEQUENCE: 69

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
                20                  25                  30

Asp Gly Tyr Thr Pro Asp Tyr Glu Ile Ser Leu Ala Ser Asn Asn Pro
            35                  40                  45

Gln Ala Lys Ala Val Glu Arg Lys Ile Gln Asn Gln Leu Phe Phe Ile
        50                  55                  60

Ala Thr Gln Asn Ala Gln Ala Trp Gln Arg Gln Met Ala Pro Pro Trp
65                  70                  75                  80

Phe Gln Asp Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Ala Met Arg Ser Asn Ile Pro Met Pro Ala Gly Gly Pro Gly
130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
        210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
```

```
                      245                 250                 255
Tyr Thr Leu Thr Leu Val Pro Gln Leu Gln Gly Gly Leu Val Asp Gly
                260                 265                 270

Met Ile Leu Arg Val Lys Phe Asn Thr Met Asn Thr Gly Ala Thr Thr
            275                 280                 285

Ile Asn Val Ser Gly Leu Gly Ala Lys Ala Ile Val Gly Ala Ala Asn
        290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Ala Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
        435                 440                 445

Gln Pro Arg Leu Asp Val Ala Lys Asn Leu Ala Tyr Ile Ala Asn Ser
    450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Val Met Arg Trp
            500                 505                 510

Asp Trp Ala Ser Thr Asn Val Ile Phe Asn Asn Arg Pro Leu Phe Ala
        515                 520                 525

Gly Gln Tyr Thr Pro Trp Asp Ser Gly Asn Phe Asp Pro Ser Thr Lys
    530                 535                 540

Leu Thr Val Ser Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Ile Arg Ile Phe Gly Lys Gly
            580                 585                 590

Gly Gly Glu Pro Ala Ala Ile Tyr Phe Asp Asn Ser Gln Thr Gly Trp
        595                 600                 605

Tyr Leu Gly Met Asp Lys Asp Gly Gln Leu Lys Arg Ala Gly Trp Ser
    610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Asn Val Glu Phe
                645                 650                 655

Trp Gly Pro Trp Asn Phe Asn Pro Asn Thr Lys Leu Thr Leu Gly Ser
            660                 665                 670
```

```
Phe Asn Asp Gly Gln His Thr Arg Met Val Asn Ser Ala Ala Lys Asp
            675                 680                 685

Val Gly Ile Ala Ser Met Thr Ser Tyr Ala Asp Ala Ala Met Ser Phe
        690                 695                 700

Phe Asn Tyr Glu Ala Ser Thr Pro Thr Gly Asn Arg Ala Ala Val Ile
705                 710                 715                 720

Ser Phe Val Arg Asn Gly Ala Arg Gly Val Leu Phe Gly Leu Asp Thr
                725                 730                 735

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
        755                 760                 765

Ala Ala Pro Asn Trp Asn Gly Gln Thr Ile Trp Arg Ser Gly Asn Phe
    770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Thr Ala Ala
            820                 825                 830

Ala Ile Thr Phe His Ser Pro Gln Lys Tyr His Val Asn Phe Gly Leu
        835                 840                 845

Asp Ala Asp Asn Val Val Lys Ile Gly Gly Gly Thr Met Gly Gly Val
    850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Glu Val Gly Ser Tyr Gly Ile Phe
                885                 890                 895

Ala Val Leu Asp Tyr Ala Ala Pro Thr Ala Thr Val Arg Pro Gly Val
            900                 905                 910

Val Val Asp Gly Ser Ile Leu Ile Tyr Ser Ser Cys Ala Ala Asn Tyr
        915                 920                 925

Asn Ser Gly Gln Arg Pro Ala Gly Thr Trp Arg Cys Met Gly Tyr Val
    930                 935                 940

Val Asn Arg Asp Ala Asn Thr Pro Asp Ser Ala Thr Leu Phe Gln Arg
945                 950                 955                 960

Val Thr

<210> SEQ ID NO 70
<211> LENGTH: 962
<212> TYPE: PRT
<213> ORGANISM: Bacteriophage SN

<400> SEQUENCE: 70

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80
```

-continued

```
Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Ser Asn Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ala
                165                 170                 175

Ser Gln Asn Ala Pro Val Tyr Pro Ala Ser Ala Gly Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Met Asn Thr Gly Ala Ser Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Ala Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
        435                 440                 445

Gln Pro Arg Leu Asp Val Ala Lys Asn Leu Ala Tyr Ile Ala Asn Ser
    450                 455                 460

Gly Ser Leu Trp Gln Asn Thr Thr Ala Asp Gln Pro Gly Trp Lys Phe
465                 470                 475                 480

Thr Phe Ala Gln Gly Val Asp Ala Asn Asn Asn Ala Val Ile Ala Val
                485                 490                 495
```

```
Asn Thr Thr Asn Pro Asp Gly Ser Tyr Arg Ser Gln Val Met Arg Trp
                500                 505                 510

Asp Trp Ala Ser Thr Asn Val Ile Phe Asn Asn Arg Pro Leu Phe Ala
            515                 520                 525

Gly Gln Tyr Thr Pro Trp Asp Ser Gly Asn Phe Asp Pro Ser Thr Lys
        530                 535                 540

Leu Thr Val Arg Ala Thr Asn Gln Ile Ala Gly Pro Thr Gly Ile Gln
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Ile Gln Ile Phe Gly Lys Gly
            580                 585                 590

Gly Gly Glu Pro Ala Ala Ile Tyr Phe Asp Asn Ser Gln Thr Gly Trp
        595                 600                 605

Tyr Leu Gly Met Asp Lys Asp Gly Gln Leu Lys Arg Ala Gly Trp Ser
        610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Gly Val Glu Phe
                645                 650                 655

Trp Gly Pro Trp Asn Phe Asn Pro Asn Thr Lys Leu Thr Leu Gly Ser
            660                 665                 670

Phe Asn Asp Ser Gln His Thr Arg Met Val Asn Ser Ala Ala Lys Asp
        675                 680                 685

Val Gly Ile Ala Ser Met Thr Ser Tyr Ala Asp Ala Ala Met Ser Phe
690                 695                 700

Phe Asn Tyr Glu Ala Ser Thr Pro Thr Gly Asn Arg Ala Ala Val Ile
705                 710                 715                 720

Ser Phe Val Arg Asn Gly Ala Arg Gly Val Leu Phe Gly Leu Asp Thr
                725                 730                 735

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
        755                 760                 765

Ala Ala Pro Asn Trp Asn Gly Gln Thr Ile Trp Arg Ser Gly Asn Phe
770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
        835                 840                 845

Asp Ala Asp Asn Val Val Lys Ile Gly Gly Thr Met Gly Gly Val
850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Gly Val Gly Ser Tyr Gly Ile Phe
                885                 890                 895

Ala Val Leu Asp Asn Ala Ala Pro Thr Ala Thr Val Gln Pro Gly Val
            900                 905                 910

Val Val Asp Gly Ser Ile Leu Ile Tyr Ser Ser Cys Ala Ala Asn Tyr
```

```
            915                 920                 925
Asn Ser Gly Gln Arg Pro Ala Gly Thr Trp Arg Cys Met Gly Tyr Val
        930                 935                 940

Val Asn Arg Asp Ala Asn Thr Pro Asp Ser Ala Thr Leu Phe Gln Arg
945                 950                 955                 960

Val Thr
```